(12) United States Patent
Noble et al.

(10) Patent No.: US 11,672,265 B2
(45) Date of Patent: Jun. 13, 2023

(54) EGG REPLACEMENT CONTAINING EUGLENA-DERIVED COMPONENTS

(71) Applicant: NOBLEGEN, INC., Peterborough (CA)

(72) Inventors: Adam J. Noble, Peterborough (CA); Somayeh Sabouri, Peterborough (CA); Angela Swain, Peterborough (CA); Peeyush Maheshwari, Peterborough (CA); Lauren Elizabeth Cameron, Peterborough (CA); Athira Mohanan, Peterborough (CA)

(73) Assignee: Noblegen, Inc., Peterborough (CA)

(*) Notice: Subject to any disclaimer, the term of this patent is extended or adjusted under 35 U.S.C. 154(b) by 0 days.

(21) Appl. No.: 17/783,990

(22) PCT Filed: Dec. 9, 2020

(86) PCT No.: PCT/IB2020/061714
§ 371 (c)(1),
(2) Date: Jun. 9, 2022

(87) PCT Pub. No.: WO2021/116949
PCT Pub. Date: Jun. 17, 2021

(65) Prior Publication Data
US 2023/0055716 A1    Feb. 23, 2023

Related U.S. Application Data

(60) Provisional application No. 62/945,599, filed on Dec. 9, 2019.

(51) Int. Cl.
| | |
|---|---|
| *A23J 3/20* | (2006.01) |
| *A23L 15/00* | (2016.01) |
| *A23J 1/14* | (2006.01) |
| *A23L 33/185* | (2016.01) |
| *A23J 3/14* | (2006.01) |
| *A23L 33/195* | (2016.01) |
| *A23J 1/12* | (2006.01) |

(52) U.S. Cl.
CPC ............ *A23L 15/35* (2016.08); *A23J 1/12* (2013.01); *A23J 1/14* (2013.01); *A23J 3/14* (2013.01); *A23J 3/20* (2013.01); *A23L 33/185* (2016.08); *A23L 33/195* (2016.08)

(58) Field of Classification Search
CPC ...... A23L 15/35; A23L 33/185; A23L 33/195; A23J 1/12; A23J 1/14; A23J 3/14; A23J 3/20
USPC .......................................................... 426/656
See application file for complete search history.

(56) References Cited

U.S. PATENT DOCUMENTS

2010/0303989 A1* 12/2010 Brooks .................. A21D 2/267
426/615

FOREIGN PATENT DOCUMENTS

| CA | 2500125 A1 | 9/2005 |
| CA | 2740415 A1 | 4/2010 |
| WO | 2021116949 A1 | 6/2021 |

OTHER PUBLICATIONS

FR 3 110339-Machine Translation (Year: 2021).*
International Search Report and Written Opinion for PCT/IB2020/061714 dated Mar. 2, 2021.
"Noblegen Achieves Self-GRAS Affirmation for Protein-Rich Euglena Flour" Dec. 4, 2019, https://m.canadianinsider.com/noblegen-achieves-self-gras-affirmation-for-protein-rich-euglena-flour.
US FDA GRAS Notice 697, GRAS Notice for Dried Euglena gracilis (ATCC-PTA 123017) Mar. 16, 2017, https://www.fda.gov/media/106482/download.

* cited by examiner

*Primary Examiner* — Hamid R Badr
(74) *Attorney, Agent, or Firm* — DLA Piper LLP

(57) ABSTRACT

Embodiments herein are directed to egg replacement compositions, egg replacement emulsions, liquid eggs, liquid egg formulations, or egg replacement formulations and the use of each in a variety of food products, wherein the egg replacement compositions, egg replacement emulsions, liquid eggs, liquid egg formulations, or egg replacement formulations possess one or more functional properties similar to a natural egg.

20 Claims, 23 Drawing Sheets

A

B

EGG REPLACEMENT CONTAINING EUGLENA-DERIVED COMPONENTS

CROSS-REFERENCE TO RELATED APPLICATIONS

This application is a U.S. National Stage filing under 35 U.S.C. § 371 of International PCT Application No. PCT/IB2020/061714, filed Dec. 9, 2020, which claims the benefit of U.S. Provisional Application No. 62/945,599 entitled "Egg Replacement Containing *Euglena*-Derived Components," filed Dec. 9, 2019, each of which is hereby incorporated by reference in its entirety.

SUMMARY OF THE INVENTION

Embodiments described herein are directed to a dry egg replacement composition comprising about 10% to about 98% *Euglena*-derived material, about 10% to about 85% pea protein, and one or more additional ingredient, wherein the dry egg replacement composition comprises one or more functional property of a natural egg.

Embodiments described herein are directed to an egg replacement emulsion comprising a dry egg replacement composition, an oil, and water.

Embodiments described herein are directed to a liquid egg comprising a dry egg replacement composition, an oil, and water.

Embodiments described herein are directed to methods of preparing an egg scramble comprising combining a dry egg replacement mix, an oil, and water.

Embodiments described herein are directed to a liquid egg formulation comprising about 50% to about 85% fresh *Euglena*-derived material, about 5% to about 10% pea protein, and one or more additional ingredient, wherein the liquid egg formulation comprises one or more functional property of a natural egg.

Embodiments described herein are directed to a liquid egg formulation comprising about 12% to about 95% *Euglena*-derived wet protein concentrate, about 1% to about 20% solid content, and one or more additional ingredient, wherein the liquid egg formulation comprises one or more functional property of a natural egg.

Embodiments described herein are directed to various food applications wherein the dry egg replacement composition, the egg replacement emulsion, liquid egg, or liquid egg formulation has been incorporated into edible egg-free scrambled eggs, egg-free patty, egg-free frittata, egg-free chocolate cake, egg-free pound cake, egg-free angel food cake, egg-free yellow cake, egg- and dairy-free cream cheese, egg-free pasta dough, egg-free custard, egg-free ice cream, and dairy-free milk.

DETAILED DESCRIPTION

Figure 1:
FIG. 1 shows an early prototype of the development of the egg replacement.

As a civilization we face significant challenges in the years ahead. The population growth predicted over the next few decades, about 9.7 billion global population by 2050, will cause severe food shortages. Malnutrition is a leading cause of death, accounting for about 3.5 million deaths per year. Global deforestation will cause the loss of a significant portion of the food we rely on currently, i.e. palm oil. The resources we utilize currently are unsustainable, two planets worth of resources will be needed to support the expected population by 2050. Accordingly, there is a significant need to identify sustainable alternatives. For example, food sources that can provide improved functionality, higher nutritional value, minimal waste stream, reduced water usages and reduced carbon dioxide emissions.

Microalgae are a rich source of protein, essential fatty acids, vitamins, and minerals. After lipid removal, the residual biomass contains even higher concentrations of protein and other nutrients. Microalgae are good sources of long chain polyunsaturated fatty acids ("PUFA") and have been used to enrich diets with omega-3 PUFA. Described herein are, inter alia, novel techniques for extracting a variety of components from heterotrophically cultivated microalgae, e.g., *Euglena*, without the use of harsh chemicals or solvents.

A specific species of algae named *Euglena gracilis* (hereinafter *Euglena*) belongs to a group of single-celled microscopic algae, that is often used as a candidate species for laboratory studies and technological applications. *Euglena* possess the representative features typical of eukaryotic cells such as a mitochondria, nucleus, and lysosome. *Euglena* can further be characterized for its long flagellum and large red eyespot. They are distinctive as they can produce their own nourishment (autotrophic) similar to plants, as well as eat and digest external food sources (heterotrophic) like animals. *Euglena* is a demonstrated, multifaceted model organism for study. Through optimizing the natural ability to employ singly or both modes of nourishment, *Euglena* can be directed to produce target compounds by adjusting key parameters in the production process. These critical adjustments can be used to enhance the natural mechanisms of the microorganism, to encourage rapid growth and the efficient conversion of valuable products with little waste production.

Eggs are a staple ingredient, found in most homes worldwide. As the population continues to lean towards a healthier and more sustainable lifestyle, this has led to a need in the marketplace for a sustainable, healthy egg alternative. The egg is a versatile affordable complete nutritive solution. Currently available vegan and plant based egg substitutes lack full nutritional benefits as well as essential amino acids, creating an incomplete protein product. Further, the commercially available egg substitute solutions lack the texture, flavor, and color of the commonly used chicken egg. Manufacturers of these products must add artificial colors or additional ingredients to mimic the natural yellow color of a chicken egg yolk. There has been widespread interest in a suitable replacement for the egg for quite some time, due to spoilage, concern for animal welfare, environmental damage from the industrial poultry, and *salmonella* risks in natural eggs.

The egg replacement described herein includes many advantages over previous egg replacement: 1) no risk of any avian-related disease contaminating the product, 2) can be used as scrambled egg analog providing a complete nutritive egg replacement, 3) can be used to replace eggs in the manufacture of various types of foods, such as bakery products, condiments, noodles, etc., and 4) can be used to replace eggs in the manufacture of specialty items such as shampoo, pet foods and adhesive products.

The egg replacement described herein is suitable for various food applications for example, edible egg-free emulsion, egg analog, egg-free scrambled eggs, egg-free patty, egg-free bakery items, egg-free cream cheese, egg-free pasta dough, egg-free custard, and egg-free ice cream.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Where a range of values is provided, it is intended that each intervening value between the upper and lower limit of that range and any other stated or intervening value in that stated range is encompassed within the disclosure. For example, if a range of 1 g to 8 g is stated, it is intended that 2 g, 3 g, 4 g, 5 g, 6 g, and 7 g are also explicitly disclosed, as well as the range of values greater than or equal to 1 g and the range of values less than or equal to 8 g.

The singular forms "a," "an," and "the" include plural referents unless the context clearly dictates otherwise. Thus, for example, reference to an "egg" includes a single egg as well as two or more of the same or different types of eggs.

The word "about" when immediately preceding a numerical value means a range of plus or minus 5% of that value, e.g., "about 50" means 45 to 55, "about 25,000" means 22,500 to 27,500, etc., unless the context of the disclosure indicates otherwise, or is inconsistent with such an interpretation. Furthermore, the phrases "less than about" a value or "greater than about" a value should be understood in view of the definition of the term "about" provided herein.

"Baked good" means a food item, typically found in a bakery, that is prepared by using an oven and usually contain a leavening agent. Baked goods include, but are not limited to breads, brownies, cookies, pies, cakes and pastries.

"Bread" means a food item that contains flour, liquid, and usually a leavening agent. Breads are usually prepared by baking in an oven, although other methods of cooking are also acceptable. The leavening agent can be chemical or organic/biological in nature. Typically, the organic leavening agent is yeast. In the case where the leavening agent is chemical in nature (such as baking powder and/or baking soda), these food products are referred to as "quick breads." Crackers and other cracker-like products are examples of breads that do not contain a leavening agent.

The transitional term "comprising," which is synonymous with "including," "containing," or "characterized by," is inclusive or open-ended and does not exclude additional, un-recited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

"Dispersion" refers to a distribution of particles more or less evenly throughout a medium, including a liquid or gas. One common form of dispersion is an emulsion made up of a mixture of two or more immiscible liquids such as oil and water.

"Dry weight" means weight determined in the relative absence of water. For example, reference to a dry mixture refers to a specified percentage of a particular component(s) by dry weight as a percentage and is calculated based on the weight of the composition before any liquid has been added.

As used herein, the term "eggs" includes but is not limited to chicken eggs, other bird eggs (such as quail eggs, duck eggs, ostrich eggs, turkey eggs, bantam eggs, goose eggs), and fish eggs such as fish roe. Typical food application comparison is made with respect to chicken eggs.

As used in this disclosure, the terms "emulsifying," "emulsion" or a derivative thereof refers to where a substance is present in a food composition or food product as a single-phase mixture where a two-phase system of oil and water would normally have existed. An emulsion thus refers to a kinetically stable mixture of two normally immiscible liquids, i.e. oil and water. In some other foods, the water is dispersed in oil.

"Edible ingredient" means any substance or composition which is fit to be eaten. "Edible ingredients" include, without limitation, grains, fruits, vegetables, proteins, herbs, spices, carbohydrates, and fats.

As used herein, the term "enriched" refers to an increase in a percent amount of a molecule, for example, a protein, in one sample relative to the percent amount of the molecule in a reference sample. In some embodiments, the enrichment is on a weight to weight basis. In some embodiments, the enrichment refers to an increase of about 5%, 10%, 15%, 20%, 25%, 30%, 35%, 40%, 45%, or 50% relative to the reference value or amount. In some embodiments, the enrichment refers to an increase of at least about 5%, 10%, 15%, 20%, 25%, 30%, 35%, 40%, 45%, or 50% relative to the reference value or amount.

"Finished food product" and "finished food ingredient" mean a food composition that is ready for packaging, use, or consumption. For example, a "finished food product" may have been cooked or the ingredients comprising the "finished food product" may have been mixed or otherwise integrated with one another. A "finished food ingredient" is typically used in combination with other ingredients to form a food product.

The term "functional food product" as used herein refers to a food product given an additional function by adding new ingredients or more of existing ingredients. For example, where protein is added to a food product to provide texture, water holding capacity or nutritional support to a food product.

"Food," "food composition," "food product," and "foodstuff" mean any composition intended to be or expected to be ingested by humans or other animals as a source of nutrition and/or calories. Food compositions are composed primarily of carbohydrates, fats, water and/or proteins and make up substantially all of an individual's daily caloric intake.

The term "gelling," "gelification" or a derivative thereof as used herein refers to a food composition or a food product in a gelatinous form. A gelatinous form is created by incorporating solids and liquids into a uniform three dimensional, semi-solid structure. A gelatinous food product is considered a soft gel when its tensile strength is in the range of 500-1000 $g/cm^2$, as seen in, for example, jelly and jams, nut butters (e.g. just nuts versions), jelly-like products, and fondant. A gelatinous food product is considered a hard gel when its tensile strength is in the range of 1000-3000 $g/cm^2$, as seen in, for example, gummy candy, confectionary gels (i.e. cookie filling), fruit gel bars, and fruit snacks.

"Foamability" as used herein, refers to the ability of a material to rapidly adsorb on the air-liquid interface during whipping or bubbling, and to form a cohesive viscoelastic film by way of intermolecular interactions.

The term "fresh biomass" or "fresh *Euglena* biomass" as used herein refers to biomass or *Euglena* biomass that is not frozen or dried after harvesting and is kept at 4° C. until use.

"Good manufacturing practice" and "GMP" mean those conditions established by regulations set forth at 21 C.F.R. 110 (for human food) and 111 (for dietary supplements), or comparable regulatory schemes established in locales outside the United States. The U.S. regulations are promulgated by the U.S. Food and Drug Administration under the authority of the Federal Food, Drug, and Cosmetic Act to regulate manufacturers, processors, and packagers of food products and dietary supplements for human consumption. All of the processes described herein can be performed in accordance with GMP or equivalent regulations. In the United States, GMP regulations for manufacturing, packing, or holding human food are codified at 21 C.F.R. 110. These provisions, as well as ancillary provisions referenced therein, are hereby incorporated by reference in their entirety for all purposes. GMP conditions in the Unites States, and equivalent conditions in other jurisdictions, apply in determining whether a food is adulterated (the food has been manufactured under such conditions that it is unfit for food) or has been prepared, packed, or held under unsanitary conditions such that it may have become contaminated or otherwise may have been rendered injurious to health. GMP conditions can include adhering to regulations governing: disease control; cleanliness and training of personnel; maintenance and sanitary operation of buildings and facilities; provision of adequate sanitary facilities and accommodations; design, construction, maintenance, and cleanliness of equipment and utensils; provision of appropriate quality control procedures to ensure all reasonable precautions are taken in receiving, inspecting, transporting, segregating, preparing, manufacturing, packaging, and storing food products according to adequate sanitation principles to prevent contamination from any source; and storage and transportation of finished food under conditions that will protect food against physical, chemical, or undesirable microbial contamination, as well as against deterioration of the food and the container.

"Increased lipid yield" means an increase in the lipid/oil productivity of a microalgal culture that can achieved by, for example, increasing the dry weight of cells per liter of culture, increasing the percentage of cells that contain lipid, and/or increasing the overall amount of lipid per liter of culture volume per unit time.

The term "shaking" as used herein refers to the movement of a sample, in an up and down or side to side, rapid, forceful or jerky movement. This may be done manually, or mechanically.

The term "solution" as used herein refers to a homogeneous mixture of a substance (solute) dispersed through a liquid medium (solvent) that cannot be separated by the forces of gravity alone.

The term "solid content" as used herein refers to how much mass (i.e. biomass or protein concentrate) is in a liquid by weight of each.

The term "substantially free" as used herein refers to the complete or near complete lack of light or a component. For example, a composition that is "substantially free" of water would either completely lack water, or so nearly completely lack water that the effect would be the same as if it completely lacked water.

As used herein, the term "stability" and derivatives thereof refer to heat stability, freeze-thaw stability, light stability, emulsion stability, or storage stability. Heat stability is the ability of a product or material to retain the same properties after exposure to a high heat for a single set period of time or a cycling of exposure times. Freeze-thaw stability is the ability of a product or material to retain the same properties after being frozen and subsequently thawed, which can be cycled through a number of freeze thaw cycles. Light stability is the ability of a product or material to retain the same properties after exposure to a light, such as sunlight or indoor light for a single set period of time or a cycling of exposure times. Emulsion stability is the ability of a product or material to retain an emulsion or to prevent separating, over time. Further, the term "stabilizer" relates to a material that provides stability described herein when added to a product or another material. For example, a stabilizer may be an ingredient incorporated into a final food formulation which preserves the structure and sensory characteristics of a food product over time, which would not otherwise be maintained in the absence of the stabilizer.

The term "solubility" as used herein, refers to the maximum amount of a substance that is able to be completely dissolved in a solution, usually in a specific amount.

"Uncooked product" means a composition that has not been subjected to heating but may include one or more components previously subjected to heating.

As used herein, the term "viscosity" refers to the resistance of a fluid when attempting to flow, may also be thought of as a measure of fluid friction.

"W/W" or "w/w," in reference to proportions by weight, means the ratio of the weight of one substance in a composition to the weight of the composition. For example, reference to a composition that comprises 5% w/w microalgal biomass means that 5% of the composition's weight is composed of microalgal biomass (e.g., such a composition having a weight of 100 mg would contain 5 mg of microalgal biomass) and the remainder of the weight of the composition (e.g., 95 mg in the example) is composed of other ingredients.

"W/V" or "w/v" means the ratio of the weight of one substance in a composition to total volume of the composition. For example, reference to a composition that comprises 5% w/v microalgal biomass means that 5 g of microalgal biomass is dissolved in a final volume of 100 mL aqueous solution.

The term "whipping" as used herein, refers to the action of using a whisk, or a mixer to beat a sample in order to rapidly incorporate air and produce expansion.

The term "water holding capacity" or WHC or a derivative thereof as used herein relating to food composition or product refers to the ability to hold the food's own and added water during the application of forces, pressing, centrifugation, or heating. WHC may also be described as a physical property, for example, the ability of a food structure to prevent water from being released from the three-dimensional structure of, for example, a gel.

Throughout this disclosure, the *Euglena* may be selected from the group of species selected from *Euglena gracilis*, *Euglena sanguinea*, *Euglena deses*, *Euglena mutabilis*, *Euglena acus*, *Euglena virdis*, *Euglena anabaena*, *Euglena geniculata*, *Euglena oxyuris*, *Euglena proxima*, *Euglena tripteris*, *Euglena chlamydophora*, *Euglena splendens*, *Euglena texta*, *Euglena intermedia*, *Euglena polymorpha*, *Euglena ehrenbergii*, *Euglena adhaerens*, *Euglena clara*, *Euglena elongata*, *Euglena elastica*, *Euglena oblonga*, *Euglena pisciformis*, *Euglena cantabrica*, *Euglena granulata*, *Euglena obtusa*, *Euglena limnophila*, *Euglena hemichromata*, *Euglena variabilis*, *Euglena caudata*, *Euglena minima*, *Euglena communis*, *Euglena magnifica*, *Euglena terricola*, *Euglena velata*, *Euglena repulsans*, *Euglena clavata*, *Euglena lata*, *Euglena tuberculata*, *Euglena contabrica*, *Euglena ascusformis*, *Euglena ostendensis*, *Chlorella autotrophica*, *Chlorella colonials*, *Chlorella lewinii*, *Chlorella minutissima*, *Chlorella pituita*, *Chlorella pulchelloides*, *Chlorella pyrenoidosa*, *Chlorella rotunda*, *Chlorella singularis*, *Chlorella sorokiniana*, *Chlorella variabilis*, *Chlorella volutis*, *Chlorella vulgaris*, *Schizochytrium aggregatum*, *Schizochytrium limacinum*, *Schizochytrium minutum*, and combinations thereof. In certain embodiments, the microalgae is *Euglena gracilis*.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Dry Egg Replacement Composition

Embodiments described herein are directed to a dry egg replacement composition comprising about 10% to about 98% *Euglena*-derived material, about 10% to about 85% pea protein, and one or more additional ingredient, wherein the dry egg replacement composition comprises one or more functional property of a natural egg.

In embodiments described herein, the one or more additional ingredient is selected from the group consisting of gellan gum, methylcellulose, yeast extract, flavoring, antioxidant blend, and combinations thereof. In some embodiments, the flavoring is selected from the group consisting of black salt, sea salt, onion powder, and combinations thereof.

Embodiments described herein are directed to a dry egg replacement composition comprising about 1% to about 100% *Euglena*-derived material, about 0.05% to about 70% additional protein source, and one or more additional ingredient, wherein the dry egg replacement composition comprises one or more functional property of a natural egg.

In some embodiments of the dry egg replacement composition described herein, the additional protein source is selected from the group consisting of pea protein, soy protein, corn protein, wheat protein, rice protein, beans protein, seed protein, nut protein, almond protein, peanut protein, seitan protein, lentil protein, chickpea protein, flaxseed protein, wild rice protein, quorn protein, chia seed protein, *quinoa* protein, oat protein, fava bean protein, buckwheat protein, bulgar protein, millet protein, microalgae protein, yellow pea protein, mung bean protein, hemp protein, sunflower protein, canola protein, lupin protein, legumes protein, potato protein, and combinations thereof.

In some embodiments of the dry egg replacement composition herein, the additional protein source is in an amount of about 0.05% to about 70%, about 0.5% to about 70%, about 1% to about 70%, about 5% to about 70%, about 10% to about 70%, about 15% to about 70%, about 0.05% to about 60%, about 0.05% to about 50%, about 0.05% to about 40%, about 0.05% to about 30%, or about 0.05% to about 20%. In certain embodiments of the dry egg replacement composition described herein, the additional protein source is in an amount of about 0.05% to about 15%. In certain embodiments of the dry egg replacement composition described herein, the additional protein source is in an amount of about 20% to about 60%.

In some embodiments of the dry egg replacement composition described herein, the one or more additional ingredient is selected from the group consisting of gellan gum, methylcellulose, yeast extract, flavoring, antioxidant blend, maskers, leavening agents, baking powder, baking soda, enzymes, transglutaminase, emulsifiers, lecithin, mono- and diglycerides, binders, carrot fiber, defatted linseed flour, and combinations thereof.

In some embodiments of the dry egg replacement composition described herein, each of the one or more additional ingredient is in an amount of about 0.05% to about 5%, about 0.05% to about 4%, or about 0.05% to about 3%, or about 0.05% to about 2%. In certain embodiments of the dry egg replacement composition described herein, each of the one or more additional ingredient is in an amount of about 0.1% to about 1%.

In some embodiments, the flavoring is selected from the group consisting of black salt, black pepper, Himalayan sea salt, salt, onion powder, minced onion, roasted garlic, mushroom powder, yeast extract, and combinations thereof.

In embodiments described herein, the *Euglena*-derived material is selected from the group consisting of a *Euglena* biomass, a *Euglena*-derived protein, a protein-rich flour derived from *Euglena*, a protein concentrate derived from *Euglena*, a protein isolate derived from *Euglena*, a *Euglena*-derived beta-glucan isolate, a *Euglena*-derived oil, and combinations thereof.

In some embodiments of the dry egg replacement composition described herein, the dry egg replacement composition further comprises one or more hydrocolloids. In some embodiments the one or more hydrocolloids may be selected from the group consisting of locust bean gum, a guar gum, a konjac gum, a gellan gum, a high methoxy pectin, a low methoxy pectin, an Agar, a kappa carrageenan, an iota carrageenan, a lambda carrageenan, an alginate, a curdlan, a methyl cellulose, a carboxymethyl cellulose (CMC), a xanthan gum, a gum Arabic, a *Euglena* derived beta-glucan and combinations thereof.

In some embodiments of the dry egg replacement composition herein, each of the one or more hydrocolloids is in an amount of about 0.05% to about 8%, about 0.1% to about 8%, about 0.05% to about 7%, about 0.05% to about 6%, about 0.05% to about 5%, about 0.05% to about 4%, or about 0.05% to about 3%. In certain embodiments of the dry egg replacement composition described herein, each of the one or more hydrocolloids is in an amount of about 0.1% to about 2%.

Complete Nutrition

The dry egg replacement described herein has a similar nutritional content as a natural egg, which previous attempts to create an egg substitute have failed to attain.

To be equivalent to a natural egg, egg replacement composition must have a protein content of 6 g per serving. Previous attempts and commercially available egg substitutes are only able to achieve 5 g per serving. The dry egg replacement composition described herein contains the same amount of protein as a chicken egg. In embodiments described herein, the dry egg replacement composition contains at least 6 g of complete protein per serving size. In certain embodiments, the dry egg replacement composition contains about 6 g to about 10 g, about 6 g to about 9 g, about 6 g to about 8 g, about 6 g to about 7 g, or about 6 g to about 6.5 g of complete protein per serving size. In embodiments described herein, the serving size of the dry egg replacement composition is about 9 g to about 15 g, about 10 g to about 14 g, about 11 g to about 13 g, or about 12 g to about 12.5 g. In embodiments described herein, the serving size of the dry egg replacement composition is about 12.5 g. In certain embodiments, the dry egg replacement composition is mixed with an oil and water to create an emulsion wherein the liquid serving size is from about 50 g to about 100 g, about 60 g to about 90 g, about 70 g to about 80 g, or about 80 g to about 90 g. In certain embodiments, the dry egg replacement composition is mixed with an oil and water to create an emulsion wherein the liquid serving size is about 80 g to about 90 g.

The combination of *Euglena*-derived material and pea protein established the nutritional profile similar to a natural egg, including at least 6 g of protein, about 5 g of fat, about 180 mg cholesterol, about 60 mg of sodium, about 60 mg potassium, about 0.6 g carbohydrates, and vitamins and minerals, including vitamin A, vitamin D, vitamin B-6, calcium, cobalamin, iron and magnesium. In certain embodiments, the egg replacement provides about 75 calories.

In certain embodiments, the dry egg replacement composition has a ratio of *Euglena*-derived material to pea protein of about 20:80 to about 50:50. In certain embodiments, the dry egg replacement composition has a ratio of *Euglena*-derived material to pea protein of about 25:75 to about 50:50. In certain embodiments, the dry egg replacement composition has a ratio of *Euglena*-derived material to pea protein of about 40:60.

In certain embodiments, the *Euglena*-derived material is in an amount of about 10% to about 98%, about 10% to about 95%, about 10% to about 85%, about 15% to about 75%, about 20% to about 65%, or about 25% to about 55% in the dry mixture. In certain embodiments, the *Euglena*-derived material is in an amount of about 5% to about 90% in the dry mixture. In certain embodiments, the *Euglena*-derived material is in an amount of about 40% to about 87% in the dry mixture. In certain embodiments, the *Euglena*-derived material is in an amount of about 40% to about 90% in the dry mixture. In certain embodiments, the *Euglena*-derived material is in an amount of about 35% in the dry mixture. In certain embodiments, the *Euglena*-derived material is in an amount of about 7% in the dry mixture. In certain embodiments, the *Euglena*-derived material is in an amount of about 35 g to about 70 g, about 40 g to about 65 g, about 45 g to about 60 g, or about 50 g to about 55 g in the dry mixture. In certain embodiments, the *Euglena*-derived material is in an amount of about 56 g in the dry mixture.

In certain embodiments, the pea protein is in an amount of about 5% to about 10%, about 5% to about 20%, about 10% to about 85%, about 15% to about 75%, about 20% to about 65%, or about 25% to about 55% in the dry mixture. In certain embodiments, the pea protein is in an amount of about 52% in the dry mixture. In certain embodiments, the pea protein is in an amount of about 55 g to about 95 g, about 60 g to about 90 g, about 55 g to about 85 g, or about 60 g to about 80 g in the dry mixture. In certain embodiments, the pea protein is in an amount of about 84 g in the dry mixture.

In certain embodiments, the total amount of protein blend in the dry egg replacement composition is about 60% to about 90% of the dry mixture. In certain embodiments, the protein blend includes the combination of *Euglena*-derived material and pea protein. In certain embodiments, the total amount of protein blend in the dry egg replacement composition is about 60%, about 65%, about 70%, about 75%, about 80%, about 85%, or about 90% of the dry mixture. In certain embodiments, the total amount of protein blend in the dry egg replacement composition is about 87% of the dry mixture.

In certain embodiments, the yeast extract is in an amount of about 0.2 g to about 5 g, about 0.5 g to about 4 g, about 1 g to about 3 g, or about 1.5 g to about 2 g in the dry mixture. In certain embodiments, the yeast extract is in an amount of about 1.4 g in the dry mixture. In certain embodiments, the amount of yeast extract in the dry egg replacement composition is from about 0.1% to about 5%, about 0.5% to about 4.5%, about 1% to about 4%, about 1.5% to about 3.5%, or about 2% to about 3% of the dry mixture. In certain embodiments, the amount of yeast extract in the dry egg replacement composition is about 0.1%, about 0.5%, about 1%, about 1.5%, about 2%, about 2.5%, about 3% about 3.5%, about 4%, about 4.5%, or about 5%, of the dry mixture. In certain embodiments, the amount of yeast extract in the dry egg replacement composition is about 1% of the dry composition. The yeast extract contributes to the overall nutritional content of the dry egg replacement composition necessary to match a natural egg. The yeast extract also provides an umami flavor to the final product.

In certain embodiments, the dry egg replacement composition is rich in beta-1,3-glucan. Beta-1,3-glucan provides health benefits including, but not limited to, immunity, antidiabetic properties, antihypoglycemic properties, and hepatoprotective properties.

In certain embodiments, the dry egg replacement composition contains essential nutrients. In certain embodiments, the essential nutrients are selected from the group consisting of amino acids, fatty acids, vitamins, minerals, and combinations thereof. In certain embodiments, the amino acids are selected from the group consisting of phenylalanine, valine, threonine, tryptophan, methionine, leucine, isoleucine, lysine, histidine, and combinations thereof. In certain embodiments, the fatty acids are selected from the group consisting of omega-3 fatty acids, omega-6 fatty acids, omega-9 fatty acids, or combinations thereof. In certain embodiments, the vitamins are selected from the group consisting of vitamin E, tocopherol, tocotrienols, vitamin A, vitamin C, vitamin D, vitamin K, thiamine (vitamin B1), riboflavin (vitamin B2), niacin (vitamin B3), pantothenic acid (vitamin B5), pyridoxine (vitamin B6), biotin (vitamin B7), folate (vitamin B9), cyanocobalamin (vitamin B12), vitamin D, and combinations thereof. In certain embodiments, the minerals are selected from the group consisting of potassium, chloride, sodium, calcium, phosphorus, sulfur, fluoride, magnesium, iron, zinc, manganese, copper, iodine, chromium, molybdenum, selenium, cobalt, and combinations thereof. In certain embodiments, the dry egg replacement composition contains vitamin A, riboflavin, pantothenic acid, vitamin B12, choline, phosphorus, zinc, and vitamin D.

In certain embodiments, the dry egg replacement composition contains medium-chain triglycerides (MCT), i.e. triglycerides with two or three fatty acids having an aliphatic tail of 6-12 carbon atoms. In certain embodiments, the MCTs are selected from the group consisting of caproic acid, caprylic, acid, capric acid, lauric acid, and combinations thereof Functional Properties The dry egg replacement composition described herein has been developed to provide the same functional benefits as a natural egg. The functional properties are measured and evaluated using the dry egg replacement composition, the egg replacement emulsion, liquid egg, or liquid egg formulation described herein.

In embodiments described herein, the dry egg replacement composition has one or more functional property of a natural egg. In some embodiments, the dry egg replacement composition has at least 2 functional properties of a natural egg. In some embodiments, the one or more functional property of a natural egg is selected from the group consisting of complete nutrition, protein digestibility-corrected amino acid score (PDCAAS), gelation, foaming, viscosity, emulsification, water binding capacity, texture, elasticity, springiness, solubility, flavor, coagulation, aeration, creaminess, film forming property, sheen addition, shine addition, freeze stability, thaw stability, color, and combinations thereof.

In certain embodiments, the gellan gum is in an amount of about 1 g to about 10 g, about 1.5 g to about 9 g, about 2 g to about 8 g, or about 4 g to about 6 g in the dry mixture. In certain embodiments, the gellan gum is in an amount of about 5.6 g in the dry mixture. In certain embodiments, the amount of gellan gum in the dry egg replacement composition is from about 0.5% to about 5%, about 1% to about 4%, or about 2% to about 3% of the dry mixture. In certain embodiments, the amount of gellan gum in the dry egg replacement composition is about 0.5%, about 1%, about 2%, about 3%, about 4%, or about 5% of the dry mixture. In certain embodiments, the amount of gellan gum in the dry egg replacement composition is about 3.5% of the dry mixture. Gellan gum is heat-activated and helps to retain the texture of the final egg product despite cooling after being cooked.

In certain embodiments, the methylcellulose is in an amount of about 1 g to about 12 g, about 2 g to about 10 g, about 3 g to about 9 g, or about 4 g to about 8 g in the dry mixture. In certain embodiments, the methylcellulose is in an amount of about 8.75 g in the dry mixture. In certain embodiments, the amount of methylcellulose in the dry egg replacement composition is from about 1% to about 10%, about 1% to about 9%, about 2% to about 8%, about 2% to about 7%, about 2% to about 6%, about 2% to about 9%, about 3% to about 8%, about 4% to about 7%, or about 5% to about 6% of the dry mixture. In certain embodiments, the amount of methylcellulose in the dry egg replacement composition is about 1%, about 1.5%, about 2%, about 2.5%, about 3%, about 3.5%, about 4%, about 4.5%, about 5%, about 5.5%, or about 6% of the dry mixture. In certain embodiments, the amount of methylcellulose in the dry egg replacement composition is about 5.5% of the dry mixture. Methylcellulose supports the structure of the food product at high temperatures and helps retain the texture and moisture of the food product.

In some embodiments, the protein digestibility-corrected amino acid score (PDCAAS) is a method of evaluating the quality of a protein based on both the amino acid requirements of humans and their ability to digest it. Using the PDCAAS method, the protein quality rankings are determined by comparing the amino acid profile of the specific food protein against a standard amino acid profile with the highest possible score being a 1.0. In some embodiments, the protein digestibility-corrected amino acid score (PDCAAS) of the dry egg replacement composition and/or the egg replacement emulsion and/or liquid egg and/or liquid egg formulation and/or egg replacement formulation described herein is 1.0.

In some embodiments, the functional property of gelation is measured by the temperature at which gelling occurs. In some embodiments, the dry egg replacement composition and/or the egg replacement emulsion and/or liquid egg and/or liquid egg formulation and/or egg replacement formulation described herein has a gelation onset below 90° C. Further, gel strength can be tested using a torsion test. An appropriately sized, and shaped gel is twisted in a rheometer until the gel either breaks, or it is ruptured. The amount of the force that caused the cross-section to rupture is then calculated and can be measured against other sensory results. The strength of a gel is affected by temperature, pH, and the amount of the protein derivative in the food product. The gel strength of the food product comprising protein flour, protein concentrate and/or protein isolate can be measured by a tensiometer. The gel strength can also be measured by a texture analyzer, such as TA.XT Express or TA.XTPlus (Texture Technologies), FTC Texture Analyzer (Food Technology Corporation), and LFRA texture analyzer (Brookfield Engineering), which through compression and tensile data, can measure a number of physical properties, including tensile strength, i.e. a measurement of the force required to pull the gelatinous or "gelled" food product to the point where it breaks. Texture analyzers also test the crunchiness, gumminess, adhesiveness, chewiness, and general texture of many smaller things from crackers to candy. Texture analyzers measure tensile strength (i.e. in lb/in$^2$ or psi) and compressive strength (i.e. psi or MPa) of materials. The principle of a texture measurement system is to physically deform a test sample in a controlled manner and measure its response. The characteristics of the force response are as a result of the sample's mechanical properties, which correlate to specific sensory texture attributes. A texture analyzer applies this principle by performing the procedure automatically and indicating the results visually on a digital numerical display, or screen.

In some embodiments, the functional property of foaming is measured by the ability of the composition to retain air in suspension. In some embodiments, the dry egg replacement composition and/or the egg replacement emulsion and/or liquid egg and/or liquid egg formulation and/or egg replacement formulation described herein can be sufficiently foamed. Foaming Capacity can be measured using the following formula:

$$FC = \text{volume after whipping (mL)} - \text{volume before whipping (mL)} \times 100$$

Volume before whipping (mL)

Foaming Stability can be measured using the following formula:

$$FS = \text{Foam volume at time } t \text{ (s)} \times 100$$

Initial foam volume (mL)

In some embodiments, the dry egg replacement composition and/or the egg replacement emulsion described herein can be used as an emulsifier. Emulsification Activity can be measured using the following formula:

$$EA = \text{Height of the emulsified layer (mm)} \times 100$$

Height of the total contents in the tube (mm)

Emulsion Stability can be measured using the following formula:

$$ES = \text{Height of emulsified layer after heating (mm)} \times 100$$

Height of total contents in the tube (mm)

In some embodiments, the dry egg replacement composition and/or the egg replacement emulsion and/or liquid egg and/or liquid egg formulation and/or egg replacement formulation described herein has water binding capacity. Water binding capacity can be measured using water absorption or water holding capacity. Water Absorption is tested by adding 10 mLs of water to 0.5 g of mixture in a 13-ml graduated plastic test tube. The mixture is sonicated for 30 s at an output setting of 5 to disperse the sample. The mixture is held at 24° C. for 30 min, and then centrifuged at 2000 rpm for 25 min. The volume of free water is measured and the retained water is computed and reported as ml of water (+/−0.1 ml) absorbed per g of mixture. Testing Water Holding Capacity can be measured using the following methods: 1) Centrifuge: rapidly rotating device applies centrifugal force to the components in order to force separation. As such, fluids of different densities become separated, as do liquids from solids. 2) Press Method: the water holding capacity of the composition is calculated based off of the weight of the substance after it has been pressed.

In some embodiments, the dry egg replacement composition and/or the egg replacement emulsion and/or liquid egg and/or liquid egg formulation and/or egg replacement formulation described herein has the texture or consistency of a natural egg. In some embodiments, the dry egg replacement composition and/or the egg replacement emulsion and/or liquid egg and/or liquid egg formulation and/or egg replacement formulation described herein has the viscosity of a natural egg. Consistency is the relative ability of a sample to flow. Viscosity is the measure of how hard it is to force a substance into motion, or flow. The texture or consistency can be measured using a texture or consistency analyzer.

Taste

In some embodiments, the dry egg replacement composition and/or the egg replacement emulsion and/or liquid egg and/or liquid egg formulation and/or egg replacement formulation described herein has the flavor of a natural egg. The development of the dry egg replacement composition has overcome the fishy, algae taste typically found when utilizing algal protein in egg substitutes or other food products. The dry egg replacement composition and/or the egg replacement emulsion and/or liquid egg and/or liquid egg formulation and/or egg replacement formulation described herein has a neutral, slight sulfury taste which corresponds to a natural egg unlike previous versions or commercially available products and/or a reduction of undesirable characteristics typically found with algal compositions, for example fishy smell, unpleasant smell, fishy taste, or unpleasant taste. The taste can be measured using chromatographic analysis and consumer testing.

The dry egg replacement composition and/or the egg replacement emulsion and/or liquid egg and/or liquid egg formulation and/or egg replacement formulation described herein has a unique combination of black salt and onion powder. In certain embodiments, the ratio of black salt to onion powder is about 30:70 to about 50:50.

In certain embodiments, the flavoring is in an amount of about 0.5 g to about 10 g, about 1 g to about 8 g, about 2 g to about 6 g, or about 3 g to about 5 g in the dry mixture. In certain embodiments, the flavoring is in an amount of about 4 g in the dry mixture. In certain embodiments, the amount of flavoring in the dry egg replacement composition is from about 0.05% to about 5%, about 0.1% to about 5%, about 0.5% to about 4.5%, about 1% to about 4%, about 1.5% to about 3.5%, or about 2% to about 3% of the dry mixture. In certain embodiments, the amount of flavoring in the dry egg replacement composition is about 0.05%, about 0.1%, about 0.5%, about 1%, about 1.5%, about 2%, about 2.5%, about 3% about 3.5%, about 4%, about 4.5%, or about 5%, of the dry mixture. In certain embodiments, the amount of flavoring in the dry egg replacement composition is about 4% of the dry mixture. In certain embodiments, the amount of flavoring in the egg replacement composition is about 1% of the dry mixture. In certain embodiments, the amount of flavoring in the dry egg replacement composition is about 0.1% to about 1% of the dry mixture.

In certain embodiments, the flavoring is selected from the group consisting of black salt, black pepper, Himalayan sea salt, salt, onion powder, minced onion, roasted garlic, mushroom powder, yeast extract, and combinations thereof.

In certain embodiments, the black salt is in an amount of about 0.5 g to about 10 g, about 1 g to about 8 g, about 2 g to about 6 g, or about 3 g to about 5 g in the dry mixture. In certain embodiments, the black salt is in an amount of about 2.45 g in the dry mixture. In certain embodiments, the amount of black salt in the dry egg replacement composition is about 1.5% of the dry mixture.

In certain embodiments, the onion powder is in an amount of about 0.5 g to about 10 g, about 1 g to about 8 g, about 2 g to about 6 g, or about 3 g to about 5 g in the dry mixture. In certain embodiments, the onion powder is in an amount of about 1.40 g in the dry mixture. In certain embodiments, the amount of onion powder in the dry egg replacement composition is about 1% of the dry mixture.

Color

The dry egg replacement composition and/or the egg replacement emulsion and/or liquid egg and/or liquid egg formulation and/or egg replacement formulation described herein is a similar color to the yolk of a natural egg. Accordingly, the dry egg replacement composition and/or the egg replacement emulsion and/or liquid egg and/or liquid egg formulation and/or egg replacement formulation described herein contains no added colors. The dry egg replacement composition and/or the egg replacement emulsion and/or liquid egg and/or liquid egg formulation and/or egg replacement formulation described herein has reduction or absence of undesirable characteristics typically found with algal compositions, for example green-color. Previous versions or commercially available products must utilize artificial coloring to achieve the natural yellow color. Color can be measured using colorimetric analyzer.

Stability

The dry egg replacement composition described herein has a shelf life which is longer than a natural egg at either room temperature, refrigerator temperature (about 2° C.), or freezer temperature (about −4° C.). In certain embodiments, the dry egg replacement composition contains no added preservatives. The dry egg replacement composition described herein has an enhanced shelf life at room temperature. In some embodiments, the shelf life at room temperature is greater than 3 months, greater than 4 months, greater than 5 months, greater than 6 months, greater than 7 months, greater than 8 months, greater than 9 months, greater than 10 months, greater than 11 months, or greater than 12 months. In some embodiments, the shelf life at room temperature is at least 6 months. The dry egg replacement composition described herein has an enhanced shelf life when stored in a refrigerator or freezer. In some embodiments, the shelf life when stored in a refrigerator or freezer is greater than 3 months, greater than 4 months, greater than 5 months, greater than 6 months, greater than 7 months, greater than 8 months, greater than 9 months, greater than 10 months, greater than 11 months, or greater than 12 months. In some embodiments, the shelf life when stored in a refrigerator or freezer is at least 6 months. In some embodiments, the dry egg replacement composition and/or the egg replacement emulsion and/or liquid egg and/or liquid egg formulation and/or egg replacement formulation described herein has the freeze stability and thaw stability of a natural egg.

Egg Replacement Emulsion

The egg replacement emulsion described herein has the consistency necessary to replace a natural egg in any food application. The egg replacement emulsion described herein has a property similar to a natural egg selected from the group consisting of emulsifying properties, viscosity, consistency, elasticity, springiness, solubility, coagulation, aeration, creaminess, film forming property, sheen addition, shine addition, and combinations thereof. Accordingly, the egg replacement emulsion described herein cooks in about the same time as a natural egg.

Embodiments described herein are directed to an egg replacement emulsion comprising a dry egg replacement composition, an oil, and water.

In certain embodiments, the dry egg replacement composition is about 5% to about 50%, about 10% to about 40%, about 15% to about 30%, or about 20% to about 25% of the egg replacement emulsion.

In embodiments described herein, the *Euglena*-derived material of the dry egg replacement composition can be selected from the group consisting of a *Euglena* biomass, a protein-rich flour derived from *Euglena*, a protein concentrate derived from *Euglena*, or a protein isolate derived from *Euglena*.

In certain embodiments, the dry egg replacement composition is in an amount of about 9 g to about 15 g, about 10 g to about 14 g, about 11 g to about 13 g, or about 12 g to about 12.5 g per serving size of the egg replacement emulsion. In certain embodiments, the dry egg replacement composition is in an amount of about 12.5 g per serving size of the egg replacement emulsion. In certain embodiments, the serving size of the egg replacement emulsion is from about 50 g to about 100 g, about 60 g to about 90 g, about 70 g to about 80 g, or about 80 g to about 90 g. In certain embodiments, the serving size of the egg replacement emulsion is from about 80 g to about 90 g.

In certain embodiments, the oil is about 5% to about 20%, about 8% to about 18%, about 10% to about 16%, or about 14% to about 14% of the egg replacement emulsion.

In certain embodiments, the amount of oil in the egg replacement emulsion is about 1 tablespoon to about 3 tablespoons. In some embodiments, the amount of oil used is about 1 tablespoon, about 2 tablespoons, or about 3 tablespoons. In some embodiments, the oil can be selected from the group consisting of vegetable oil, soybean oil, coconut oil, olive oil, peanut oil, fish oil, avocado oil, palm oil, flax oil, corn oil, cottonseed oil, canola oil, rapeseed oil, sunflower oil, safflower oil, sesame oil, grapeseed oil, safflower oil, rice bran oil, propionate, palm kernel oil, *cuphea* oil, camelina *sativa* oil, mustard seed oil, cashew nut oil, oat oil, lupine oil, kenaf oil, calendula oil, hemp oil, coffee oil, linseed oil, hazelnut oil, *euphorbia* oil, pumpkin seed oil, coriander oil, *camellia* oil, rice oil, tung oil tree oil, cocoa oil, copra oil, opium poppy oil, castor bean oil, pecan oil, jojoba oil, jatropha oil, macadamia oil, Brazil nut oil, *Euglena* derived oil and combinations thereof.

In certain embodiments, the water is about 0.05% to about 80%, about 60% to about 85%, about 65% to about 80%, or about 70% to about 75% of the egg replacement emulsion. In certain embodiments, the water is about 10% to about 50% of the egg replacement emulsion. In certain embodiments, the water is about 50% to about 80% of the egg replacement emulsion.

In certain embodiments, the amount of water in the egg replacement emulsion is about ¼ cup to about 1 cup of water. In some embodiments, the amount of water used is about ¼ cup, about ¼ cup, about ¼ cup, ⅔ cup, ¾ cup, or 1 cup.

In some embodiments, the egg replacement emulsion described herein has the emulsifying properties of a natural egg.

In some embodiments, the egg replacement emulsion described herein has the viscosity of a natural egg. Apparent Viscosity is measured using a digital viscometer, which would effectively deliver results related to mouth feel, how a product will react to temperature changes, as well as the spread ability of the product.

In some embodiments, the egg replacement emulsion described herein has the consistency of a natural egg.

In some embodiments, the egg replacement emulsion described herein has the elasticity of a natural egg. In some embodiments, the egg replacement emulsion described herein exhibits an elasticity of greater than 300 Pa.

In some embodiments, the egg replacement emulsion described herein has the springiness of a natural egg.

In some embodiments, the egg replacement emulsion described herein has the solubility of a natural egg. Solubility can be measured by protein analysis (using colorimetric or Kjeldahl) of the supernatant after the emulsion is centrifuged to remove insoluble components.

In some embodiments, the egg replacement emulsion described herein has the coagulation of a natural egg.

In some embodiments, the egg replacement emulsion described herein has the aeration of a natural egg.

In some embodiments, the egg replacement emulsion described herein has the creaminess of a natural egg.

In some embodiments, the egg replacement emulsion described herein has the film forming property of a natural egg.

In some embodiments, the egg replacement emulsion described herein has the sheen addition and shine addition of a natural egg.

Liquid Egg

The liquid egg described herein has the consistency necessary to replace a natural egg in any food application. The liquid egg described herein has a property similar to a natural egg selected from the group consisting of emulsifying properties, viscosity, consistency, elasticity, springiness, solubility, coagulation, aeration, creaminess, film forming property, sheen addition, shine addition, and combinations thereof. Accordingly, the liquid egg described herein cooks in about the same time as a natural egg.

Embodiments described herein are directed to a liquid egg comprising a dry egg replacement composition, an oil, and water.

In certain embodiments, the dry egg replacement composition is about 5% to about 50%, about 10% to about 40%, about 15% to about 30%, or about 20% to about 25% of the liquid egg.

In embodiments described herein, the *Euglena*-derived material is selected from the group consisting of a *Euglena* biomass, a *Euglena*-derived protein, a protein-rich flour derived from *Euglena*, a protein concentrate derived from *Euglena*, a protein isolate derived from *Euglena*, a *Euglena*-derived beta-glucan isolate, a *Euglena*-derived oil, and combinations thereof.

In certain embodiments, the dry egg replacement composition is in an amount of about 9 g to about 15 g, about 10 g to about 14 g, about 11 g to about 13 g, or about 12 g to about 12.5 g per serving size of the liquid egg. In certain embodiments, the dry egg replacement composition is in an amount of about 12.5 g per serving size of the liquid egg. In certain embodiments, the serving size of the liquid egg is from about 50 g to about 100 g, about 60 g to about 90 g, about 70 g to about 80 g, or about 80 g to about 90 g. In certain embodiments, the serving size of the liquid egg is from about 80 g to about 90 g.

In certain embodiments, the oil is about 5% to about 20%, about 8% to about 18%, about 10% to about 16%, or about 14% to about 14% of the liquid egg.

In certain embodiments, the amount of oil in the liquid egg is about 1 tablespoon to about 3 tablespoons. In some embodiments, the amount of oil used is about 1 tablespoon, about 2 tablespoons, or about 3 tablespoons. In some embodiments, the oil can be selected from the group consisting of vegetable oil, soybean oil, coconut oil, olive oil, peanut oil, fish oil, avocado oil, palm oil, flax oil, corn oil, cottonseed oil, canola oil, rapeseed oil, sunflower oil, safflower oil, sesame oil, grapeseed oil, safflower oil, rice bran oil, propionate, palm kernel oil, *cuphea* oil, camelina *sativa* oil, mustard seed oil, cashew nut oil, oat oil, lupine oil, kenaf oil, calendula oil, hemp oil, coffee oil, linseed oil, hazelnut oil, *euphorbia* oil, pumpkin seed oil, coriander oil, *camellia* oil, rice oil, tung oil tree oil, cocoa oil, copra oil, opium poppy oil, castor bean oil, pecan oil, jojoba oil, jatropha oil, macadamia oil, Brazil nut oil, *Euglena* derived oil and combinations thereof.

In certain embodiments, the water is about 0.05% to about 80%, about 60% to about 85%, about 65% to about 80%, or about 70% to about 75% of the liquid egg. In certain embodiments, the water is about 10% to about 50% of the liquid egg. In certain embodiments, the water is about 50% to about 80% of the liquid egg.

In certain embodiments, the amount of water in the liquid egg is about ¼ cup to about 1 cup of water. In some embodiments, the amount of water used is about ¼ cup, about ¼ cup, about ½ cup, ⅔ cup, ¾ cup, or 1 cup.

In some embodiments, the liquid egg described herein has the emulsifying properties of a natural egg.

In some embodiments, the liquid egg described herein has the viscosity of a natural egg. Apparent Viscosity is measured using a digital viscometer, which would effectively deliver results related to mouth feel, how a product will react to temperature changes, as well as the spread ability of the product.

In some embodiments, the liquid egg described herein has the consistency of a natural egg.

In some embodiments, the liquid egg described herein has the elasticity of a natural egg. In some embodiments, the liquid egg herein exhibits an elasticity of greater than 300 Pa.

In some embodiments, the liquid egg described herein has the springiness of a natural egg.

In some embodiments, the liquid egg described herein has the solubility of a natural egg. Solubility can be measured by protein analysis (using colorimetric or Kjeldahl) of the supernatant after the emulsion is centrifuged to remove insoluble components.

In some embodiments, the liquid egg described herein has the coagulation of a natural egg.

In some embodiments, the liquid egg described herein has the aeration of a natural egg.

In some embodiments, the liquid egg described herein has the creaminess of a natural egg.

In some embodiments, the liquid egg described herein has the film forming property of a natural egg.

In some embodiments, the liquid egg described herein has the sheen addition and shine addition of a natural egg.

Liquid Egg Using Fresh *Euglena*-Derived Material

The liquid egg described herein has the consistency necessary to replace a natural egg in any food application. The liquid egg described herein has a property similar to a natural egg selected from the group consisting of emulsifying properties, viscosity, consistency, elasticity, springiness, solubility, coagulation, aeration, creaminess, film forming property, sheen addition, shine addition, and combinations thereof. Accordingly, the liquid egg described herein cooks in about the same time as a natural egg.

Embodiments described herein are directed to a liquid egg formulation comprising about 50% to about 85% fresh *Euglena*-derived material, about 5% to about 10% pea protein, water, and one or more additional ingredient, wherein the liquid egg formulation comprises one or more functional property of a natural egg.

Embodiments described herein are directed to a liquid egg formulation comprising about 1% to about 100% fresh *Euglena*-derived material, about 0.05% to about 70% additional protein source, water, and one or more additional ingredient, wherein the liquid egg formulation comprises one or more functional property of a natural egg.

In some embodiments of the liquid egg formulation described herein, the additional protein source is selected from the group consisting of pea protein, soy protein, corn protein, wheat protein, rice protein, beans protein, seed protein, nut protein, almond protein, peanut protein, seitan protein, lentil protein, chickpea protein, flaxseed protein, wild rice protein, quorn protein, chia seed protein, *quinoa* protein, oat protein, fava bean protein, buckwheat protein, bulgar protein, millet protein, microalgae protein, yellow pea protein, mung bean protein, hemp protein, sunflower protein, canola protein, lupin protein, legumes protein, potato protein, and combinations thereof.

In some embodiments of the liquid egg formulation described herein, the additional protein source is in an amount of about 0.05% to about 70%, about 0.5% to about 70%, about 1% to about 70%, about 5% to about 70%, about 10% to about 70%, about 15% to about 70%, about 0.05% to about 60%, about 0.05% to about 50%, about 0.05% to about 40%, about 0.05% to about 30%, or about 0.05% to about 20%. In certain embodiments of the liquid egg formulation described herein, the additional protein source is in an amount of about 0.05% to about 15%. In certain embodiments of the liquid egg formulation described herein, the additional protein source is in an amount of about 20% to about 60%.

In some embodiments, the fresh *Euglena*-derived material is in an amount of about 5% to about 90%, about 50% to about 85%, about 50% to about 75%, about 50% to about 65%, about 60% to about 85%, or about 70% to about 85% in the liquid mixture. In certain embodiments, the fresh *Euglena*-derived material is in an amount of about 55% in the liquid mixture. In certain embodiments, the fresh *Euglena*-derived material is in an amount of about 62% in the liquid mixture. In certain embodiments, the fresh *Euglena*-derived material is in an amount of about 7% in the liquid mixture. In certain embodiments, the fresh *Euglena*-derived material is in an amount of about 40% to about 87% in the liquid mixture. In certain embodiments, the fresh *Euglena*-derived material is in an amount of about 40% to about 90% in the liquid mixture.

In some embodiments, the pea protein is in an amount of about 5% to about 10%, about 5% to about 15%, about 5% to about 20%, about 5% to about 25%, or about 7.5% to about 10% in the liquid mixture. In certain embodiments, the pea protein is in an amount of about 5.5% in the dry mixture. In certain embodiments, the pea protein is in an amount of about 6% in the dry mixture.

In some embodiments of the liquid egg formulation described herein, the fresh *Euglena*-derived material is selected from the group consisting of a fresh *Euglena* biomass, *Euglena*-derived protein, a protein-rich flour derived from *Euglena*, a protein concentrate derived from *Euglena*, a protein isolate derived from *Euglena*, *Euglena*-derived beta-glucan isolate, *Euglena*-derived oils, and combinations thereof.

In some embodiments of the liquid egg formulation described herein, the one or more additional ingredient is selected from the group consisting of gellan gum, methylcellulose, yeast extract, baking powder, sunflower lecithin, tranglutaminase, flavoring, and combinations thereof.

In some embodiments of the liquid egg formulation described herein, the one or more additional ingredient is selected from the group consisting of water, gellan gum, methylcellulose, yeast extract, flavoring, antioxidant blend, maskers, leavening agents, baking powder, baking soda, enzymes, transglutaminase, emulsifiers, lecithin, mono- and diglycerides, binders, carrot fiber, defatted linseed flour, and combinations thereof.

In some embodiments of the liquid egg formulation described herein, each of the one or more additional ingredient is in an amount of about 0.05% to about 5%, about 0.05% to about 4%, or about 0.05% to about 3%, or about 0.05% to about 2%. In certain embodiments of the liquid egg formulation described herein, each of the one or more additional ingredient is in an amount of about 0.1% to about 1%.

In some embodiments of the liquid egg formulation described herein, the liquid egg formulation further comprises an oil. In some embodiments, the oil can be selected from the group consisting of vegetable oil, soybean oil, coconut oil, olive oil, peanut oil, fish oil, avocado oil, palm oil, flax oil, corn oil, cottonseed oil, canola oil, rapeseed oil, sunflower oil, safflower oil, sesame oil, grapeseed oil, safflower oil, rice bran oil, propionate, palm kernel oil, *cuphea* oil, camelina *sativa* oil, mustard seed oil, cashew nut oil, oat oil, lupine oil, kenaf oil, calendula oil, hemp oil, coffee oil, linseed oil, hazelnut oil, *euphorbia* oil, pumpkin seed oil, coriander oil, *camellia* oil, rice oil, tung oil tree oil, cocoa oil, copra oil, opium poppy oil, castor bean oil, pecan oil, jojoba oil, jatropha oil, macadamia oil, Brazil nut oil, *Euglena* derived oil and combinations thereof.

In some embodiments of the liquid egg formulation described herein, the flavoring is selected from the group consisting of black salt, black pepper, Himalayan sea salt, salt, onion powder, minced onion, roasted garlic, mushroom powder, yeast extract, or a combination thereof. In some embodiments, the liquid egg formulation described herein the flavoring is black salt and onion powder.

In some embodiments of the liquid egg formulation described herein, the liquid egg formulation further comprises one or more hydrocolloids. In some embodiments each of the one or more hydrocolloids may be selected from the group consisting of locust bean gum, a guar gum, a konjac gum, a gellan gum, a high methoxy pectin, a low methoxy pectin, an Agar, a kappa carrageenan, an iota carrageenan, a lambda carrageenan, an alginate, a curdlan, a methyl cellulose, a carboxymethyl cellulose (CMC), a xanthan gum, a gum Arabic, a *Euglena* derived beta-glucan and combinations thereof.

In some embodiments of the liquid egg formulation described herein, each of the one or more hydrocolloids is in an amount of about 0.05% to about 8%, about 0.1% to about 8%, about 0.05% to about 7%, about 0.05% to about 6%, about 0.05% to about 5%, about 0.05% to about 4%, or about 0.05% to about 3%. In certain embodiments of the liquid egg formulation described herein, each of the one or more hydrocolloids is in an amount of about 0.1% to about 2%.

In some embodiments of the liquid egg formulation described herein, the liquid egg formulation contains at least 3.0 g of protein, at least 3.5 g of protein, at least 4.0 g of protein, at least 4.5 g of protein, at least 5.0 g of protein, at least 5.5 g of protein, at least 6.0 g of protein, at least 6.5 g of protein, at least 7.0 g of protein, at least 7.5 g of protein, at least 8.0 g of protein, at least 8.5 g of protein, or at least 9.0 g of protein. In certain embodiments of the liquid egg formulation described herein, the liquid egg formulation contains at least 5 g of protein. In certain embodiments of the liquid egg formulation described herein, the liquid egg formulation contains at least 7.5 g of protein.

In some embodiments, the liquid egg formulation has a ratio of fresh *Euglena*-derived material to pea protein of about 15:1 to about 5:1. In some embodiments, the liquid egg formulation has a ratio of fresh *Euglena*-derived material to pea protein of about 7.5:1 to about 5:1. In some embodiments the liquid egg formulation has a ratio of fresh *Euglena*-derived material to pea protein of about 15:1 to about 7.5:1. In certain embodiments the liquid egg formulation has a ratio of fresh *Euglena*-derived material to pea protein of about 10:1.

In some embodiments of the liquid egg formulation described herein, the water is in an amount of about 10% to about 35%, about 15% to about 35%, about 20% to about 35%, about 25% to about 35%, about 10% to about 30%, about 10% to about 25%, about 0.05% to about 80%, about 60% to about 85%, about 65% to about 80%, or about 70% to about 75% of the liquid egg formulation. In certain embodiments of the liquid egg formulation described herein, the water is in an amount of about 33% of the liquid egg formulation. In certain embodiments of the liquid egg formulation described herein, the water is in an amount of about 24% of the liquid egg formulation. In certain embodiments, the water is about 10% to about 50% of the liquid egg formulation. In certain embodiments, the water is about 50% to about 80% of the liquid egg formulation.

In some embodiments of the liquid egg formulation described herein, the oil is in an amount of about 2.5% to about 7.5%, about 3.0% to about 7.5%, about 3.5% to about 7.5%, about 4.0% to about 7.5%, about 4.5% to about 7.5%, about 2.5% to about 7.0%, about 2.5% to about 6.5%, about 2.5% to about 6.0%, or about 2.5% to about 5.5%. In certain embodiments of the liquid egg formulation described herein, the oil is in an amount of about 4.5%. In certain embodiments of the liquid egg formulation described herein, the oil is in an amount of about 5%. In certain embodiments of the liquid egg formulation described herein, the oil is in an amount of about 0.05% to about 10%. In certain embodiments of the liquid egg formulation described herein, the oil is in an amount of about 0.05% to about 20%.

In some embodiments of the liquid egg formulation described herein, the gellan gum is in an amount of 0.2% to about 1%, amount of 0.3% to about 1%, amount of 0.4% to about 1%, amount of 0.2% to about 0.9%, amount of 0.2% to about 0.8%, amount of 0.2% to about 0.7%, or amount of 0.2% to about 0.6%. In certain embodiments of the liquid egg formulation described herein, the gellan gum is in an amount of about 0.44%. In certain embodiments of the liquid egg formulation described herein, the gellan gum is in an amount of about 0.50%.

In some embodiments of the liquid egg formulation described herein, the methylcellulose is in an amount of about 0.5% to about 1%, about 0.6% to about 1%, about 0.5% to about 0.9%, or about 0.5% to about 0.8%. In certain embodiments of the liquid egg formulation described herein, the methylcellulose is in an amount of about 0.66%. In certain embodiments of the liquid egg formulation described herein, the methylcellulose is in an amount of about 0.77%.

In some embodiments of the liquid egg formulation described herein, the ratio of gellan gum to methyl cellulose is about 1:5, about 2:5, about 1:4, or about 1:3. In certain embodiments of the liquid egg formulation described herein, the ratio of gellan gum to methyl cellulose is about 2:3.

In some embodiments of the liquid egg formulation described herein, the yeast extract is in an amount of about 0.2% to about 0.5%, about 0.3% to about 0.5%, or about 0.2% to about 0.4%. In certain embodiments of the liquid egg formulation described herein, the yeast extract is in an amount of about 0.33%. In certain embodiments of the liquid egg formulation described herein, the yeast extract is in an amount of about 0.37%.

In some embodiments of the liquid egg formulation described herein, the baking powder is in an amount of about 0.1% to about 0.5%, about 0.2% to about 0.5%, about 0.1% to about 0.4%, or about 0.1% to about 0.3%. In certain embodiments of the liquid egg formulation described herein, the baking powder is in an amount of about 0.22%. In certain embodiments of the liquid egg formulation described herein, the baking powder is in an amount of about 0.25%.

In some embodiments of the liquid egg formulation described herein, the sunflower lecithin is in an amount of about 0.1% to about 0.5%, about 0.2% to about 0.5%, about 0.1% to about 0.4%, or about 0.1% to about 0.3%. In certain embodiments of the liquid egg formulation described herein, the sunflower lecithin is in an amount of about 0.29%.

In some embodiments of the liquid egg formulation described herein, the transglutaminase is in an amount of about 0.1% to about 0.5%, about 0.2% to about 0.5%, about 0.1% to about 0.4%, or about 0.1% to about 0.3%. In certain embodiments of the liquid egg formulation described herein, the transglutaminase is in an amount of about 0.25%.

In some embodiments of the liquid egg formulation described herein, the flavoring is in an amount of about 0.05% to about 0.5%, about 0.1% to about 0.5%, about 0.1% to about 0.4%, or about 0.1% to about 0.3%. In certain embodiments of the liquid egg formulation described herein, the flavoring is in an amount of about 0.3%. In certain embodiments of the liquid egg formulation described herein, the flavoring is in an amount of about 0.1% to about 1%.

In embodiments described herein, the liquid egg formulation has one or more functional property of a natural egg. In some embodiments, the liquid egg formulation has at least 2 functional properties of a natural egg. In some embodiments, the one or more functional property of a natural egg is selected from the group consisting of complete nutrition, protein digestibility-corrected amino acid score (PDCAAS), gelation, foaming, viscosity, emulsification, water binding capacity, texture, elasticity, springiness, solubility, flavor, coagulation, aeration, creaminess, film forming property, sheen addition, shine addition, freeze stability, thaw stability, color, and combinations thereof Liquid Egg Using *Euglena*-Derived Wet Protein Concentrate The liquid egg described herein has the consistency necessary to replace a natural egg in any food application. The liquid egg described herein has a property similar to a natural egg selected from the group consisting of emulsifying properties, viscosity, consistency, elasticity, springiness, solubility, coagulation, aeration, creaminess, film forming property, sheen addition, shine addition, and combinations thereof. Accordingly, the liquid egg described herein cooks in about the same time as a natural egg.

Embodiments described herein are directed to a liquid egg formulation comprising about 12% to about 95% *Euglena*-derived wet protein concentrate, about 1% to about 20% solid content, water, and one or more additional ingredient, wherein the liquid egg formulation comprises one or more functional property of a natural egg.

Embodiments described herein are directed to a liquid egg formulation comprising about 1% to about 100% *Euglena*-derived wet protein concentrate, about 1% to about 20% solid content, an additional protein source, water, and one or more additional ingredient, wherein the liquid egg formulation comprises one or more functional property of a natural egg.

In some embodiments of the liquid egg formulation described herein, the additional protein source is selected from the group consisting of pea protein, soy protein, corn protein, wheat protein, rice protein, beans protein, seed protein, nut protein, almond protein, peanut protein, seitan protein, lentil protein, chickpea protein, flaxseed protein, wild rice protein, quorn protein, chia seed protein, *quinoa* protein, oat protein, fava bean protein, buckwheat protein, bulgar protein, millet protein, microalgae protein, yellow pea protein, mung bean protein, hemp protein, sunflower protein, canola protein, lupin protein, legumes protein, potato protein, and combinations thereof.

In some embodiments of the liquid egg formulation described herein, the additional protein source is in an amount of about 0.05% to about 70%, about 0.5% to about 70%, about 1% to about 70%, about 5% to about 70%, about 10% to about 70%, about 15% to about 70%, about 0.05% to about 60%, about 0.05% to about 50%, about 0.05% to about 40%, about 0.05% to about 30%, or about 0.05% to about 20%. In certain embodiments of the liquid egg formulation described herein, the additional protein source is in an amount of about 0.05% to about 15%. In certain embodiments of the liquid egg formulation described herein, the additional protein source is in an amount of about 20% to about 60%.

In some embodiments, the *Euglena*-derived wet protein concentrate is in an amount of about 5% to about 90%, about 15% to about 95%, about 20% to about 95%, about 25% to about 95%, about 30% to about 95%, about 30% to about 95%, about 35% to about 95%, about 40% to about 95%, about 45% to about 95%, about 50% to about 95%, about 55% to about 95%, in the liquid mixture. In certain embodiments, the *Euglena*-derived wet protein concentrate is in an amount of about 94% in the liquid mixture. In certain embodiments, the *Euglena*-derived wet protein concentrate is in an amount of about 56% in the liquid mixture. In certain embodiments, the *Euglena*-derived wet protein concentrate is in an amount of about 7% in the liquid mixture. In certain embodiments, the *Euglena*-derived wet protein concentrate is in an amount of about 40% to about 87% in the liquid mixture. In certain embodiments, the *Euglena*-derived wet protein concentrate is in an amount of about 40% to about 90% in the liquid mixture.

In some embodiments of the liquid egg formulation described herein, the solid content is in an amount of about 1% to about 20%, about 2% to about 20%, about 3% to about 20%, about 4% to about 20%, about 5% to about 20%, about 1% to about 19%, about 1% to about 18%, about 1% to about 17%, about 1% to about 16%, or about 1% to about 15%. In certain embodiments of the liquid egg formulation described herein, the solid content is in an amount of about 5%. In certain embodiments of the liquid egg formulation described herein, the solid content is in an amount of about 15%.

In some embodiments, the *Euglena*-derived wet protein concentrate is an *Euglena*-derived protein isolate.

In some embodiments, the *Euglena*-derived wet protein concentrate is about 25% to about 80% protein, about 30% to about 80% protein, about 35% to about 80% protein, about 40% to about 80% protein, about 45% to about 80% protein, about 50% to about 80% protein, about 55% to about 80% protein, about 60% to about 80% protein, about 65% to about 80% protein, or about 25% to about 75% protein. In certain embodiments, the *Euglena*-derived wet protein concentrate is about 70% protein.

In some embodiments of the liquid egg formulation described herein, the one or more additional ingredient is selected from the group consisting of an oil, water, gellan gum, methylcellulose, yeast extract, baking powder, sunflower lecithin, flavoring, and combinations thereof.

In some embodiments of the liquid egg formulation described herein, the one or more additional ingredient is selected from the group consisting of gellan gum, methylcellulose, yeast extract, flavoring, antioxidant blend, maskers, leavening agents, baking powder, baking soda, enzymes, transglutaminase, emulsifiers, lecithin, mono- and diglycerides, binders, carrot fiber, defatted linseed flour, and combinations thereof.

In some embodiments of the liquid egg formulation described herein, each of the one or more additional ingredient is in an amount of about 0.05% to about 5%, about 0.05% to about 4%, or about 0.05% to about 3%, or about 0.05% to about 2%. In certain embodiments of the liquid egg formulation described herein, each of the one or more additional ingredient is in an amount of about 0.1% to about 1%.

In some embodiments of the liquid egg formulation described herein, the liquid egg formulation further comprises an oil. In some embodiments, the oil can be selected from the group consisting of vegetable oil, soybean oil, coconut oil, olive oil, peanut oil, fish oil, avocado oil, palm oil, flax oil, corn oil, cottonseed oil, canola oil, rapeseed oil, sunflower oil, safflower oil, sesame oil, grapeseed oil, safflower oil, rice bran oil, propionate, palm kernel oil, *cuphea* oil, camelina *sativa* oil, mustard seed oil, cashew nut oil, oat oil, lupine oil, kenaf oil, calendula oil, hemp oil, coffee oil, linseed oil, hazelnut oil, *euphorbia* oil, pumpkin seed oil, coriander oil, *camellia* oil, rice oil, tung oil tree oil, cocoa oil, copra oil, opium poppy oil, castor bean oil, pecan oil, jojoba oil, jatropha oil, macadamia oil, Brazil nut oil, *Euglena* derived oil and combinations thereof.

In some embodiments of the liquid egg formulation described herein, the flavoring is selected from the group consisting of black salt, black pepper, Himalayan sea salt, salt, onion powder, minced onion, roasted garlic, mushroom powder, yeast extract, or a combination thereof. In some embodiments, the liquid egg formulation described herein the flavoring is black salt and onion powder.

In some embodiments of the liquid egg formulation described herein, the liquid egg formulation further comprises one or more hydrocolloids. In some embodiments the one or more hydrocolloids may be selected from the group consisting of locust bean gum, a guar gum, a konjac gum, a gellan gum, a high methoxy pectin, a low methoxy pectin, an Agar, a kappa carrageenan, an iota carrageenan, a lambda carrageenan, an alginate, a curdlan, a methyl cellulose, a carboxymethyl cellulose (CMC), a xanthan gum, a gum Arabic, a *Euglena* derived beta-glucan and combinations thereof.

In some embodiments of the liquid egg formulation described herein, each of the one or more hydrocolloids is in an amount of about 0.05% to about 8%, about 0.1% to about 8%, about 0.05% to about 7%, about 0.05% to about 6%, about 0.05% to about 5%, about 0.05% to about 4%, or about 0.05% to about 3%. In certain embodiments of the liquid egg formulation described herein, each of the one or more hydrocolloids is in an amount of about 0.1% to about 2%.

In some embodiments of the liquid egg formulation described herein, the liquid egg formulation contains at least 3.0 g of protein, at least 3.5 g of protein, at least 4.0 g of protein, at least 4.5 g of protein, at least 5.0 g of protein, at least 5.5 g of protein, at least 6.0 g of protein, at least 6.5 g of protein, at least 7.0 g of protein, at least 7.5 g of protein, at least 8.0 g of protein, at least 8.5 g of protein, or at least 9.0 g of protein. In certain embodiments of the liquid egg formulation described herein, the liquid egg formulation contains at least 5.6 g of protein. In certain embodiments of the liquid egg formulation described herein, the liquid egg formulation contains at least 5 g of protein.

In some embodiments of the liquid egg formulation described herein, the ratio of *Euglena*-derived wet protein concentrate to solid content is about 95:1 to about 1.6:1, about 70:1 to about 1.6:1, about 45:1 to about 1.6:1, about 20:1 to about 1.6:1, about 10:1 to about 1.6:1, or about 5:1 to about 1.6:1. In certain embodiments of the liquid egg formulation described herein, the ratio of *Euglena*-derived wet protein concentrate to solid content is about 3.7:1.

In some embodiments of the liquid egg formulation described herein, the oil is in an amount of about 0.05% to about 20%, about 2.5% to about 7.5%, about 3.0% to about 7.5%, about 3.5% to about 7.5%, about 4.0% to about 7.5%, about 4.5% to about 7.5%, about 2.5% to about 7.0%, about 2.5% to about 6.5%, about 2.5% to about 6.0%, or about 2.5% to about 5.5%. In certain embodiments of the liquid egg formulation described herein, the oil is in an amount of about 5%. In certain embodiments of the liquid egg formulation described herein, the oil is in an amount of about 4.5%. In certain embodiments of the liquid egg formulation described herein, the oil is in an amount of about 0.05% to about 10%.

In some embodiments of the liquid egg formulation described herein, the water is in an amount of about 10% to about 50%, about 15% to about 50%, about 20% to about 50%, about 25% to about 50%, about 30% to about 50%, about 35% to about 50%, about 10% to about 45%, about 10% to about 40%, about 0.05% to about 80%, about 60% to about 85%, about 65% to about 80%, or about 70% to about 75% of the liquid egg formulation. In certain embodiments of the liquid egg formulation described herein, the water is in an amount of about 37% of the liquid egg formulation of the liquid egg formulation. In certain embodiments, the water is about 10% to about 50% of the liquid egg formulation. In certain embodiments, the water is about 50% to about 80% of the liquid egg formulation. In certain embodiments, the water is about 0.05% to about 80% of the liquid egg formulation.

In some embodiments of the liquid egg formulation described herein, the gellan gum is in an amount of 0.1% to about 1%, amount of 0.2% to about 1%, amount of 0.1% to about 0.9%, amount of 1% to about 0.8%, amount of 0.1% to about 0.7%, amount of 0.1% to about 0.6%, or amount of 0.1% to about 0.5%. In certain embodiments of the liquid egg formulation described herein, the gellan gum is in an amount of about 0.23%. In certain embodiments of the liquid egg formulation described herein, the gellan gum is in an amount of about 0.46%.

In some embodiments of the liquid egg formulation described herein, the methylcellulose is in an amount of about 0.1% to about 1.25%, about 0.2% to about 1.25%, about 0.3% to about 1.25%, about 0.1% to about 1%, about 0.1% to about 0.8%, or about 0.1% to about 0.8%. In certain embodiments of the liquid egg formulation described herein, the methylcellulose is in an amount of about 0.35%. In certain embodiments of the liquid egg formulation described herein, the methylcellulose is in an amount of about 0.83%.

In some embodiments of the liquid egg formulation described herein, the ratio of gellan gum to methyl cellulose is about 1:10, about 2:10, about 1:9, or about 2:9. In certain embodiments of the liquid egg formulation described herein, the ratio of gellan gum to methyl cellulose is about 2:3. In certain embodiments of the liquid egg formulation described herein, the ratio of gellan gum to methyl cellulose is about 5:9.

In some embodiments of the liquid egg formulation described herein, the yeast extract is in an amount of about 0.1% to about 0.5%, about 0.2% to about 0.5%, about 0.1% to about 0.4%, or about 0.1% to about 0.3%. In certain embodiments of the liquid egg formulation described herein, the yeast extract is in an amount of about 0.23%. In certain embodiments of the liquid egg formulation described herein, the yeast extract is in an amount of about 0.28%.

In some embodiments of the liquid egg formulation described herein, the baking powder is in an amount of about 0.1% to about 0.75%, about 0.2% to about 0.75%, about 0.1% to about 0.7%, 0.1% to about 0.6%, 0.1% to about 0.5%, or about 0.1% to about 0.4%. In certain embodiments of the liquid egg formulation described herein, the baking powder is in an amount of about 0.23%. In certain embodiments of the liquid egg formulation described herein, the baking powder is in an amount of about 0.46%.

In some embodiments of the liquid egg formulation described herein, the sunflower lecithin is in an amount of about 0.1% to about 0.5%, about 0.2% to about 0.5%, about 0.1% to about 0.4%, or about 0.1% to about 0.3%. In certain embodiments of the liquid egg formulation described herein, the sunflower lecithin is in an amount of about 0.23%. In certain embodiments of the liquid egg formulation described herein, the sunflower lecithin is in an amount of about 0.28%.

In some embodiments of the liquid egg formulation described herein, the flavoring is in an amount of about 0.05% to about 0.5%, about 0.05% to about 0.4%, about 0.1% to about 0.5%, about 0.15% to about 0.5%, or about 0.2% to about 0.5%. In certain embodiments of the liquid egg formulation described herein, the flavoring is in an amount of about 0.25%. In certain embodiments of the liquid egg formulation described herein, the flavoring is in an amount of about 0.46%. In certain embodiments of the liquid egg formulation described herein, the flavoring is in an amount of about 0.1% to about 1%.

In embodiments described herein, the liquid egg formulation has one or more functional property of a natural egg. In some embodiments, the liquid egg formulation has at least 2 functional properties of a natural egg. In some embodiments, the one or more functional property of a natural egg is selected from the group consisting of complete nutrition, protein digestibility-corrected amino acid score (PDCAAS), gelation, foaming, viscosity, emulsification, water binding capacity, texture, elasticity, springiness, solubility, flavor, coagulation, aeration, creaminess, film forming property, sheen addition, shine addition, freeze stability, thaw stability, color, and combinations thereof.

For the liquid egg formulations using fresh biomass or wet or powdered *Euglena* protein concentrate maskers are required to mask the marine flavours of *Euglena*. An ideal masker should completely mask the off notes (both aroma and flavour) coming from *Euglena* during cooking and in cooked products without introducing any new flavours or aroma. Flavours can also be used to improve the flavour of cooked liquid egg. Ideal flavour should provide a flavour that is similar to cooked real egg. Since the amount of *Euglena* is higher in protein concentrate a higher amount of masker/flavour will be required for protein concentrate based liquid egg formulations. In certain embodiments, the dry egg replacement, egg replacement emulsion, liquid egg, or liquid egg formulation described herein further comprise one or more maskers. In certain embodiments, the maskers can be purchased from Firmenich, IFF, Givaudan, Symrise, Mane, Fona, Flavor producer, McCormick, edlong, T•Hasegawa. Sensient Flavors, Robertet SA, Prova, Wild/ADM, Takasago, Synergy, and others.

Egg Replacement Formulation

The egg replacement formulation described herein has the consistency necessary to replace a natural egg in any food application. The liquid egg described herein has a property similar to a natural egg selected from the group consisting of emulsifying properties, viscosity, consistency, elasticity, springiness, solubility, coagulation, aeration, creaminess, film forming property, sheen addition, shine addition, and combinations thereof. Accordingly, the egg replacement formulation described herein cooks in about the same time as a natural egg.

Embodiments described herein are directed to an egg replacement formulation comprising about 1% to about 100% *Euglena*-derived material, about 0.05% to about 70% additional protein source, and one or more additional ingredient, wherein the egg replacement formulation comprises one or more functional property of a natural egg.

In some embodiments of the egg replacement formulation described herein, the *Euglena*-derived material is a dry material. In some embodiments of the egg replacement formulation described herein, the *Euglena*-derived material is a wet material.

In some embodiments of the egg replacement formulation described herein, the *Euglena*-derived material is selected from the group consisting of a fresh *Euglena* biomass, a *Euglena* biomass, a *Euglena*-derived protein, a protein-rich flour derived from *Euglena*, a protein concentrate derived from *Euglena*, a protein isolate derived from *Euglena*, a *Euglena*-derived beta-glucan isolate, a *Euglena*-derived oil, a *Euglena*-derived wet protein concentrate, a *Euglena*-derived protein isolate and combinations thereof.

In some embodiments of the egg replacement formulation described herein, the *Euglena*-derived material is in an amount of about 5% to about 90%, about 50% to about 85%, about 50% to about 75%, about 50% to about 65%, about 60% to about 85%, or about 70% to about 85% in the mixture. In certain embodiments, the *Euglena*-derived material is in an amount of about 55% in the mixture. In certain embodiments, the *Euglena*-derived material is in an amount of about 62% in the mixture. In certain embodiments, the *Euglena*-derived material is in an amount of about 7% in the mixture. In certain embodiments, the *Euglena*-derived material is in an amount of about 40% to about 87% in the mixture. In certain embodiments, the *Euglena*-derived material is in an amount of about 40% to about 90% in the mixture.

In some embodiments of the egg replacement formulation described herein, the additional protein source is selected from the group consisting of pea protein, soy protein, corn protein, wheat protein, rice protein, beans protein, seed protein, nut protein, almond protein, peanut protein, seitan protein, lentil protein, chickpea protein, flaxseed protein, wild rice protein, quorn protein, chia seed protein, *quinoa* protein, oat protein, fava bean protein, buckwheat protein, bulgar protein, millet protein, microalgae protein, yellow pea protein, mung bean protein, hemp protein, sunflower protein, canola protein, lupin protein, legumes protein, potato protein, and combinations thereof.

In some embodiments of the egg replacement formulation described herein, the additional protein source is in an amount of about 0.05% to about 70%, about 0.5% to about 70%, about 1% to about 70%, about 5% to about 70%, about 10% to about 70%, about 15% to about 70%, about 0.05% to about 60%, about 0.05% to about 50%, about 0.05% to about 40%, about 0.05% to about 30%, or about 0.05% to about 20%. In certain embodiments of the egg replacement formulation described herein, the additional protein source is in an amount of about 0.05% to about 15%. In certain embodiments of the egg replacement formulation described herein, the additional protein source is in an amount of about 20% to about 60%.

In some embodiments of the egg replacement formulation described herein, the one or more additional ingredient is selected from the group consisting of gellan gum, methylcellulose, yeast extract, flavoring, antioxidant blend, maskers, leavening agents, baking powder, baking soda, enzymes, transglutaminase, emulsifiers, lecithin, mono- and diglycerides, binders, carrot fiber, defatted linseed flour, and combinations thereof.

In some embodiments of the egg replacement formulation described herein, each of the one or more additional ingredient is in an amount of about 0.05% to about 5%, about 0.05% to about 4%, or about 0.05% to about 3%, or about 0.05% to about 2%. In certain embodiments of the egg replacement formulation described herein, each of the one or more additional ingredient is in an amount of about 0.1% to about 1%.

In some embodiments of the egg replacement formulation described herein, the egg replacement formulation further comprises an oil. In some embodiments, the oil can be selected from the group consisting of vegetable oil, soybean oil, coconut oil, olive oil, peanut oil, fish oil, avocado oil, palm oil, flax oil, corn oil, cottonseed oil, canola oil, rapeseed oil, sunflower oil, safflower oil, sesame oil, grapeseed oil, safflower oil, rice bran oil, propionate, palm kernel oil, *cuphea* oil, camelina *sativa* oil, mustard seed oil, cashew nut oil, oat oil, lupine oil, kenaf oil, calendula oil, hemp oil, coffee oil, linseed oil, hazelnut oil, *euphorbia* oil, pumpkin seed oil, coriander oil, *camellia* oil, rice oil, tung oil tree oil, cocoa oil, copra oil, opium poppy oil, castor bean oil, pecan oil, jojoba oil, jatropha oil, macadamia oil, Brazil nut oil, *Euglena* derived oil and combinations thereof.

In some embodiments of the egg replacement formulation described herein, the oil is in an amount of about 0.05% to about 20%, about 2.5% to about 7.5%, about 3.0% to about 7.5%, about 3.5% to about 7.5%, about 4.0% to about 7.5%, about 4.5% to about 7.5%, about 2.5% to about 7.0%, about 2.5% to about 6.5%, about 2.5% to about 6.0%, or about 2.5% to about 5.5%. In certain embodiments of the egg replacement formulation described herein, the oil is in an amount of about 5%. In certain embodiments of the egg replacement formulation described herein, the oil is in an amount of about 4.5%. In certain embodiments of the egg replacement formulation described herein, the oil is in an amount of about 0.05% to about 10%.

In some embodiments of the egg replacement formulation described herein, the egg replacement formulation further comprises one or more hydrocolloids. In some embodiments the one or more hydrocolloids may be selected from the group consisting of locust bean gum, a guar gum, a konjac gum, a gellan gum, a high methoxy pectin, a low methoxy pectin, an Agar, a kappa carrageenan, an iota carrageenan, a lambda carrageenan, an alginate, a curdlan, a methyl cellulose, a carboxymethyl cellulose (CMC), a xanthan gum, a gum Arabic, a *Euglena* derived beta-glucan and combinations thereof.

In some embodiments of the egg replacement formulation described herein, each of the one or more hydrocolloids is in an amount of about 0.05% to about 8%, about 0.1% to about 8%, about 0.05% to about 7%, about 0.05% to about 6%, about 0.05% to about 5%, about 0.05% to about 4%, or about 0.05% to about 3%. In certain embodiments of the egg replacement formulation described herein, each of the one or more hydrocolloids is in an amount of about 0.1% to about 2%.

In some embodiments of the egg replacement formulation described herein, the egg replacement formulation further comprises flavoring. In some embodiments the flavoring is selected from the group consisting of black salt, black pepper, Himalayan sea salt, salt, onion powder, minced onion, roasted garlic, mushroom powder, yeast extract, or a combination thereof. In some embodiments, the egg replacement formulation described herein the flavoring is black salt and onion powder.

In some embodiments of the egg replacement formulation described herein, the flavoring is in an amount of about 0.05% to about 0.5%, about 0.05% to about 0.4%, about 0.1% to about 0.5%, about 0.15% to about 0.5%, or about 0.2% to about 0.5%. In certain embodiments of the egg replacement formulation described herein, the flavoring is in an amount of about 0.25%. In certain embodiments of the egg replacement formulation described herein, the flavoring is in an amount of about 0.46%. In certain embodiments of the egg replacement formulation described herein, the flavoring is in an amount of about 0.1% to about 1%.

In some embodiments of the egg replacement formulation described herein, the egg replacement formulation further comprises water. In some embodiments of egg replacement formulation described herein, the water is in an amount of about 10% to about 50%, about 15% to about 50%, about 20% to about 50%, about 25% to about 50%, about 30% to about 50%, about 35% to about 50%, about 10% to about 45%, about 10% to about 40%, about 0.05% to about 80%, about 60% to about 85%, about 65% to about 80%, or about 70% to about 75% of the egg replacement formulation. In certain embodiments of the egg replacement formulation described herein, the water is in an amount of about 37% of the egg replacement formulation of the egg replacement formulation. In certain embodiments, the water is about 10% to about 50% of the egg replacement formulation. In certain embodiments, the water is about 50% to about 80% of the egg replacement formulation. In certain embodiments, the water is about 0.05% to about 80% of the egg replacement formulation.

Product Safety

In some embodiments, the dry egg replacement composition, egg replacement emulsion, liquid egg, liquid egg formulation, or egg replacement formulation described herein has improved product safety. In some embodiments, the improved product safety is from a reduction of microbial spoilage. In some embodiments the microbial spoilage is from bacteria, yeast, mold, or a combination thereof. In some embodiments the reduction of microbial spoilage is from pasteurization, storage pH, antimicrobial treatment, or a combination thereof.

In some embodiments, the pasteurization is carried out at a temperature of about 40° C., about 45° C., about 50° C., about 55° C., about 60° C., about 65° C., about 70° C., about 75° C., about 80° C., about 85° C., about 90° C., about 95° C., about 100° C., or a range between any two of these values.

In some embodiments, the pasteurization is carried out for about 10 min, about 15 min, about 20 min, about 25 min, about 30 min, about 35 min, about 40 min, about 45 min, about 50 min, about 55 min, about 60 min, or a range between any two of these values.

In some embodiments, the storage pH is about pH 2.5, about pH 3.0, about pH 3.5, about pH 4.0, about pH 4.5, about pH 5.0, about pH 5.5, about pH 6.0, about pH 6.5, about pH 7.0, about pH 7.5, about pH 8.0, or a range between any two of these values.

In some embodiments, the antimicrobial treatment is carried out with an antimicrobial agent.

In some embodiments, the antimicrobial agent is selected from the group consisting of nisin, calcium propionate, sodium benzoate, potassium sorbate, Bio Vontage 2662, organic acids, or a combination thereof Vegan-Egg Scramble Embodiments described herein are directed to methods of preparing a vegan-egg scramble comprising combining a dry egg replacement composition, an oil, and water.

In certain embodiments, the dry egg replacement composition is in an amount of about 5% to about 50%, about 10% to about 40%, about 15% to about 30%, or about 20% to about 25% in the vegan-egg scramble. In certain embodiments, the dry egg replacement composition is in an amount of about 9 g to about 15 g, about 10 g to about 14 g, about 11 g to about 13 g, or about 12 g to about 12.5 g in the vegan-egg scramble. In certain embodiments, the dry egg replacement composition is in an amount of about 12.5 g in the vegan-egg scramble.

In certain embodiments, the oil is in an amount of about 5% to about 20%, about 8% to about 18%, about 10% to about 16%, or about 14% to about 14% of the oil is used in the vegan-egg scramble. In certain embodiments, the oil is in an amount of about 1 tablespoon to about 3 tablespoons in the vegan-egg scramble. In some embodiments, the oil is in an amount of about 1 tablespoon, about 2 tablespoons, or about 3 tablespoons in the vegan-egg scramble. In some embodiments, the oil can be selected from the group consisting of vegetable oil, soybean oil, coconut oil, olive oil, peanut oil, fish oil, avocado oil, palm oil, flax oil, corn oil, cottonseed oil, canola oil, rapeseed oil, sunflower oil, safflower oil, sesame oil, grapeseed oil, safflower oil, rice bran oil, propionate, palm kernel oil, *cuphea* oil, camelina *sativa* oil, mustard seed oil, cashew nut oil, oat oil, lupine oil, kenaf oil, calendula oil, hemp oil, coffee oil, linseed oil, hazelnut oil, *euphorbia* oil, pumpkin seed oil, coriander oil, *camellia* oil, rice oil, tung oil tree oil, cocoa oil, copra oil, opium poppy oil, castor bean oil, pecan oil, jojoba oil, jatropha oil, macadamia oil, Brazil nut oil, *Euglena* derived oil and combinations thereof.

In certain embodiments, the water is in an amount of about 60% to about 85%, about 65% to about 80%, or about 70% to about 75% in the vegan-egg scramble. In certain embodiments, the water is in an amount of about ¼ cup to about 1 cup in the vegan-egg scramble. In some embodiments, the water is in an amount of about ¼ cup, about ¼ cup, about ¼ cup, ⅔ cup, ¾ cup, or 1 cup in the vegan-egg scramble.

In certain embodiments, the egg scramble is prepared by mixing the dry egg replacement composition with about 1 tablespoon to about 3 tablespoons of oil and about ¼ cup to about 1 cup of water. The solution is mixed thoroughly by shaking or stirring and poured into a preheated frying pan. The egg scramble is cooked for about 3 minutes to about 6 minutes while being broken up with a spatula. In some embodiments, the vegan-egg scramble is cooked for about 3 minutes, about 4 minutes, about 5 minutes, or about 6 minutes.

Egg Replacement in Food Products

Embodiments described herein are directed to food products comprising the dry egg replacement composition, egg replacement emulsion, liquid egg, liquid egg formulation, or egg replacement formulation described herein in place of natural eggs.

The food products disclosed herein are illustrative examples of what can be done with the egg replacement disclosed herein and that *Euglena* egg is a functional egg substitute that can replace natural/whole eggs in all applications by incorporating an *Euglena* egg substitute. In some embodiments, about 0.5 to about 1.5 dry egg replacement composition, egg replacement emulsion, liquid egg, or liquid egg formulation described herein can replace 1 natural chicken egg. In certain embodiments, about 1 dry egg replacement composition, egg replacement emulsion, liquid egg, or liquid egg formulation described herein can replace 1 natural chicken egg.

In some embodiments, an organoleptic property is attributed to the food product from the dry egg replacement composition, egg replacement emulsion, liquid egg, liquid egg formulation, or egg replacement formulation described herein, which is similar or equivalent to the organoleptic property provided by a natural egg. In some embodiments, the dry egg replacement composition, egg replacement emulsion, liquid egg, liquid egg formulation, or egg replacement formulation provides a flavor, an aroma, a sensory impression, or combinations thereof that is similar or equivalent to the flavor, aroma, or sensory impression of a reference food product.

The dry egg replacement composition, egg replacement emulsion, liquid egg, liquid egg formulation, or egg replacement formulation described herein may be incorporated into an egg scramble, an egg patty, an omelet, a quiche, frittata, egg-free cake, such as a chocolate cake, a pound cake, a yellow cake, an angel food cake, a cream cheese analog, a pasta dough, a pasta, a milk, an ice cream, a custard, a frozen dessert (e.g., a frozen dessert comprising ice cream), or a confection.

The dry egg replacement composition, egg replacement emulsion, liquid egg, liquid egg formulation, or egg replacement formulation described herein may be incorporated into meat as a meat binder/extender, i.e. it may be used to bind a grain like oats to extend ground beef in meatballs, structured meat pieces or meatloaf, or even commercial hamburgers.

The dry egg replacement composition, egg replacement emulsion, liquid egg, liquid egg formulation, or egg replacement formulation described herein may be used as a retort stabilizer in canning process for pasta and structured meat pieces in soup/Chile. It can be used in dog food to prevent break down and loss of texture during the retort cooking/canning process. Retorting is the in-container sterilization of food to render it shelf stable under normal non-refrigerated conditions (commercially sterile).

The dry egg replacement composition, egg replacement emulsion, liquid egg, liquid egg formulation, or egg replacement formulation described herein may be used to replace egg in Vegan mayonnaise as well as mayonnaise based salad dressings, also in Hollandaise sauce.

The dry egg replacement composition described herein may be used by Food service as a dry replacement for liquid egg in Omelet base, French toast coating, or any other food product utilizing dry egg.

The dry egg replacement composition, egg replacement emulsion, liquid egg, liquid egg formulation, or egg replacement formulation described herein may be used as part of a consumer "complete" Pancake and Waffle mixes, as well as in frozen pancakes and waffles commercially produced to protect the texture and freeze/thaw stability.

The dry egg replacement composition, egg replacement emulsion, liquid egg, liquid egg formulation, or egg replacement formulation described herein may be used in Yogurt and probiotic beverages.

The dry egg replacement composition, egg replacement emulsion, liquid egg, liquid egg formulation, or egg replacement formulation described herein may be used to produce non-egg "Egg crumbles" for use on salads and/or on salad bars.

The dry egg replacement composition, egg replacement emulsion, liquid egg, liquid egg formulation, or egg replacement formulation described herein may be used Vegan Christmas egg nog.

In embodiments described herein, the dry egg replacement composition, egg replacement emulsion, liquid egg, liquid egg formulation, or egg replacement formulation described herein has provided one or more functional properties to the food product when incorporated therein. The functional properties when incorporated into a food application are selected from the group consisting of crumb density, structure/texture, elasticity, springiness, coagulation, binding, moisturizing, mouthfeel, leavening, aeration/foaming, creaminess, and emulsification of the food product such as an egg.

Mouthfeel is a concept used in the testing and description of food products. Products made using the dry egg replacement composition, the egg replacement emulsion, liquid egg, or liquid egg formulation described herein can be assessed for mouthfeel. In some embodiments products, e.g., baked goods, made using dry egg replacement composition, the egg replacement emulsion, liquid egg, or liquid egg formulation described herein have mouthfeel that is similar to products made with natural eggs. In some embodiments the mouthfeel of the products made using the dry egg replacement composition, the egg replacement emulsion, liquid egg, or liquid egg formulation described herein is superior to the mouthfeel of previously known or attempted egg substitutes, e.g., bananas, modified whey proteins, or Egg Beaters™. Examples of properties which may be included in a measure of mouthfeel include:

Cohesiveness: Degree to which the sample deforms before rupturing when biting with molars;

Density: Compactness of cross section of the sample after biting completely through with the molars;

Dryness: Degree to which the sample feels dry in the mouth;

Fracturability: Force with which the sample crumbles, cracks or shatters.

Fracturability encompasses crumbliness, crispiness, crunchiness and brittleness;

Graininess: Degree to which a sample contains small grainy particles, may be seen as the opposite of smoothness;

Gumminess: Energy required to disintegrate a semi-solid food to a state ready for swallowing;

Hardness: Force required to deform the product to given distance, i.e., force to compress between molars, bite through with incisors, compress between tongue and palate;

Heaviness: Weight of product perceived when first placed on tongue;

Moisture absorption: Amount of saliva absorbed by product; Moisture release: Amount of wetness/juiciness released from sample;

Mouthcoating: Type and degree of coating in the mouth after mastication (for example, fat/oil);

Roughness: Degree of abrasiveness of product's surface perceived by the tongue;

Slipperiness: Degree to which the product slides over the tongue;

Smoothness: Absence of any particles, lumps, bumps, etc., in the product;

Uniformity: Degree to which the sample is even throughout; homogeneity; Uniformity of Bite: Evenness of force through bite;

Uniformity of Chew: Degree to which the chewing characteristics of the product are even throughout mastication;

Viscosity: Force required to draw a liquid from a spoon over the tongue; and

Wetness: Amount of moisture perceived on product's surface.

Baked Cakes: In another aspect, provided herein are one or more egg-free cake mixes, suitable for preparing one or more egg-free cake batters, from which one or more egg-free cakes can be made. In some embodiments, the egg-free cake mix comprises flour, sugar, and the dry egg replacement composition, the egg replacement emulsion, liquid egg, or liquid egg formulation described herein. In some embodiments, the egg-free cake mix further comprises one or more additional components selected from: cream of tartar, disodium phosphate, baking soda, and a pH stabilizing agent. In some embodiments, the flour comprises cake flour. Also provided herein is an egg-free cake batter comprising an egg-free cake mix described above, and water. In some embodiments, the egg-free cake batter is an egg-free pound cake batter, an egg-free angel food cake batter, or an egg-free yellow cake batter. In some embodiments, the egg-free cake batter has a specific gravity of 0.95-0.99. In some embodiments, a peak height of the egg-free cake is at least 90% of a peak height of a pound cake containing eggs. In some embodiments, one or more characteristics of the egg-free cake is similar or equivalent to one or more corresponding characteristics of a cake containing eggs. In some embodiments, the one or more characteristics comprise resilience, cohesiveness, springiness, peak height, center doming, center crack, browning, mouthfeel, spring-back, or flavor. In some embodiments, the one or more characteristics comprise hardness, resilience, cohesiveness, springiness, or chewiness. In some embodiments, the one or more characteristics comprise a functional property or an organoleptic property. In some embodiments, the functional property comprises one or more of: emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color.

In a particular embodiment, provided herein is an egg-free pound cake mix, comprising flour, sugar, and the dry egg replacement composition, the egg replacement emulsion, liquid egg, or liquid egg formulation described herein. In some embodiments, the flour comprises cake flour. In some embodiments, the egg-free pound cake mix further comprises oil or fat. In some embodiments, the oil or fat comprises butter or shortening. In some embodiments, at least or about 25-31% of the egg-free pound cake batter is flour. In some embodiments, at least or about 25-31% of the egg-free pound cake batter is oil or fat. In some embodiments, at least or about 25-31% of the egg-free pound cake batter is sugar. In some embodiments, at least or about 6-12% of the egg-free pound cake batter is the dry egg replacement composition, the egg replacement emulsion, liquid egg, or liquid egg formulation described herein. In some embodiments, the batter further comprises disodium phosphate or baking soda.

Also provided herein is an egg-free pound cake batter comprising an egg-free pound cake mix described above, and further comprising water. In some embodiments, the egg-free pound cake batter comprises about four parts of the egg-free pound cake mix; and about one part water. In some embodiments, at least or about 20-25% of the egg-free pound cake batter is flour. In some embodiments, at least or about 20-25% of the egg-free pound cake batter is oil or fat. In some embodiments, at least or about 20-25% of the egg-free pound cake batter is sugar. In some embodiments, at least or about 5-8% of the egg-free pound cake batter is the dry egg replacement composition, the egg replacement emulsion, liquid egg, or liquid egg formulation described herein. In some embodiments, at least or about 18-20% of the egg-free pound cake batter is water.

In another particular embodiment, provided herein is an egg-free angel food cake mix comprising flour, sugar, and the dry egg replacement composition, the egg replacement emulsion, liquid egg, or liquid egg formulation described herein. In some embodiments, at least or about 8-16% of the egg-free angel food cake mix is flour. In some embodiments, at least or about 29-42% of the egg-free angel food cake mix is sugar. In some embodiments, at least or about 7-10% of the egg-free angel food cake mix is the dry egg replacement composition, the egg replacement emulsion, liquid egg, or liquid egg formulation described herein. In some embodiments, the egg-free angel food cake mix further comprises cream of tartar, disodium phosphate, baking soda, or a pH stabilizing agent. In some embodiments, the flour comprises cake flour. Also provided herein is an egg-free angel food cake batter comprising an egg-free angel food cake mix described above, and water.

In another particular embodiment, provided herein is an egg-free yellow cake mix, comprising flour, sugar, and the dry egg replacement composition, the egg replacement emulsion, liquid egg, or liquid egg formulation described herein. In some embodiments, at least or about 20-33% of the egg-free yellow cake mix is flour. In some embodiments, at least or about 19-39% of the egg-free yellow cake mix is sugar. In some embodiments, at least or about 4-7% of the egg-free yellow cake mix is the dry egg replacement composition, the egg replacement emulsion, liquid egg, or liquid egg formulation described herein. In some embodiments, the egg-free yellow cake mix further comprises one or more of baking powder, salt, dry milk, and shortening. Also provided herein is an egg-free yellow cake batter comprising an egg-free yellow cake mix described above, and water.

Some embodiments provide methods to produce an egg-free pound cake using a dry egg replacement composition, the egg replacement emulsion, liquid egg, or liquid egg formulation described herein. For instance, a batter is created by mixing liquid solution comprising the dry egg replacement composition, the egg replacement emulsion, liquid egg, or liquid egg formulation described herein with sugar, cake flour, and butter at 17° C. to 20° C. in 1:1:1:1 w/w ratio. The ingredients are blended together using single stage mixing on mixer for 6 minutes at 22° C. The batter is baked in pound cake pan for 45 minutes in 150° C. and cooled in pan for 2 hours at 22° C. Sensory quality parameters of cakes made with the dry egg replacement composition, the egg replacement emulsion, liquid egg, or liquid egg formulation described herein are characterized as fluffy, soft, airy texture. The peak height was measured to be 90-110% of pound cake containing eggs.

Cream Cheese Analog: In another aspect, provided herein is an egg-free cream cheese comprising the dry egg replacement composition, the egg replacement emulsion, liquid egg, or liquid egg formulation described herein. In some embodiments, the egg-free cream cheese comprises one or more additional components selected from water, oil or fat, and hydrocolloid. In some embodiments, at least or about 75-85% of the egg-free cream cheese is water. In some embodiments, at least or about 10-15% of the egg-free cream cheese is the dry egg replacement composition, the egg replacement emulsion, liquid egg, or liquid egg formulation described herein. In some embodiments, at least or about 5-10% of the egg-free cream cheese is oil or fat. In some embodiments, at least or about 0.1-3% of the egg-free cream cheese is hydrocolloid. In some embodiments, the hydrocolloid comprises xanthan gum or a low-methoxy pectin and calcium chloride system. In some embodiments, the egg-free cream cheese further comprises a flavoring or salt. In some embodiments, one or more characteristics of the egg-free cream cheese is similar or equivalent to one or more corresponding characteristics of a cream cheese containing eggs. In some embodiments, the characteristic is a taste, a viscosity, a creaminess, a consistency, a smell, a spreadability, a color, a thermal stability, or a melting property. In some embodiments, the characteristic comprises a functional property or an organoleptic property. In some embodiments, the functional property comprises: emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color. In some embodiments, the organoleptic property comprises a flavor or an odor.

Egg-free pasta dough: In another aspect, provided herein is an egg-free pasta dough comprising the dry egg replacement composition, the egg replacement emulsion, liquid egg, or liquid egg formulation described herein. In some embodiments, the egg-free pasta dough comprises one or more additional components selected from flour, oil or fat, and water. In some embodiments, the flour comprises semolina flour. In some embodiments, the oil or fat comprises extra virgin oil. In some embodiments, the egg-free pasta dough further comprises salt. Also provided herein is an egg-free pasta made from an egg-free pasta dough described above. In some embodiments, the egg-free pasta is fresh. In some embodiments, the egg-free pasta is dried. In some embodiments, one or more characteristics of the egg-free pasta is similar or equivalent to one or more corresponding characteristics of a pasta containing eggs. In some embodiments, the one or more characteristics comprise chewiness, density, taste, cooking time, shelf life, cohesiveness, or stickiness. In some embodiments, the one or more characteristics comprise a functional property or an organoleptic property. In some embodiments, the functional property comprises: emulsification, water binding capacity, foaming, gelation, crumb density, structure forming, texture building, cohesion, adhesion, elasticity, springiness, solubility, viscosity, fat absorption, flavor binding, coagulation, leavening, aeration, creaminess, film forming property, sheen addition, shine addition, freeze stability, thaw stability, or color. In some embodiments, the organoleptic property comprises a flavor or an odor.

Egg-free custard: In another aspect, provided herein is an egg-free custard comprising the dry egg replacement composition, the egg replacement emulsion, liquid egg, or liquid egg formulation described herein. In some embodiments, the egg-free custard comprises one or more additional components selected from cream and sugar. In some embodiments, at least or about 5% of the egg-free custard is the dry egg replacement composition, the egg replacement emulsion, liquid egg, or liquid egg formulation described herein. In some embodiments, at least or about 81% of the egg-free custard is cream. In some embodiments, at least or about 13% of the egg-free custard is sugar. In some embodiments, the egg-free custard further comprises one or more of: iota-carrageenan, kappa-carrageenan, vanilla, and salt. In some embodiments, the cream is heavy cream.

Egg-free ice cream: In another aspect, provided herein is an egg-free ice cream comprising the dry egg replacement composition, the egg replacement emulsion, liquid egg, or liquid egg formulation described herein. In some embodiments, the egg-free ice cream is a soft-serve ice cream or a regular ice cream. In some embodiments, the egg-free ice cream comprises one or more additional components selected from cream, milk, and sugar. In some embodiments, at least or about 5% of the egg-free ice cream is the dry egg replacement composition, the egg replacement emulsion, liquid egg, or liquid egg formulation described herein. In some embodiments, at least or about 41% of the egg-free ice cream is cream. In some embodiments, at least or about 40% of the egg-free ice cream is milk. In some embodiments, at least or about 13% of the egg-free ice cream is sugar. In some embodiments, the egg-free ice cream further comprises one or more of iota carrageenan, kappa carrageenan, vanilla, and salt. In some embodiments, the cream is heavy cream. In some embodiments, the milk is whole milk. In particular embodiments, the egg-free ice cream is lactose-free. In other particular embodiments, the egg-free ice cream does not comprise gums or stabilizers. In other embodiments, the egg-free ice provides a traditional mouthfeel and texture of an egg-based ice cream but melts at a slower rate relative to an egg-based ice cream.

EXAMPLES

Example 1: Egg Replacer with *Euglena* Protein Flour, Beta-Glucan Isolate, and Ready-to-Gel Powder In the market, there are 2 different egg replacement products strategies one is targeted for bakery applications. In that application, the main ingredients are starches and gums (used as binders and texturizers) accompanied by leavening agents to make up for egg white's leavening functionality in baking applications, along with some protein.

The other application for an egg replacer is a powder or liquid egg replacer that can scramble, for use as scrambled eggs, frittatas, or omelets. For the scramble egg replacer, the main ingredients will include a plant protein (for mimicking the nutrition of the real egg), and a mixture of different gums/hydrocolloids as binder and texture developers upon cooking.

In this study, a combination of pea protein concentrate and *Euglena* protein flour was used as the main protein source. Beta-glucan ready to gel (RTG) powder was used as the sole hydrocolloid source to act as a binder/texturizer. Beta-glucan RTG powder is solubilized beta-glucan in 1 M NaOH, that has been formed into a gel with 3.75% citric acid, and then freeze dried to form a powder. When the powder is put back into water, it readily forms a thickened solution or gel, depending on the concentration. The addition of beta-glucan isolate in combination with the *Euglena* protein flour gives the egg scramble the expected yellow colour of a scrambled egg, meaning that a coloring agent is not needed in these applications. In addition, the addition of the beta-glucan isolate also showed a masking effect on the *Euglena* protein flour off-notes compared to control mixture without the beta-glucan isolate. The *Euglena* flour is yellow which also adds to the expected yellow colour of scrambled eggs.

No flavoring agent or flavor masker has been used in this formulation and still panelists could perceive an umami-like taste which would be attributed to the protein sources (combination of *Euglena* flour and pea protein).

Methods and Materials: The formulation that was used in this study for an egg scramble is written in Table 1 which included the *Euglena* protein flour at approximately 30% protein in the flour, beta-glucan isolate from *Euglena*, as well as ready to gel beta-glucan powder to act as the hydrocolloid source. The dry ingredients are mixed together, then water is added and mixed. The mixture is whisked for 1 minute. To test the scramble like properties, the whisked mixture is poured into a frying pan that has been set to medium heat (approximately 170° C.) and with 1 tablespoon of warmed oil (i.e. vegetable, 1 tablespoon per 100 grams of liquid egg replacer). The whisked mixture is fried for about 7 to 9 minutes with a scrambling action every minute to two minutes to obtain a scrambled egg consistency. The mixture was analyzed by an internal taste panel.

TABLE 1

Formulation of egg (scramble) replacer

| Egg Replacer Formulation | % (Wet basis) | % (Dry basis) |
|---|---|---|
| Water | 87.8 | 0.0 |
| *Euglena* Protein Flour* | 4.0 | 32.8 |
| Pea Protein Concentrate (80% protein content) | 3.0 | 24.6 |
| Beta-glucan isolate powder | 1.0 | 8.2 |
| Ready to gel beta-glucan powder | 4.0 | 32.8 |
| Salt | 0.2 | 1.6 |
| Total | 100.0 | |
| % Total Solid | 12.2 | |

*Euglena* protein Flour Spec: Protein: 35.63% Oil: 13.4% Carbs: 38.69%

Results and Discussion: The *Euglena* based liquid scramble egg replacer had a yellow colour (FIG. 1). In this case, no flavouring agent or other known flavour masker was added in this formulation. As such in this formulation, the taste panelist could detect an umami-like taste which is due to the protein sources of the *Euglena* protein flour and the pea protein. Onion powder or salt, garlic powder or salt, and/or nutritional yeast powder could be a flavouring agent added to improve the taste of the *Euglena* liquid egg replacer.

For an improvement in taste the formulation of Table 2 was developed, which includes onion powder as well as salt.

TABLE 2

Taste improvement Formulation

| Ingredients | % (Wet basis/As is) |
|---|---|
| Water | 83.00 |
| *Euglena* Flour * | 7.00 |
| Puris Pea Protein (P870-80% Protein) | 9.50 |
| Salt | 0.10 |
| Gellan Gum Powder | 0.10 |
| Onion powder | 0.30 |
| Total | 100.00 |
| Total Solid | 17.00 |

TABLE 2-continued

Taste improvement Formulation

| Ingredients | % (Wet basis/As is) |
|---|---|
| *Euglena* Flour Spec | |
| Protein | 36.70 |
| Oil | 7.00 |
| Carb | 40.90 |

Example 2: Additional Studies on Liquid Egg Replacer

In this study, the effect of gellan gum as a hydrocolloid texturizer/binder, onion powder as a flavouring agent, and a higher protein enriched *Euglena* flour was investigated.

Materials and Methods: *Euglena* liquid egg replacer is seen in Table 3. For the *Euglena* protein flour, a flour with 37% protein and 48% protein was investigated to determine the effects of higher protein inclusion flour. In this formulation, no beta-glucan isolate as a masker/whitening agent was used. As well, no RTG beta-glucan powder was used as a hydrocolloid. Instead, the hydrocolloid gellan gum was added. A flavouring agent of onion powder is also added to improve taste of the final product.

To form the mixture, all dry ingredients were mixed, including the gellan gum followed by water addition and mixing. The mixture was heated to 80° C. for 1 hour, up to 2 hours for the gellan gum to hydrate and gel. The mixture is poured into a frying pan that has been set to medium heat (approximately 170° C.) with 1 tablespoon of warmed oil (i.e. vegetable, 1 tablespoon per 100 grams of liquid egg replacer). The mixture is fried for about 7 to 9 minutes with a scrambling action every minute to two minutes to obtain a scrambled egg consistency. The mixture was analyzed by an internal taste panel. The experiment was repeated again to confirm results.

TABLE 3

Ingredient list of *Euglena* liquid egg replacer.

| Ingredients | % (Wet basis) |
|---|---|
| Water | 85.42 |
| *Euglena* Protein Flour (37% or 48%) | 8.00 |
| Pea Protein Concentrate (80%) | 6.00 |
| Salt | 0.10 |
| Gellan Gum Powder | 0.18 |
| Onion Powder | 0.30 |
| Total | 100.00 |

Results and discussion: While after 1 hour heat treatment of the lower *Euglena* protein flour egg prototype (37% protein content), the presence of the gellan gum creates a thickened gel like consistency that resembles liquid egg and helps with the desired texture of scrambled egg upon cooking. In the prototype with higher *Euglena* protein content (47%) under the same heat treatment condition for 1 hour and even after about 2 hours, the expected gel-like thickened consistency was not obtained and the mixture was almost at the same consistency as before heat treatment or just subtly thicker, too thin and watery for cooking. This effect was observed in both replicates of the experiment.

Conclusion: Without wishing to be bound by theory, the result observed herein utilized a higher concentration of protein in the flour, accordingly the interaction between the protein and gellan gum prevented the gum from hydrating. This means the protein-gum interaction prevented the water-gum interaction from forming, preventing the hydration of the gum and its thickening/gelling effect in the matrix.

In an attempt to remedy the defects of the previous formulation, the ratio of pea protein to *Euglena*-derived protein was modified, see Table 4.

TABLE 4

Formulation containing greater ratio of pea to *Euglena*-derived protein

| Ingredient Name | Grams | Ingredient % |
|---|---|---|
| Pea Protein (Puris P870) | 12.00 | 48.98 |
| *Euglena* Protein Flour | 8.00 | 32.65 |
| Gellan Gum(Gellan HS) Lot: 35863 | 0.80 | 3.27 |
| Methylcellulose (HV Powder) | 1.25 | 5.10 |
| Sea Salt | 0.35 | 1.43 |
| Onion Powder (Organic) | 0.20 | 0.82 |
| Fona Egg Type Flavor, Nat 943.0135U (Lot#S1124684) | 1.00 | 4.08 |
| Fona Egg Type Flavor, Nat 943.0136U (Lot#S1924685) | 0.50 | 2.04 |
| Brewers nutritional yeast | 0.20 | 0.82 |
| Dadex LTR-DRY NGM | 0.20 | 0.82 |
| Total | 24.50 | 100.00 |

Example 3: Improved Aroma Tests

Figure 2:
FIG. 2 represents an intermediate prototype of the development of the egg replacement.

If achieve a more pleasant aroma, sea salt was replaced with black salt according to Table 5, and a vegan egg scramble with black salt is show in FIG. 2.

TABLE 5

Improved Aroma Formula

| Ingredient Name | Grams | Ingredient % | Target bottle formula 25 gr. |
|---|---|---|---|
| Pea Protein (Puris P870) | 12.00 | 52.17 | 13.043 |
| *Euglena* Protein Flour | 8.00 | 34.78 | 8.696 |
| Ticagel Gellan HS: Gellan Gum (Lot: 44186) | 0.80 | 3.48 | 0.870 |
| TICACEL HV Powder: Methylcellulose (Lot#38149) | 1.25 | 5.43 | 1.359 |
| Black salt | 0.35 | 1.52 | 0.380 |
| P512 yeast extract | 0.20 | 0.87 | 0.217 |
| Onion Powder (Organic) | 0.20 | 0.87 | 0.217 |
| Antioxidant Dadex ® LTR Dry NGM | 0.20 | 0.87 | 0.217 |
| Total | 23.00 | 100.00 | 25.000 |

Example 4: Egg Replacement Development Tests

Studies were performed to develop an egg substitute which would provide greater than 6 g protein, a PDCAAS of 1, a natural yellow color, a consistency and texture that could be easily used by the consumer as an egg scramble or added to recipes to replace eggs. The hurdles to overcome through these studies included the amount of total protein in the composition, low viscosity upon addition of water, the flavor was not neutral, and the color was too dark.

During the process of finalizing the current recipe numerous ingredients have been adjusted; flour combination/ratios, gums used and quantities, flavour profiles, and different salt used.

The quantities of flour; both pea protein and protein-rich *Euglena* flour have been adjusted. The current formula contains a 60:40 ratio of pea to *Euglena* flour blend. Other ratios have been experimented with; 70:30, 65:35. Only to find that the undesirable notes of the pea protein start to show through; most notably a powdery mouthfeel and pea protein flavour notes. Over the last 5 months we had been using the protein rich flour and using it as the primary flour to formulate with. However, during the last round of sensory testing it was found to have gone rancid and new protein rich flour was used to replace it. The new flours are processed differently and have a different flavour profile, most notable it is lighter on the *Euglena* off notes making it an ideal candidate for the vegan egg.

During the different trials for the vegan egg/egg replacement different gums were explored and tested to try and get the right egg like texture.

Gums used: 1) Konjac—derived from the konjac root. Which in nature forms one of the strongest gels. 2) Konjac+Xanthan gum: Known to work synergistically together. 3) Locus bean gum+Xanthan gum: works well together to produce good mouth feel. However, the strength of the gel in the vegan egg/egg replacement application did not work because of the thermal reversibility. 4) Xanthan gum: in order to utilize Xanthan gum it must be properly hydrated. Usage within the powdered vegan egg/egg replacement does not allow for such hydration. 5) Gellan gum HA: Forms soft elastic and non brittle gel that are thermal stable. 6) Methylcellulose gum: Is widely used in vegetarian products to give form to plant based proteins. And gels at a high temperature to an egg like texture but the thermal reversibility causes it to revert back to a weak gel. It works well in conjunction with gellan gum in keeping the desired egg like texture. During the gum experiments it was found that the combination between Methylcellulose gum and gellan gum not only combated the reversibility of the methylcellulose gum as it began to cool but worked with it to add a springy egg like quality.

Flavours: During the first trial run at the formula used (Table 4 above) egg type flavourings from Fona, sea salt and brewers yeast. The Brewers Yeast was a last minute substitution added in replace of the P512 yeast because of shipping issues. The brewers yeast substitution removed the umami flavour of the P512 changing the flavour profile. It was found that the combination of the egg type flavours in conjunction with the sea salt created very unpleasant odors during the cooking process. With testing and substitution it was decided to omit the Fona flavours and salt, and formulate to one of the original prototypes with black salt and yeast extract (Table 5 above). The removal of the Fona egg type flavours were substituted with Black salt because of the sulphuric quality reminiscent of egg. It is used in many vegan egg like recipes to mimic the aroma and flavor of egg.

Conclusion: After several different testing with the base formula it was ultimately decided to go with the current formula (Table 6 below) for a few reasons. Omitting the Fona egg type flavours reduced the off cooking aromas as well as reduced the ingredients within the formula creating a "cleaner" label. The addition of black salt mimics the egg like flavour. The decision to use the yeast extract P512 instead of the brewers nutritional yeast is mainly for the unique umami flavour. The brewers yeast did have a neutral flavour it did not lend itself to the unique flavouring of the vegan egg/egg replacement to help set it apart from the competitors.

The texture of the vegan egg/egg replacement plays one of the most important roles in creating the egg like texture. This texture is in large due to the combination of gums used. Methylcellulose gum is derived from cellulose and is therefore a renewable resource and has a long standing reputation of being safe to use. Gellan gum works synergistically with methylcellulose gum to prevent the melting of the gel when it begins to cool.

Future efforts will focus on masking any algae off notes and optimizing the egg like flavour. Possible masking applications would be spray drying maskers directly onto the *Euglena* biomass flour. This may also help for future applications of the egg to be used in not only savoury applications but also sweet baking goods.

Will start with a deconstructed egg, reducing it to the bare basic ingredients of flours and gels then adding one flavour at a time to thoroughly explore the importance of each flavour and optimize the inclusion. This could also create a more neutral "egg" which could be used in a wide variety of applications. Or creating a savoury or sweet specific "egg" for the particular needs of each application.

Texture, current formulation is good, could be improved and perhaps incorporate more natural sounding and easy to pronounce gels to appease the consumers desire for clean label foods. For Instance Konjac gel is derived from the konjac root and forms one of the strongest gels from a naturally derived plant. And work towards reducing the percent inclusion of the gels added to the egg without compromising texture.

While *Euglena* protein provides strong gelation and functional properties, the formulation of Table 6 utilizes a blend of pea protein isolate (>75% protein), protein rich *Euglena* flour, in combination with methycellulose and gellan gum that are heat activated at cook temperature. The combination of hydrocolliods, i.e. methycellulose and gellan gum, along with optimized ratio of pea protein/*Euglena* flour provides a viscosity of rehydrated vegan egg batter that is comparable to liquid eggs. Heat activation of functional hydrocolloids with optimized moisture/lipid ratio facilitates shortened cook time while delivery vegan egg texture similar to scrambled egg prepared from liquid chicken whole egg. Natural Yellow/orange color of *Euglena* eliminates the need of any added color. This composition also uses black salt, onion, yeast extract to help deliver sulfur and umami notes associated with liquid scrambled egg while providing consumer an option to using their oil of choice when rehydrating the dry mixture.

Figure 3:
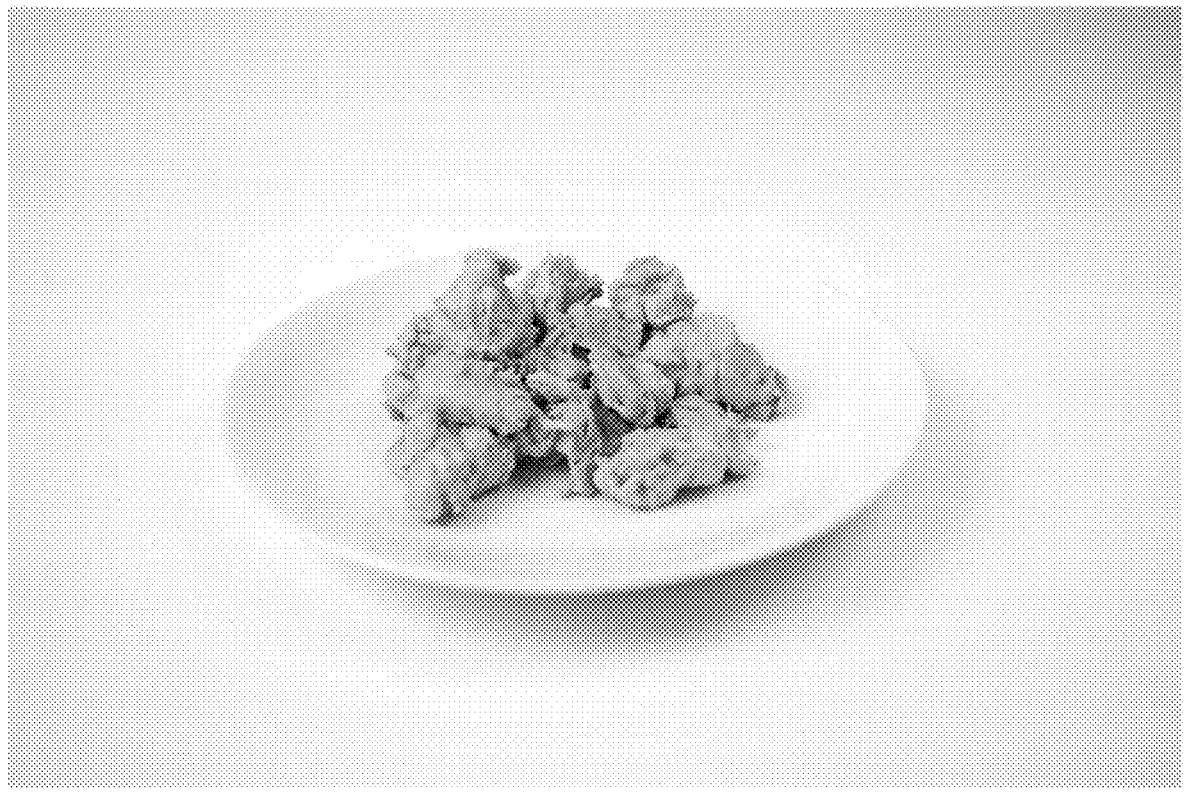
FIG. 3 shows the egg replacement described herein prepared as an egg scramble having the consistency, color, taste and nutritional profile of a natural egg.

The ratio of *Euglena* protein and pea protein resulted in greater than 6 g/50 g of an equivalent egg serving, this ratio also provided a natural yellow egg color. The combination of methylcellulose and gellan gum improved the texture and reduced the cook time to about 4-5 minutes when used as an egg scramble. The final combination of ingredients resulted in the optimal viscosity upon hydration of the dry egg substitute. The use of black salt, onion powder, yeast extract improved the egg flavor. See FIG. 3.

The final composition is provided in Table 6.

TABLE 6

Egg Replacement Composition

| Ingredient | Grams | % wt |
|---|---|---|
| Pea Protein | 84.00 | 52.18% |
| *Euglena* Protein Flour | 56.00 | 34.78% |
| Gellan gum | 5.60 | 3.48% |

TABLE 6-continued

Egg Replacement Composition

| Ingredient | Grams | % wt |
| --- | --- | --- |
| Methylcellulose | 8.75 | 5.43% |
| Black salt | 2.45 | 1.52% |
| Onion powder | 1.40 | 0.87% |
| Yeast extract | 1.40 | 0.87% |
| Dadex ® LTR Dry NGM or antioxidant blend | 1.40 | 0.87% |
| Total | 161.00 | 100.00% |

The preparation of an egg scramble utilizing the describe egg replacement includes mixing the dry ingredients described in Table 3 with 1 tablespoon of vegetable oil and ⅔ a cup of water. Shake well and pour into a preheated frying pan. Cook for 4 minutes, breaking up the mixture with a spatula.

Example 5: Spinach and Sun-Dried Tomato Scramble

The following is an example of the egg replacer as a scramble. Table 7 below shows amounts and ingredients used in the Spinach and Sun-Dried Tomato Scramble:

TABLE 7

Ingredients for Spinach and Sun-Dried Tomato Scramble with egg replacer ("The Egg")

| Ingredient: | Amount: |
| --- | --- |
| Baby Spinach | 1 cup |
| Garlic, Minced | 1 clove |
| Onion, Minced | 2 tbsp |
| Sun-dried tomatoes, minced | 1 tbsp |
| egg replacer ("The Egg"), unprepared | 2 scoops/1 bottle |

Directions: HEAT a drizzle of oil in a small skillet over medium heat. Stir in onion, cook until softened, about 2-3 minutes. Add spinach to skillet and cook for 2-3 minutes, or until spinach has wilted and liquid has evaporated. Stir in garlic and sun-dried tomatoes, cook for 1 minute. Remove mixture to a paper towel lined plate and wipe pan clean.

WHISK (or prepare in bottle) egg replacer ("The Egg") with 140 ml of water and 1 tbsp of oil in a medium bowl until smooth. Increase skillet heat to medium-high, and drizzle in 1 tsp of oil.

POUR egg replacer ("The Egg") into preheated skillet and cook, without stirring, for 45 seconds. Continue to cook egg replacer ("The Egg") for 4-5 minutes, using a rubber spatula to push egg around the pan. Add spinach mixture back to pan and cook for 1 minute or until heated through.

ENJOY as is, or in a wrap or on a slice of your favorite toasted bread. For a Mediterranean twist add a little feta to the scramble. Just crumble in 2 tbsps of feta over egg replacer ("The Egg") during the last minute of cooking. Placing the cooked spinach mixture on a paper towel lined plate will soak up any extra liquid from the spinach, keeping your scramble light and fluffy.

Example 6: Fluffy Oatmeal Cinnamon Pancakes

The following is an example of the egg replacer in a pancake. Table 8 below shows amounts and ingredients used in the Fluffy Oatmeal Cinnamon Pancakes:

TABLE 8

Ingredients for Fluffy Oatmeal Cinnamon Pancakes with egg replacer ("The Egg")

| Ingredient: | Amount: |
| --- | --- |
| Old fashioned rolled oats | 1 cup |
| All-purpose flour, or gluten free baking flour | ¾ cup |
| Baking Powder | 1 tbsp |
| Ground Cinnamon | 1 tsp |
| Cold milk or non-dairy alternative | 1 cup |
| egg replacer ("The Egg"), unprepared | 2 scoops/bottle |
| Cider Vinegar | 1 tsp |
| Maple syrup, or favorite liquid sweetener | 1 tbsp |
| Melted butter, or oil | 1 tbsp |
| Vanilla Extract | 1 tsp |

Directions: COMBINE oats, flour, baking powder and cinnamon in a large bowl and mix well. WHISK together milk, egg replacer ("The Egg") and vinegar in a medium bowl, let stand for 5 minutes. Add melted butter, maple syrup, and vanilla to the bowl with the milk and whisk until smooth. WHISK wet ingredients into the bowl with the dry ingredients until batter is smooth and lump free.

HEAT and grease a large skillet over medium heat. Pour about ¼ cup of pancake batter into skillet, gently press batter into a 4 inch circle. Cook for 1 to 2 minutes or until slightly dry around the sides and little bubbles appear, flip and continue cooking until both sides are lightly golden. Repeat with remaining batter, adding additional butter or oil in between batches as needed. SERVE pancakes with extra maple syrup and fresh berries.

Example 7: Caramelized Onion and Mushroom Strata

The following is an example of the egg replacer as used in a layered casserole dish. Table 9 below shows amounts and ingredients used in the Caramelized Onion and Mushroom Strata:

TABLE 9

Ingredients for Caramelized Onion and Mushroom Strata with egg replacer ("The Egg")

| Ingredient: | Amount: |
| --- | --- |
| 1 inch, cubed, day old sourdough bread | 10 cups |
| Grated old cheddar cheese (optional) | 1 cup |
| Spanish onion, finely sliced | 1 |
| Sliced, mixed mushrooms (portabella, cremini, shitaki) | 4 cups |
| Rosemary, minced | 1 tsp |
| Thyme, minced | 1 tsp |
| Cloves of garlic, minced | 2 |
| Whole Milk (3.25% fat) | 1½ cup |
| Dijon Mustard | 2 tsp |
| egg replacer ("The Egg") (unprepared) | 6 scoops/3 bottles |

Directions: PREHEAT your oven to 375° F. and grease a 9×13 baking dish. Place bread and cheese in a large bowl. HEAT 1 tbsp of oil in a large skillet over medium-low heat. Add onions to skillet and cook, stirring occasionally for 30 minutes, or until onions are tender and golden.

DRIZZLE a small amount of oil into the pan with the onions and increase the skillet heat to medium-high. Stir in mushrooms, rosemary and thyme, season with salt and pepper. Cook for 8 to 10 minutes, stirring occasionally, until golden and tender. Add garlic to skillet and cook for 1 minute. Transfer mixture to the bowl with the bread.

WHISK together milk. mustard, The Egg and ⅓ cup of cold water in a medium bowl until smooth. FOLD the wet ingredients into the bowl with the bread and mushroom mixture, mix until all the liquid is absorbed. Transfer to prepared baking dish and cover with aluminum foil.

PLACE strata in preheated oven and bake for 30 minutes. Remove foil and continue to bake for an additional 20 minutes, or until strata is firm and golden. REST strata for 10 minutes then serve with a side salad or fresh fruit. Make it vegan by using an unsweetened non dairy creamer and omitting the cheese.

Example 8: Vegan Chocolate Cake with Berry Filling and Chocolate Ganache

The following is an example of the egg replacer as used in a baked cake. Table 10 below shows amounts and ingredients used in the Vegan Chocolate Cake with Berry Filling and Chocolate Ganache:

TABLE 10

| Ingredients for Vegan Chocolate Cake with Berry Filling and Chocolate Ganache with egg replacer ("The Egg") | |
| --- | --- |
| Ingredient: | Amount: |
| FOR THE CAKE: | |
| Sugar | 2 cups |
| All purpose flour | 1¾ cups |
| Cocoa powder | 1 cup |
| Baking soda | 2 tsp |
| Baking Powder | 1 tsp |
| Salt | ½ tsp |
| Milk, dairy alternative | 1 cup |
| Vegetable Oil | ½ cup |
| egg replacer ("The Egg"), unprepared | 2 scoops/1 bottle |
| Pure vanilla extract | 2 tsp |
| Strong hot coffee, or hot water | 1 cup |
| FOR THE BERRY COMPOTE: | |
| Mixed berries, fresh or frozen | 2½ cups |
| Sugar | ½ cup |
| Fresh Lemon | 1 tbsp |
| Lemon Zest | 1 tsp |
| FOR THE CHOCOLATE GANACHE | |
| Vegan dark chocolate, roughly chopped | 12 oz |
| Coconut Cream | ½ cup |

Directions for the Cake: PREHEAT your oven to 350° F. Grease and line two 8 inch round cake pans with parchment paper. PLACE sugar in a large bowl, sift in flour, cocoa powder, baking soda, baking powder and salt, whisk until combined. WHISK together the milk, oil, The Egg and vanilla in a medium bowl until smooth. ADD wet ingredients to dry ingredients. Beat with a hand mixer until combined. Slowly add the coffee to the batter and beat on low speed, scraping down sides of bowl, until smooth. The stronger the coffee, the stronger the chocolate flavour. Divide batter evenly between prepared cake pans. TRANSFER to the preheated oven. Bake for 30 to 35 minutes or until an inserted toothpick comes out with little crumbs on it. COOL cake for 10 minutes, then gently run a knife around cake edges and invert onto a cooling rack, cool completely.

Directions for the Berry Compote: BRING berries and sugar to a boil in a small pot over medium high heat. Once boiling reduce the heat to medium and simmer for 15 to 20 minutes or until thickened. Remove from heat and transfer to a bowl. Stir in the lemon juice and zest, cool completely Directions for the Chocolate Ganache: MELT the chocolate in a double boiler or in a heatproof bowl set over a pot of barely simmering water, stirring occasionally. Once the chocolate is melted whisk in the coconut cream until combined. REMOVE from heat and allow to cool to an icing like consistency.

Directions to finish the cake: PLACE a cake round on a cake decorating wheel or serving plate. Mix together 1 cup of ganache with the cooled berry compote. Spread evenly over the top of the first cake round. Top with remaining cake round. DOLLOP ganache on top of the cake. Gently spread it evenly around the top and sides of the cake. Smooth with an offset spatula. GARNISH with fresh berries and mint.

Example 9: Breakfast Burritos with Avocado Pico de Gallo

The following is an example of the egg replacer as used in a breakfast burrito. Table 11 below shows amounts and ingredients used in the Breakfast Burritos with Avocado Pico de Gallo.

TABLE 11

| Ingredients for Breakfast Burritos with Avocado Pico de Gallo with egg replacer ("The Egg") | |
| --- | --- |
| Ingredient: | Amount: |
| BREAKFAST BURRITO: | |
| Red bell pepper, chopped | ¼ cup |
| Red onion, chopped | 2 tbsp |
| Baby Spinach | 1 cup |
| Tex-Mex Spice mix | 1 tsp |
| egg replacer ("The Egg"), unprepared | 4 scoops/2 bottles |
| Black beans, drained and rinsed | ¼ cup |
| 10 inch Whole Wheat Tortillas | 2 |
| Shredded cheddar cheese (Optional) | ¼ cup |
| AVACADO PICO de Gallo: | |
| Plum Tomatoes, seeded and diced | 1 |
| Avocado | ½ |
| Cilantro, chopped | 1 tbsp |
| Red onion, minced | 1 tbsp |
| Clove of garlic, minced | 1 |
| Fresh lime juice | 1 tsp |

Directions: HEAT a drizzle of oil in a medium skillet over medium heat. Add the bell pepper and onion, cook for 2-3 minutes, or until tender. Stir in spinach and cook until wilted and any extra liquid has evaporated, about 2 minutes. Stir in spice mix and cook for 30 seconds. Wipe skillet clean and increase heat to medium-high.

WHISK (or prepare in bottles) egg replacer ("The Egg") with 280 ml of water and 1 tbsp of oil until smooth. Pour into preheated pan and cook without stirring for 45 seconds. Continue to cook for 7 to 8 minutes using a rubber spatula to push egg around the pan. WHILE the egg cooks; in a small bowl mix together all pico de gallo ingredients, season with a little salt and pepper.

DIVIDE the cooked egg between 2 tortillas. Top with a sprinkle of shredded cheese and a spoonful of pico de gallo. FOLD up wrap and serve alongside any extra pico de gallo.

Example 10: Mini Frittatas 3 Ways

The following is an example of the egg replacer in a frittata. Table 12 below shows amounts and ingredients used in the Mini Frittatas, 3 different ways:

TABLE 12

Ingredients for Mini Frittatas, 3 different ways with egg replacer ("The Egg")

| Ingredient: | Amount: |
|---|---|
| EGG BASE: | |
| Milk or Dairy alternative | 1¼ cup |
| egg replacer ("The Egg"), unprepared | 8 scoops/4 bottles |
| Oil | 2 tbsp |
| Dijon Mustard | 1 tbsp |
| MUSHROOM AND SPINACH | |
| Spinach, chopped | 2 cups |
| Mushrooms, chopped | 1 cup |
| Clove of garlic, minced | 1 |
| HERB AND SUN-DRIED TOMATO | |
| Sun-dried tomatoes, chopped | ½ cup |
| Dried Italian Spice mix | 1 tsp |
| BROCCOL AND CHEDDAR | |
| Broccoli Florets (½ inch pieces) | 1 cup |
| Cheddar Cheese, shredded | ½ cup |

Directions for the Mushroom and Spinach Filling: HEAT a drizzle of oil in a large skillet over medium heat, add chopped mushrooms and cook for 3-8 minutes or until tender and golden. Stir in spinach and cook for 1-2 minutes or until wilted and excess moisture has evaporated. Stir in garlic and season with salt and pepper, cook for 1 minute. Remove from heat and let cool slightly.

Directions for Assembling the Frittata: PREHEAT your oven to 400° F. and grease a 12 cup muffin tin. WHISK together milk, 1 cup of cold water, The Egg, oil, and mustard in a large bowl until smooth (if you are making the Herb and Sun-dried tomato Frittatas, whisk Italian spice blend into egg mixture). FILL each muffin tin 2□3rds full. Evenly divide your chosen filling among muffin cups, pressing filling in slightly.

BAKE for 14 to 16 minutes, or until set. Run a knife along the edges of each frittata and then gently scoop out and serve. They are best enjoyed while hot, but can be frozen for easy breakfast prep. Remove frozen frittatas from the freezer and microwave on power level 5 for 2-3 minutes or until heated through and fluffy.

Example 11: Additional Uses for the Egg Replacement Described Herein

Egg Variations will include the universal egg replacement, an egg replacement specific for baking which would not contain savory flavours added, the seasoned egg replacement (i.e. Tex mex, Italian, Mediterranean, Cajun, Other unique and trendy seasoning if market research shows a market for it).

May also include dehydrated vegetables for a "shake, pour and cook vegetable scramble egg."

Commercial Uses will include replacement of chicken eggs in high volume bakeries, "non perishable eggs for camping," offering a vegan egg alternative with a long shelf like for Restaurant use, use in Noodles.

Recipes will include: Eggless Pasta Dough, Egg Fried Rice with Spiced Chickpeas, Cinnamon Buns with Maple Glaze, Vegetable Pad Thai, Indian Style Pancakes with Spicy Ginger Tomato Jam, Mini Chocolate Doughnuts, Okonomiyaki (Japanese Pancakes), Cardamom Spiced Sugar Cookies, Shakshuka, eggs poached in spiced tomato sauce, Savoury Egg and Cheese Crepes, Vegetable Carbonara, Breakfast Pizza with Pesto, vegetables and Scrambled Egg, Huevos Rancheros, Egg Drop Soup, Breakfast Tostadas, Belgian Waffles with Coconut Whip, Bhurji Egg, Asparagus and Chive Quiche, Sautéed Vegetable and Pesto Gnocchi, Mini Green Onion and Gruyere Souffle, and Mayonnaise.

Example 12: Liquid Egg Formulation Using Fresh Biomass and Pea Protein Isolate Introduction Demand for high quality protein alternatives for animal protein gained significant attention lately for food, pharmaceutical, nutraceutical, cosmetic and other industrial applications. Proteins obtained from a wide variety of sources, including the proteins obtained from oil seeds, pulses, and other plant-based proteins have been used as an alternative for animal proteins. Lately, microorganisms such as micro algae, yeast, etc., have been considered as a potential source of second-generation plant proteins. Several prominent food industries are looking forward to leveraging microorganisms to deliver sustainable high-quality proteins. According to Business Wire, the total algae protein market will grow to a market size of US$0.838 by 2023, which was only US$0.596 in 2018.

Recently, *Euglena gracilis* has emerged as an interesting candidate for application-driven research and commercialization, as it is an excellent source of high-quality dietary protein, pro(vitamins), lipids, and the β-1,3-glucan paramylon. It as well as its natural ability to tolerate a number of external stresses, including acidic growth conditions and ionising radiation, and has been shown to be capable of heavy metal sequestration. Controlled growth of *Euglena* in different media can be used to achieve high quality proteins, carbohydrates and lipids for value added food application.

Development of diary, meat and egg analogues using alternative protein are gaining more attention in the current society due to increasing global population and dietary restrictions. Eggs are the most commonly used ingredient worldwide and developing an alternative for eggs with the same nutritional value as the real egg is critical for future food security and malnutrition prevention. Currently available egg replacement in the market lacks nutritional value of the real egg. Furthermore, the quality of the protein present in the plant-based egg alternative is not as good as real egg protein as most of the plant proteins are incomplete since they lack some of the required essential amino acids. Therefore, egg alternative development using *Euglena* based protein, which is a complete protein, has huge potential.

An egg alternative formulation was already developed by Noblegen Inc. using *Euglena* protein rich flour, which has similar nutritional and functional properties as that of real egg. However, the current cost associated with the dry egg production using *Euglena* protein rich flour was high due to the involvement of spray drying of *Euglena* biomass to produce *Euglena* protein rich flour. Also, the existing formulation has used pea protein to meet the amount of required protein per serving (>6 g protein per serving). The objective of the present study was therefore to formulate liquid egg using fresh *Euglena* biomass with pea protein or wet fresh *Euglena* protein concentrate without any pea protein with more than 6 g of protein per serving and a reasonable cooking time with high quality, safety and shelf life. Several attempts and experimentations were conducted to formulate a high quality, good tasting egg using fresh *Euglena* biomass and wet *Euglena* protein concentrate, which will be explained below in detail.

Objective

The main objective of this study was to formulate liquid egg using *Euglena* fresh biomass grown in different media (protein rich or carbohydrate rich media) with different protein, carbohydrate and lipid content with more than 6 g protein per serving and less than 4.5 minute cooking time. Fresh biomass grown in protein rich and carbohydrate rich media were used for the egg formulation. The harvested biomass underwent a kill step to deactivate further growth of *Euglena* and a wash step prior to use of egg production.

To follow what was already learned from the dry egg formulation, the ingredients used in the initial formulation of liquid egg were kept the same as the final powder egg apart from using fresh biomass instead of *Euglena* protein rich flour. Also, concentrations of gellan gum and methyl cellulose were varied to find the best combination to provide the right texture for the egg, at the same time to keep their amounts as minimal as possible to reduce the cost of the egg.

More studies were conducted with other hydrocolloids such as carrageenan, sodium alginate and pectin in order to see whether methyl cellulose or gellan gum can be partially or completely replaced with cheaper hydrocolloids with improved functionality. Several formulations were also tried to identify the best amount of biomass and pea protein incorporated, which facilitate highest incorporation of *Euglena* based ingredients at the same time allowing better pourability, cooking properties and functionalities. Table 13 shows the initial egg formulation developed using fresh biomass alone. Initial formulation was intended to formulate liquid eggs only using fresh *Euglena* biomass as the only protein source.

Results and Discussion

Figure 4:
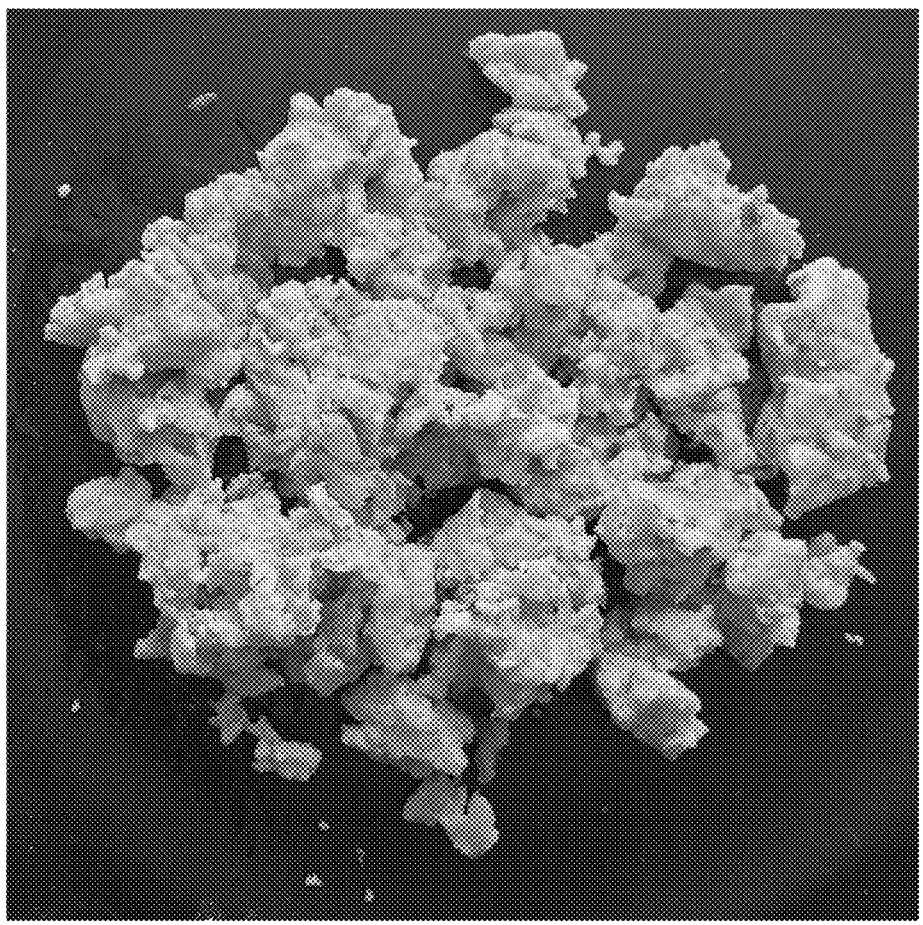
FIG. 4 shows an image of scrambled egg cooked using liquid egg prepared with formula 1 shown in Table 13.

The pourability of the mixture was good and the cooking time was only 2.5 to 3.5 minute. However, the mixture did not form a proper curd/gelation like the real egg while cooking although after cooking it looked almost like the real egg (as can be seen in FIG. 4). Furthermore, the protein content per serving did not meet the required amount, it was only 3.5 grams per serving and the serving size was too large.

TABLE 13

Initial liquid egg formulation developed using fresh biomass alone as a protein source. Given below is formula for 1 egg.

| Ingredient | Amount (g) | Amount (%) |
|---|---|---|
| Biomass * | 100 | 45.06 |
| Water | 100 | 45.06 |
| Oil (canola) | 20 | 9.01 |
| Gellan gum | 0.5 | 0.23 |
| Methyl cellulose | 0.625 | 0.28 |
| Yeast extract | 0.4 | 0.18 |
| Black salt | 0.4 | 0.18 |
| Total | 221.925 | 100 |

* Biomass consists of 10% solid, and ~35% protein, ~40% carbohydrate and ~7% lipids More studies were conducted by increasing gellan gum and methyl cellulose concentrations and biomass concentration in the formula 1 (Table 13), but no improvement in protein content per serving with a favourable texture for the product could not be achieved. Therefore, incorporation of various concentrations of pea protein (5 to 9.5%) with various concentrations of fresh biomass (60 to 85%) and water (0 to 35%) were tried in different formulations, and came up with a formulation which is given in Table 14.

TABLE 14

Liquid egg formulation using fresh biomass and pea protein as protein sources. Given below is a formula for 4 eggs.

| Ingredient | Amount(g) | Amount (%) |
|---|---|---|
| Biomass | 250 | 73.06 |
| Pea protein | 25 | 7.31 |
| Sunflower oil | 20 | 5.84 |
| Water | 42 | 12.27 |
| Gellan gum | 2.1 | 0.61 |
| Methyl Cellulose | 2.25 | 0.66 |
| Black salt | 0.45 | 0.13 |
| Yeast extract | 0.4 | 0.12 |
| Total | 342.2 | 100 |

Results and Discussion

Figure 5:
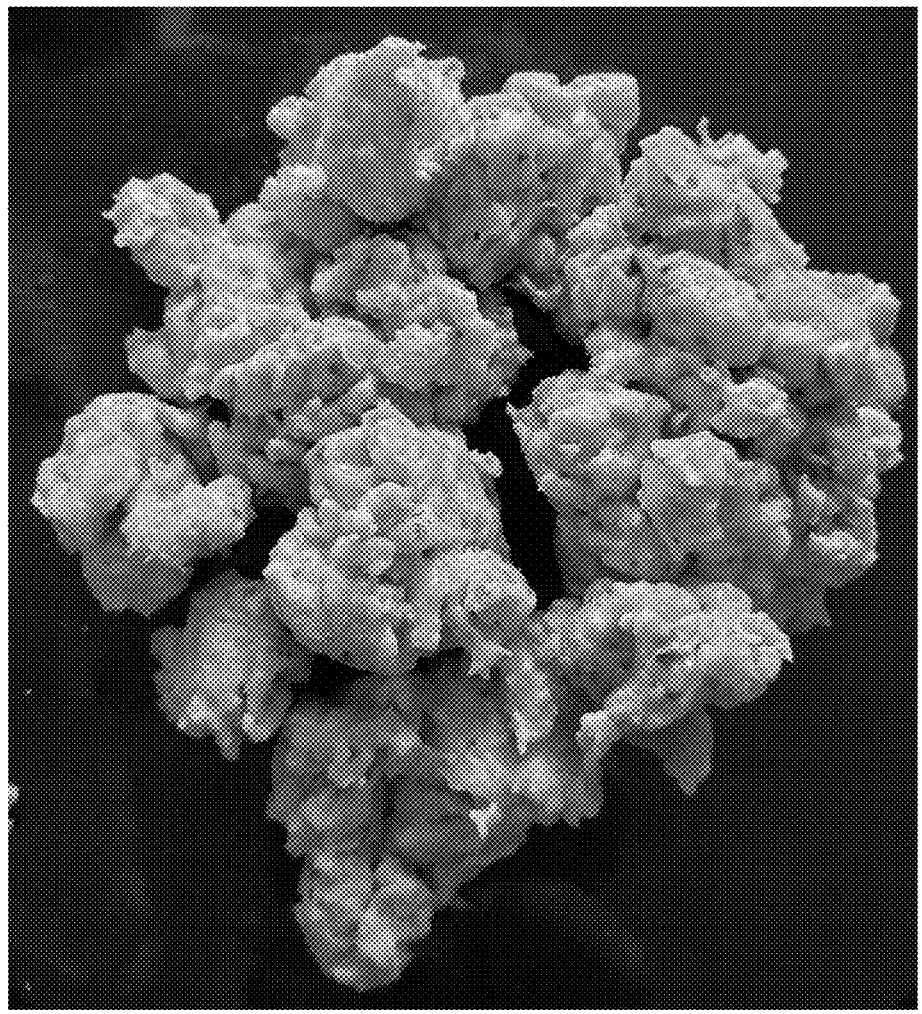
FIG. 5 shows an image of scrambled egg cooked using liquid egg formulated using formula shown in Table 14.

The liquid egg had a less than 2.5 minute cooking time, good texture and about 7.2 g protein per serving. After cooking the amount of cooked product was able to give about 50 g cooked product (see FIG. 5).

Figure 6:
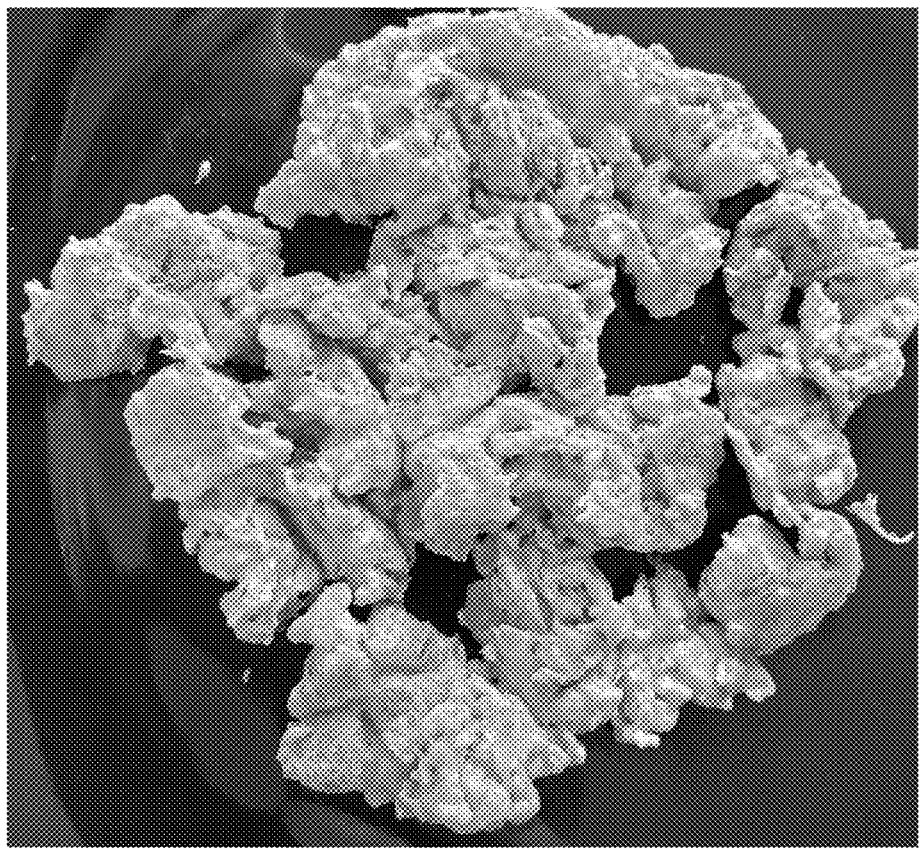
FIG. 6 shows an image of scrambled egg cooked using liquid egg formulated using formula shown in Table 15

Further studies were conducted by varying methyl cellulose concentrations from 0.6 to 0.8% and gellan gum concentrations from 0.4 to 0.7%. A formula shown in Table 15 was the best concentrations of methyl cellulose and gellan gum and shown in FIG. 6.

TABLE 15

Formula for liquid egg using fresh biomass and pea protein with the right amount of methyl cellulose and gellan gum. Formula given below is for four eggs.

| Ingredient | Amount(g) | Amount (%) |
|---|---|---|
| Biomass | 250 | 62.36 |
| Pea protein | 25 | 6.24 |
| Sunflower oil | 20 | 4.99 |
| Water | 97 | 24.20 |
| Gellan gum | 2 | 0.50 |
| Methyl Cellulose | 3.1 | 0.77 |
| Black salt | 0.8 | 0.20 |
| Yeast extract | 1.5 | 0.37 |
| onion powder | 0.5 | 0.12 |
| Transglutaminase | 1 | 0.25 |
| Total | 400.9 | 100 |

One observation during cooking was that the cooked egg was turning hard faster than the real egg. In order to prevent the hardening of the cooked egg, sunflower lecithin (an emulsifier), transglutaminase (an enzyme helps the gelling of protein) and baking powder was investigated to improve cooking texture. In total, about 30 formulations were tried.

It was found that the addition of sunflower lecithin, transglutaminase and baking powder improved the texture of the egg formulated using fresh biomass and pea protein. Two formulations shown in Table 16 were selected as two best formulations with and without transglutaminase in the formulation. Although it was better to have transglutaminase in the formula, the material was gelling in the refrigerator during storage and decreasing pourability of the egg. Moreover, transglutaminase may cause allergy and there may be regulatory issues associated with its use, so an alternative formulation without transglutaminase was finalized.

TABLE 16

Final liquid egg formulations using fresh biomass and pea protein.

| | Formula 1 | | Formula 2 | |
|---|---|---|---|---|
| Ingredient | Amount (g) | Amount (%) | Amount (g) | Amount (%) |
| Biomass | 250 | 54.93 | 250 | 62.20 |
| Pea protein | 25 | 5.49 | 25 | 6.22 |
| Sunflower oil | 20 | 4.39 | 20 | 4.98 |
| Water | 150 | 32.96 | 97 | 24.14 |
| Gellan gum | 2 | 0.44 | 2 | 0.50 |
| Methyl Cellulose | 3 | 0.66 | 3.1 | 0.77 |
| Black salt | 0.8 | 0.18 | 0.8 | 0.20 |
| Yeast extract | 1.5 | 0.33 | 1.5 | 0.37 |
| onion powder | 0.5 | 0.11 | 0.5 | 0.12 |
| Baking powder | 1 | 0.22 | 1 | 0.25 |
| Sunflower lecithin | 1.3 | 0.29 | 0 | 0 |
| Transglutaminase | 0 | 0 | 1 | 0.25 |
| Total | 455.1 | 100 | 401.9 | 100 |

Results and Discussion

The eggs were formulated using formula 1 and 2 shown in Table 16 were able to form a good texture with 7.5 g protein per serving. The cooking time was less than 2 minutes with a cooked product of about 53 g.

More studies were conducted in order to find the best hydrocolloid for the liquid egg. In order to do that, either gellan gum or methyl cellulose was replaced in the formula 1 shown in Table 16 with carrageenan, sodium alginate, and pectin. However, none of these hydrocolloids worked as good as the combination of methyl cellulose and gellan gum. No egg like structure or gelling happened while using these hydrocolloids. Furthermore, the cooking time increased. Therefore, these hydrocolloids were excluded from any future studies. The best combination was still gellan gum with methyl cellulose (2:3 ratio)

Eggs were prepared using the same formulation shown in Table 16 (formula 1) using biomass grown in protein rich or carbohydrate rich media and in different fermentation tanks. The following were then found.

Although two biomasses were grown in different media, the amount of protein (~35%) and carbohydrates (~40%) presented in the biomasses were not significantly different. Not much difference between the texture of the egg made using protein rich media and carbohydrate rich media grown biomasses. Biomass from the protein rich media was more viscous and gave slightly higher fluffy texture for the egg.

Carbohydrate rich grown biomass has better flavour than protein rich one, even without any maskers added, provided better flavour for the product, but it has less yellow color. The good flavour might be due to the difference in washing step used for the carbohydrate rich media grown biomass, which was washed with 2.5 times water compared to the protein rich biomass which was just diluted with water and centrifuged.

Conclusions

A liquid egg with less than 2 minutes cooking time and 7.5 g protein per serving with a serving content of 53 g can be prepared using fresh biomass grown either using protein rich media or carbohydrate rich media in combination with pea protein. Flavour of the egg can be improved by addition of yeast extract, black salt and onion powder. The texture of the egg was achieved by using the right combination of methyl cellulose and gellan gum and pea protein and biomass. This egg is similar to a standard chicken egg which when cooked is 50-55 g, 6-6.5 g of protein per serving for less than a minute cook time.

Example 13: Liquid Egg Formulation Using Wet Protein Concentrate Prepared from Fresh Biomass Fresh biomass with 10 w/w % solid content only consisting of 35% protein, which will only provide a maximum of 3.5 g protein is used 100 g biomass in one serving of egg. If the protein content in the biomass can be enhanced, a higher amount of protein from *Euglena* can be achieved in the egg formulation. In order to do that, the beta glucan isolate (BGI), the carbohydrate present in the *Euglena* biomass, was removed from the biomass and the protein was concentrated using isoelectric precipitation method.

Liquid Egg Objective:

Objective of the described study was to formulate liquid egg using wet protein concentrate alone as a protein source in the liquid egg with reasonable cooking time and similar texture as that of the liquid egg formulated using fresh biomass and pea protein.

The first formulation of liquid egg using wet protein concentrate was prepared using a protein concentrate with 4-5 w/w % solid content. The formula is shown in Table 17.

TABLE 17

The liquid egg formulation using wet protein concentrate with 5 w/w % solid content. Given below is the formula for 1 egg.

| Ingredient | Amount(g) | Amount (%) |
|---|---|---|
| Protein concentrate | 200 | 93.79 |
| Pea protein | 0 | 0 |
| Sunflower oil | 10 | 4.69 |
| Water | 0 | 0 |
| Gellan gum | 0.5 | 0.23 |
| Methyl Cellulose | 0.75 | 0.35 |
| Black salt | 0.3 | 0.14 |
| Yeast extract | 0.5 | 0.23 |
| onion powder | 0.2 | 0.09 |
| Baking powder | 0.5 | 0.23 |
| Sunflower lecithin | 0.5 | 0.23 |
| Total | 213.25 | 100 |

Results and Discussion

Figure 7:
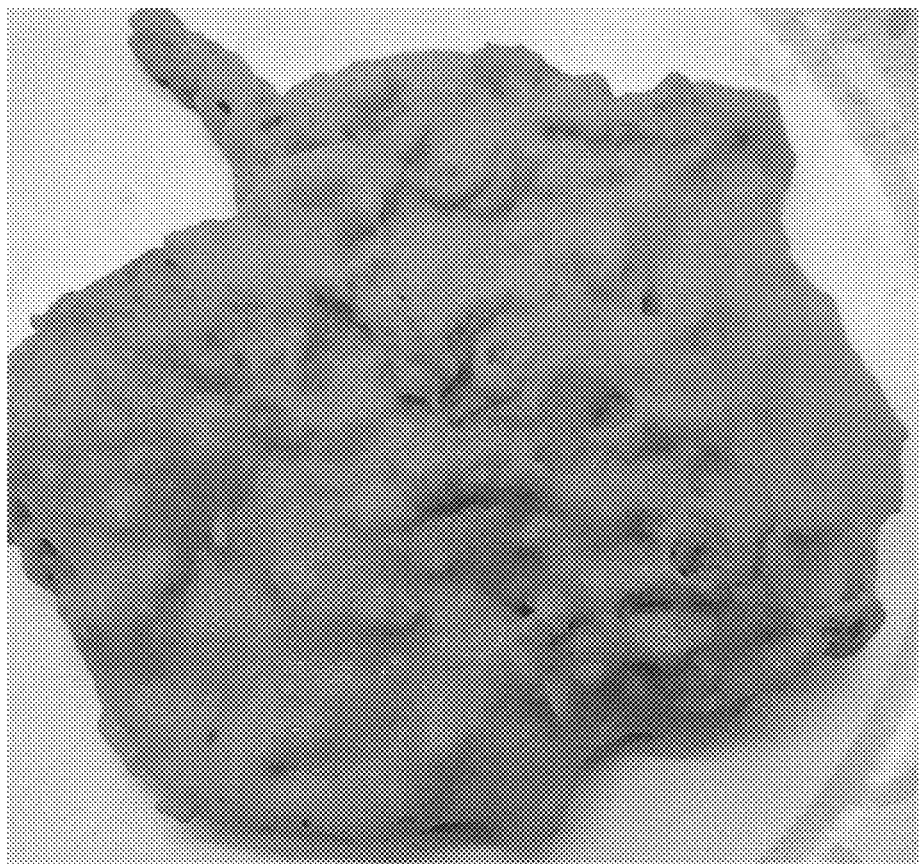
FIG. 7 shows an egg cooked using liquid egg formulated using protein concentrate with 5 w/w % solid content

The cooking time for this formula was about 4 min, but it did not form a texture similar to the liquid egg prepared using fresh biomass and pea protein. There were no curd or gel formations occurred and obtained a product shown in FIG. 7.

The cooked product was only 46 g with 5.6 g protein per serving. Although the amount of gellan gum and methyl cellulose shown in the formula was increased to 0.5% and 0.7%, respectively, no betterment in the egg texture was obtained. The issue was having not enough functional protein in the formulation. This can be achieved by increasing the wet protein concentrate in the formulation, but it will also increase the cooking time and increase in hydrocolloid addition might be also required. Therefore, it was necessary to increase the solid content of the initial wet protein concentrate to increase the protein content in the formula without increasing any cooking time or having to use a higher amount of hydrocolloid.

A new formulation of liquid egg was then obtained with a protein concentrate that has about 15% solids content. The final formula developed using this protein concentrate is shown in Table 18.

TABLE 18

Liquid egg formula using Euglena protein concentrate with 15 w/w % solid content

| Ingredient | Amount(g) | Amount (%) |
|---|---|---|
| Protein concentrate | 60 | 55.56 |
| Pea protein | 0 | 0 |
| Sunflower oil | 5 | 4.63 |
| Water | 40 | 37.04 |
| Gellan gum | 0.5 | 0.46 |
| Methyl Cellulose | 0.9 | 0.83 |
| Black salt | 0.3 | 0.28 |
| Yeast extract | 0.3 | 0.28 |
| onion powder | 0.2 | 0.18 |
| Baking powder | 0.5 | 0.46 |
| Sunflower lecithin | 0.3 | 0.28 |
| Transglutaminase | 0 | 0 |
| Total | 108 | 100 |

Results and Discussion

Figure 8:
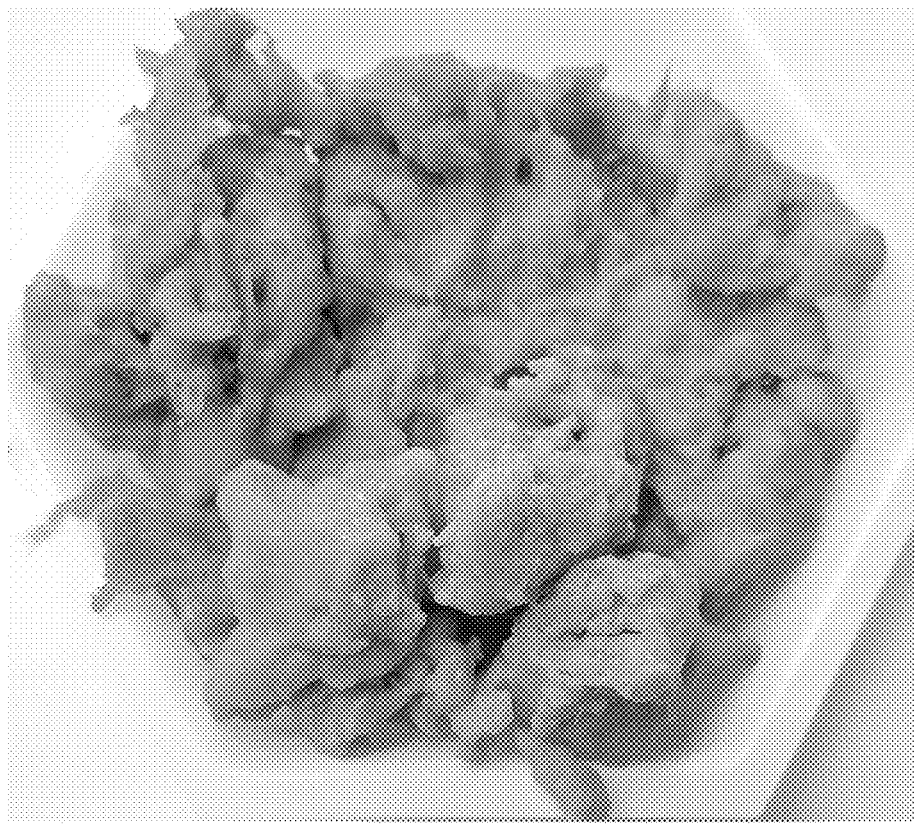
FIG. 8 shows a cooked liquid egg prepared using *Euglena* protein concentrate with 15 w/w % solid content.

Liquid egg with 6.25 g protein per serving with a serving size of 49 g (cooked product) was developed using wet protein concentrate with ~15 w/w % solid content as can be seen in FIG. 8. Texture of this egg was not as good as the liquid egg formulated using fresh biomass and pea protein, but very close to that. Flavour of the egg was close to the liquid egg prepared using fresh biomass and pea protein, however the fresh biomass liquid egg was better Conclusions A liquid egg with more than 6 g protein per serving and less than 2 minutes cooking time with a serving size of ~50 g was formulated using wet protein concentrate in which *Euglena* protein is the only protein source. Texture of the egg formulated using only wet *Euglena* protein concentrate was very similar to the liquid egg formulated using fresh biomass and pea protein.

Example 14: Flavour and Quality Improvement of *Euglena* Based Liquid Egg

Although the texture of the cooked eggs formulated using both fresh biomass and wet protein concentrate was very close to the real egg, the flavour of the *Euglena* based egg was not anything close to the real egg. The unfavourable marine flavour of the *Euglena* persisted in the final egg product even though yeast extract, black salt and onion powder was added.

For the liquid egg formulations using fresh biomass or wet or powdered *Euglena* protein concentrate maskers are required to mask the marine flavours of *Euglena*. An ideal masker should completely mask the off notes (both aroma and flavour) coming from *Euglena* during cooking and in cooked products without introducing any new flavours or aroma. Flavours can also be used to improve the flavour of cooked liquid egg. Ideal flavour should provide a flavour that is similar to cooked real egg. Since the amount of *Euglena* is higher in protein concentrate a higher amount of masker/flavour will be required for protein concentrate based liquid egg formulations. Some of these maskers that could cover the off notes (marine flavour of *Euglena*) are commercially available from: Firmenich, IFF, Givaudan, Symrise, Mane, Fona, Flavor producer, McCormick, edlong, T•Hasegawa. Sensient Flavors, Robertet SA, Prova, Wild/ADM, Takasago, Synergy, and others.

Example 15: Safety of Biomass and Wet Protein Concentrate for Egg Formulations

Since the biomass and the wet protein concentrate consists of a significant amount of water, it facilitates the growth of microorganisms such as bacteria, yeast and mold, which leads to the spoilage of biomass/wet protein concentrate. It can also lead to spoilage of the liquid egg formulated using these materials during the storage. Therefore, it is essential to understand if there is any growth of microbes and the spoilage time and adopt any prevention method to protect the biomass/wet protein concentrate from spoilage.

Identification of Microbes in the Fresh Biomass and Wet Protein Concentrate

Figure 9:
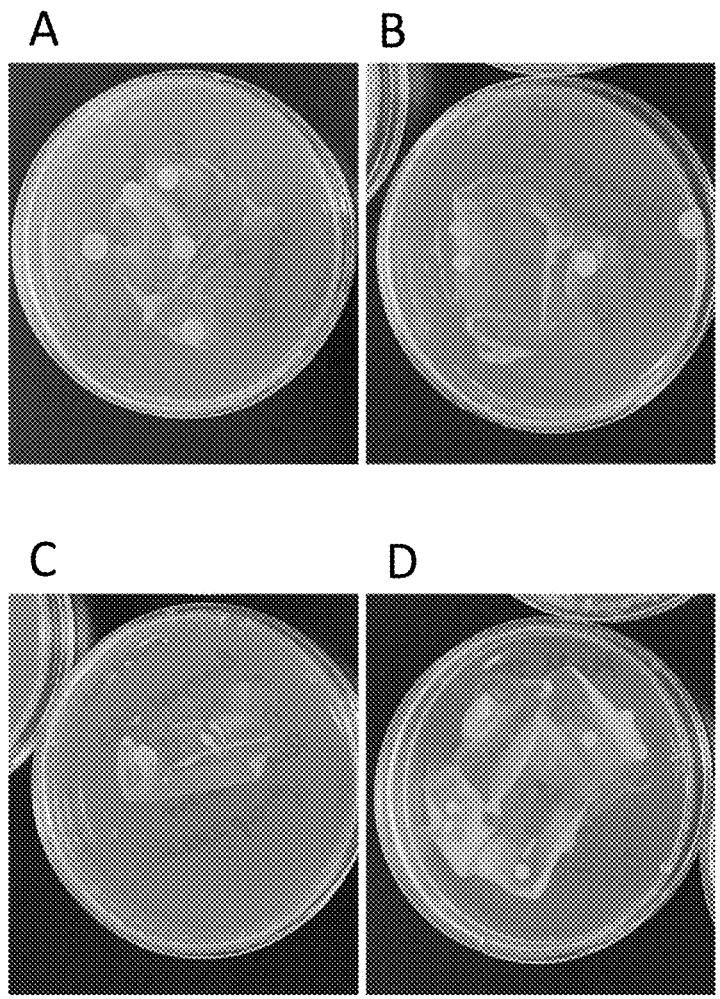
FIG. 9 shows TSA plates of fresh biomass at pH 7 stored at 30° C. for 2 days. The samples were plated: A) before at 0 hours, B) 3 hours of storage in the refrigerator C) 6 hours of storage in the refrigerator and D) 18 hours of storage in the refrigerator.

Method Used for Microbial Analysis of Fresh Biomass:

Obtained fresh biomass and biomass was washed 1 time with 2.5 times with water. The biomass was diluted to 10% (solid content-10.36 w/w %), initial pH was pH 3.35 and the pH was adjusted to 7.2 using 2.5 M NaOH. A small amount of this biomass was then spread on a TSA plate in a biosafety cabinet with a sanitized environment and stored at 30° C. for 2 days to see any growth. A negative control was also used (a TSA plate left opened during sampling and stored with the sample plates). The biomass was stored in the 4° C. refrigerator for 3 days plating was done after 3 hours, 6 hours and 18 hours of storage. The images of plates after two days of storage are shown in FIG. 9.

Results and Discussions:

The presence of microbes such as bacteria, yeast and mold were detected in fresh biomass and they continued their growth during storage. The number of microbes found were not correlated with storage time, this might be due to the inconsistency of the amount of sample poured on to the plate.

Method Used for Microbial Analysis of Wet Protein Concentrate:

The wet protein concentrate with 17.6% solid was diluted with 4 times water. The pH was then adjusted to pH 4.5 and a sample was poured into a TSA plate. The plate was then stored at 30° C. to facilitate the growth of microbes if there is any. A negative control was also used as described above.

Figure 10:
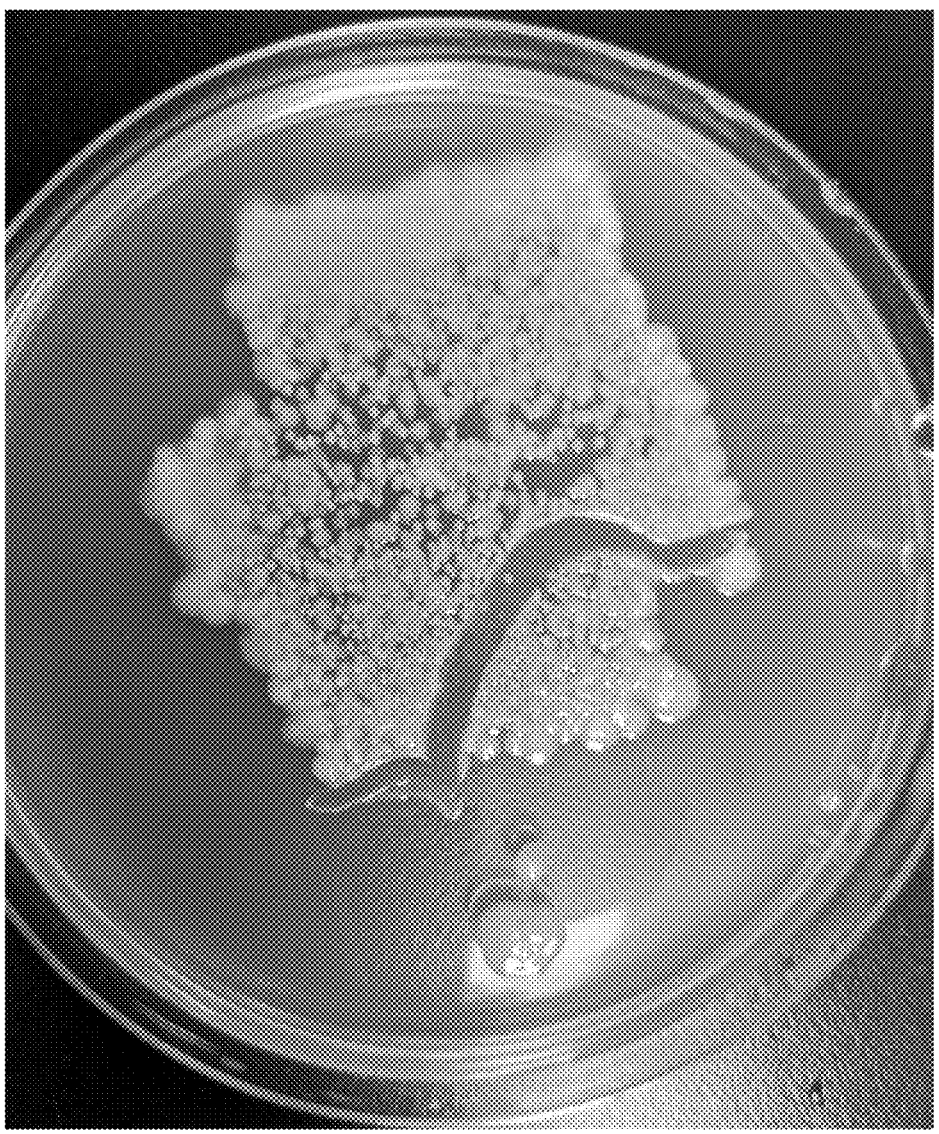
FIG. 10 shows TSA plate of wet protein concentrate at pH 4.5 after two days of storage at 30° C.

Results and Discussions:

The image of the TSA plate after two days of storage at 30° C. is shown in FIG. 10. When a small sample from the growth was viewed under the microscope, presence of various kinds of bacteria as well as the presence of fungus were observed.

Methods Tested to Prevent the Growth of Microorganism in Fresh Biomass and Wet Protein Concentrate There are several approaches to prevent the growth of microorganisms in the wet food systems i.e. biomass, wet protein concentrate or liquid egg. Most common approaches are pasteurization and treatment of food products with food grade and safe antimicrobial agents such as Nisin, cultured dextrose, organic acids etc.

The first approach tried was the pasteurization of liquid eggs. Pasteurization is a method in which the required product will be heated to a specific selected temperature for required time to kill the microorganisms presented in the food systems. Then the food material will be packed safely to prevent the entrance of any microbes and thus protect the food systems from spoilage.

Four different temperatures were chosen to pasteurize liquid eggs, 70° C., 65° C., 60° C. and 55° C. The liquid egg was heated to this temperature for 30 minutes. Even heating of liquid egg at 55° C. leads to the gelation of gellan gum into the formula and the product cannot be used or cooked after words. Therefore, it was understood that the pasteurization of the final liquid egg formula is not possible. Hence, pasteurization of fresh biomass and treatment of fresh biomass with an antimicrobial agent, Nisin was investigated.

Pasteurization Method:

Collected fresh biomass and diluted to 10% solid and adjusted the pH to pH 7 and plated on a TSA plate. Biomass was heat treated to kill *Euglena* and 2.5 times washed. A fraction of biomass was heat treated at 75° C. for 15 minutes. This temperature was chosen to keep the protein protected from denaturation as much as possible (denaturation of protein might affect the functionality of protein and performance of liquid egg during cooking.) To do that 50 g of biomass with 10% solid and pH 7 was taken in a 250 ml glass beaker (washed with 70% ethanol and dried) and heated in a water bath set at 99° C. After heat treatment, the material was quickly immersed in an ice bath and brought back the temperature to 20° C. A small aliquot of non-treated (control—C) and heat-treated (pasteurized—P) samples were plated and incubated at 30° C. for 6 days to see any microbial growth.

Microbial Analysis: A small portion of plate with microbial growth was dispersed in water and observed under a light microscope. The remaining portion is sent for a detailed identification test. The analysis showed the presence of Lysinbacillus and two fungal genera, *aspergillus* and *Fusarium*.

Figure 11:
FIG. 11 shows TSA Plates of A) non-treated and B) 15 minutes at 75° C. heat treated biomass after 6 days of storage of the TSA plates.
Figure 11:
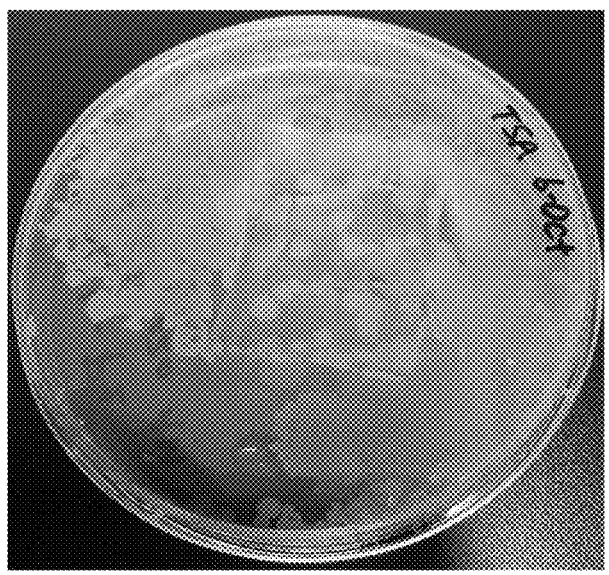
Figure 12:
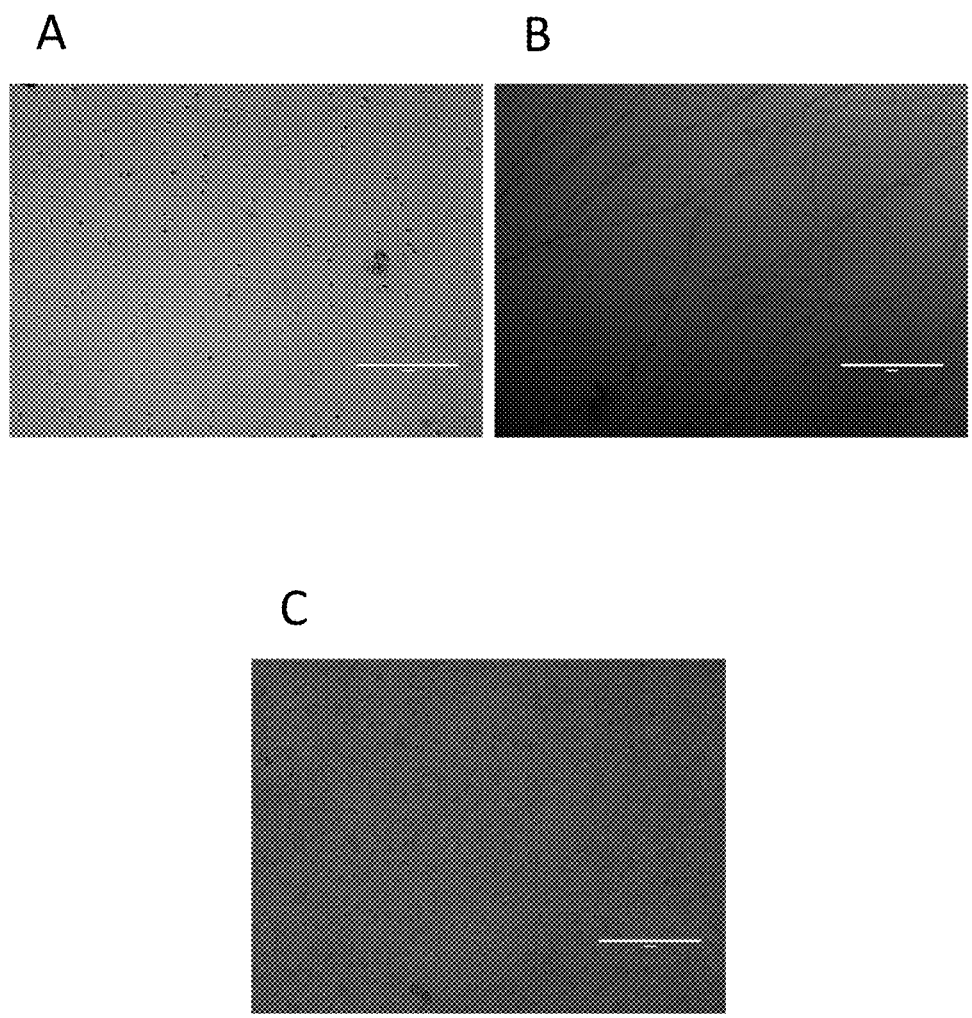
FIG. 12 shows A) Bacteria B) Fungus observed in non-treated biomass and C) bacteria in heat-treated biomass observed after 6 days of storage of TSA plates.
Figure 13:
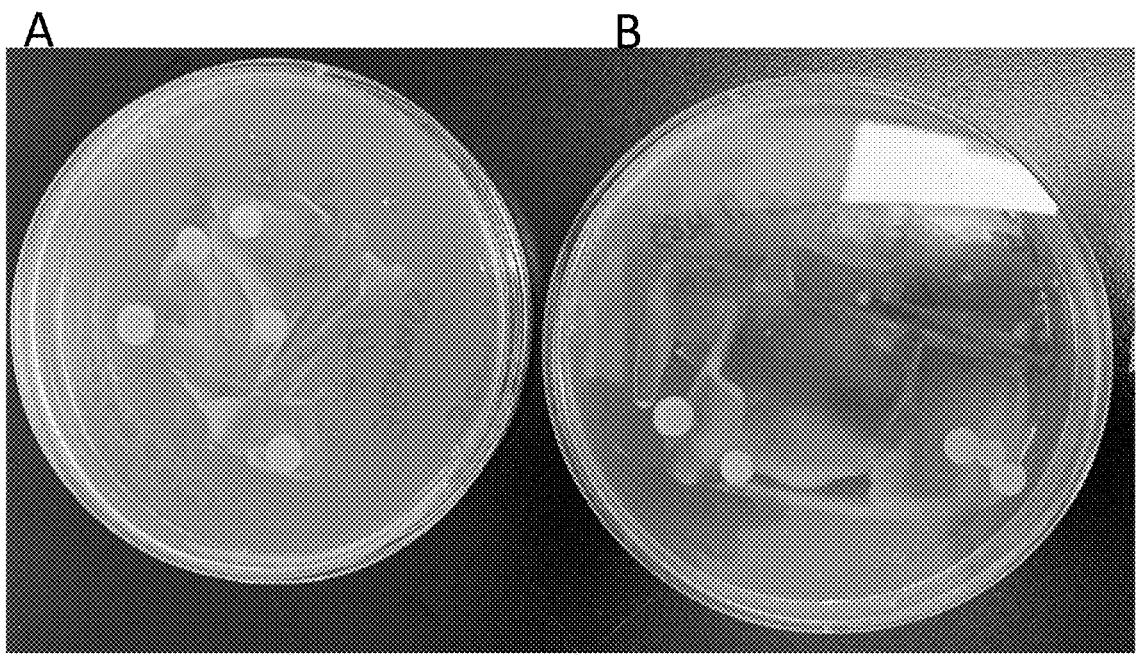
FIG. 13 shows TSA plates of biomass treated: A) without nisin (left) and with B) 70 ppm nisin (right), stored at room temperature.
Figure 14:
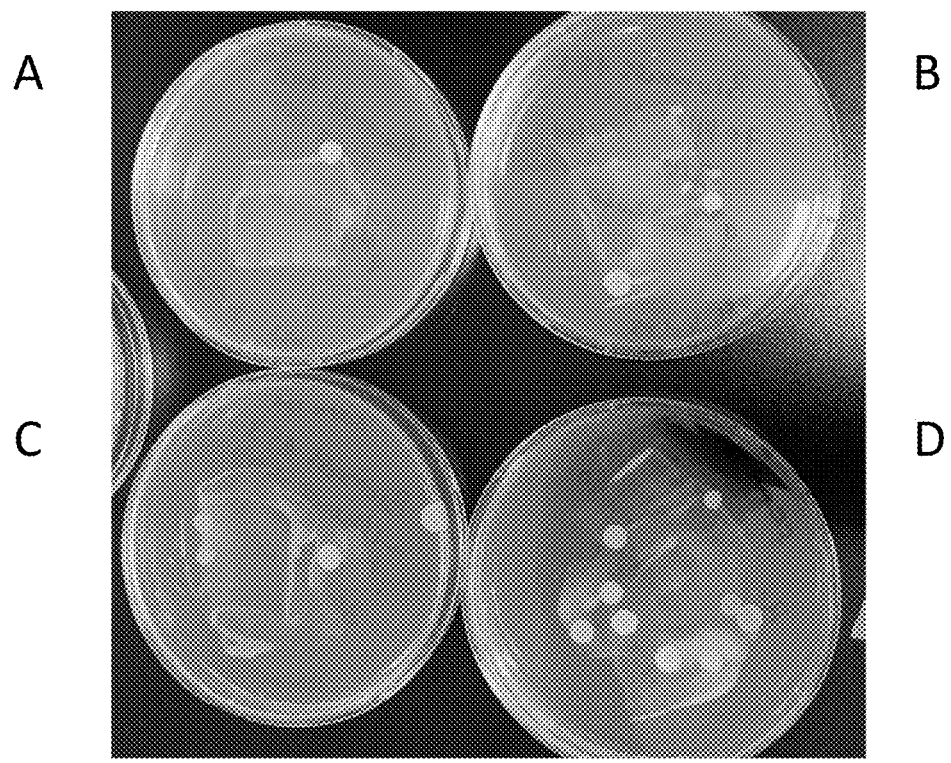
FIG. 14 shows TSA plates of treated biomass for 3 hours: A) without nisin (left, top) stored at room temperature, B) with 70 ppm nisin (right, top), stored at room temperature, C) without nisin (left, bottom) stored at 4° C. temperature and D) with 70 ppm nisin (right, bottom), stored at 4° C. temperature.
Figure 15:
FIG. 15 shows TSA plates of treated biomass for 6 hours: A) without nisin (left, top) stored at room temperature, B) with 70 ppm nisin (right, top), stored at room temperature, C) without nisin (left, bottom) stored at 4° C. temperature and D) with 70 ppm nisin (right, bottom), stored at 4° C. temperature.
Figure 16:
FIG. 16 shows TSA plates of treated biomass for 18 hours: A) without nisin (left, top) stored at room temperature, B) with 70 ppm nisin (right, top), stored at room temperature, C) without nisin (left, bottom) stored at 4° C. temperature and D) with 70 ppm nisin (right, bottom), stored at 4° C. temperature.
Figure 17:
FIG. 17 shows TSA plates of treated biomass for 24 hours: A) without nisin (left, top) stored at room temperature, B) with 70 ppm nisin (right, top), stored at room temperature, C) without nisin (left, bottom) stored at 4° C. temperature and D) with 70 ppm nisin (right, bottom), stored at 4° C. temperature.

Results and Discussions:

Observation: Irrespective of heat treatment, all biomass displayed presence of microbes (FIG. 11). Microscopic analysis showed the presence of bacteria in both heated and non-heated biomass, but presence of fungus was only observed in non-heated biomass (FIG. 12). The study shows that the heat-treatment at 15 minutes was not enough to kill the bacteria but was enough to kill the fungus.

Treatment of Biomass with Nisin:

Method: Obtained fresh biomass and was washed 1 time with 2.5 times water. The biomass was diluted to 10% (solid content-10.36 w/w %, initial pH was pH 3.35 and the pH was adjusted to 7.2 using 2.5 M NaOH. Then 70 ppm of nisin was added to 500 g biomass, mixed well and split into 2 parts and one bottle was left in the 4° C. refrigerator and the other one at room temperature. Similarly, about the same amount of biomass without Nisin was also left at both conditions.

Results and Discussions:

Presence of microbes were found at all storage conditions irrespective of the presence of nisin or storage time. Presence of bacteria and yeast were detected on the TSB plates (microscopic analysis) as can be seen in FIGS. 13-17. Increased amount of growth was not correlated with presence of nisin or storage time (might be due to the inconsistency in the amount of sample used for plating).

Conclusions:

Pasteurization at lower temperature or treatment with 75 ppm of Nisin will not be able to prevent the growth of microorganisms in the fresh biomass or wet protein concentrate. Therefore, alternative methods need to be obtained to prevent the spoilage of biomass, wet protein concentrate as well as liquid egg during storage.

Effect of pH, Heat Treatment and Antimicrobial Treatment on the Microbial Growth and Spoilage of Biomass Objective:

Objective of the study was to determine whether heat treatment, storage pH and addition of antimicrobial substances has any effect on the microbial growth and spoilage of biomass stored in the 4° C. refrigerator.

Procedure:

A biomass stored in the refrigerator at harvested pH (pH 2.75) for 2 days after harvest was chosen for microbial analysis. Four different pH conditions were used for non-heat treated biomass storage, pH 3, 4.5, 5 and 7. Three different antimicrobials (see Table 19 for the names and usage levels) were added to biomass at each pH selected. Control without any antimicrobial agents were also stored at different selected pHs. All the biomass samples were stored in a 4° C. refrigerator for 5 days and a TSA plate assay was done to see the presence of any microbes at the 5 day mark.

TABLE 19

Antimicrobials tested on freshly harvested biomass

| Antimicrobials selected | Short form used | Usage level |
| --- | --- | --- |
| Calcium propionate | CP | 1000 ppm |
| Sodium benzoate + potassium sorbate | SB + PB | 1000 ppm each |
| Cultured dextrose (Bio Vontage 2662) | BV | 0.25% (w/w) |

Heat Treatment of Biomass:

The same biomass used in the previous step was taken in a glass beaker and heated in a water bath at 95° C. The temperature of the biomass was reached at 75° C. and stayed constant. The biomass was then left at this temperature for 30 minutes and stirred using a sterilized spatula every 5 minutes. The biomass was then immediately cooled using an ice bath left in a biosafety cabinet to room temperature. The pH of this biomass was then adjusted to pH 3, 4.5 and 5 and added a mixture of Sodium benzoate and Bio Vontage 2662 (cultured dextrose) was added at each pH condition. A heat treated biomass without any antimicrobial agents was also stored at each pH as a control. The biomass was stored in a 4° C. refrigerator and TSA plate analysis was conducted to see any microbial growth.

Figure 18:
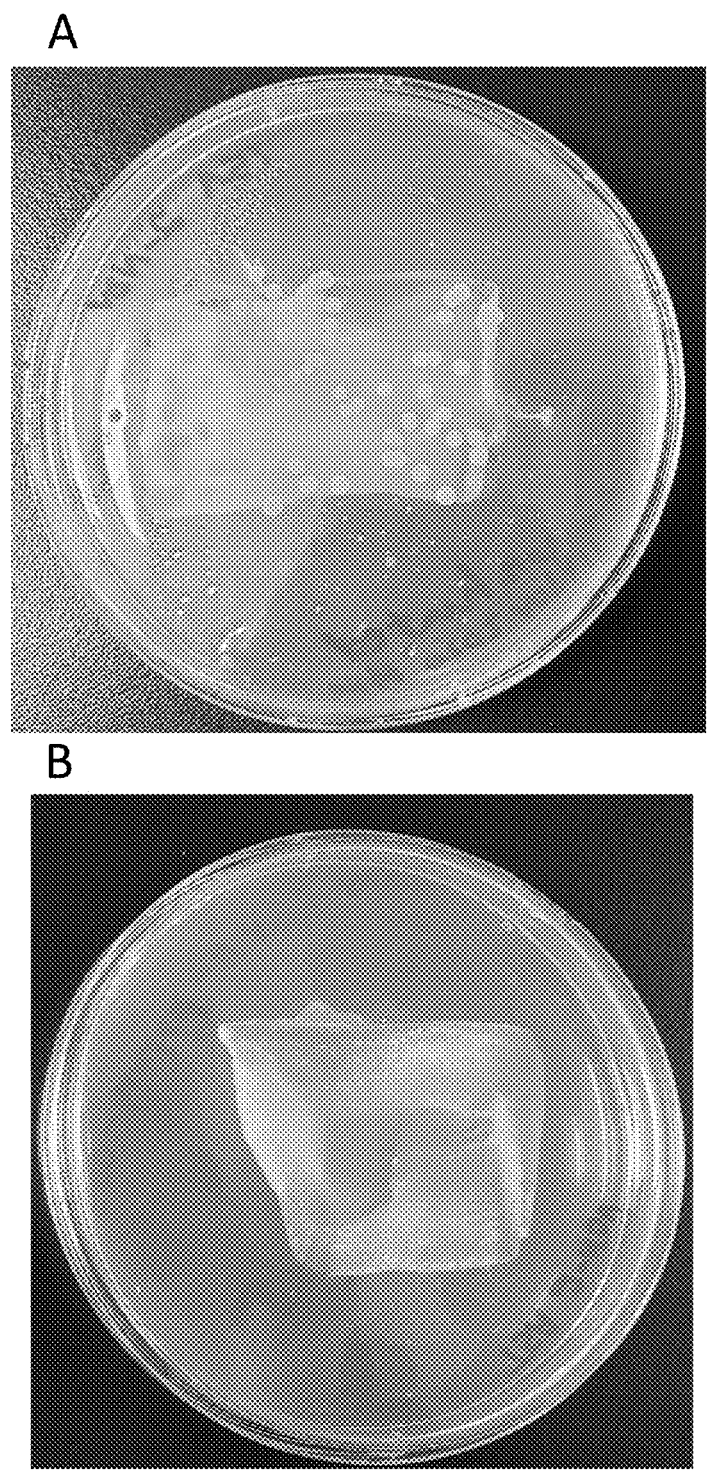
FIG. 18 shows TSA plates of A) non-heat treated and B) heat treated (75° C. for 30 minutes) biomass on the beginning of the study.
Figure 19:
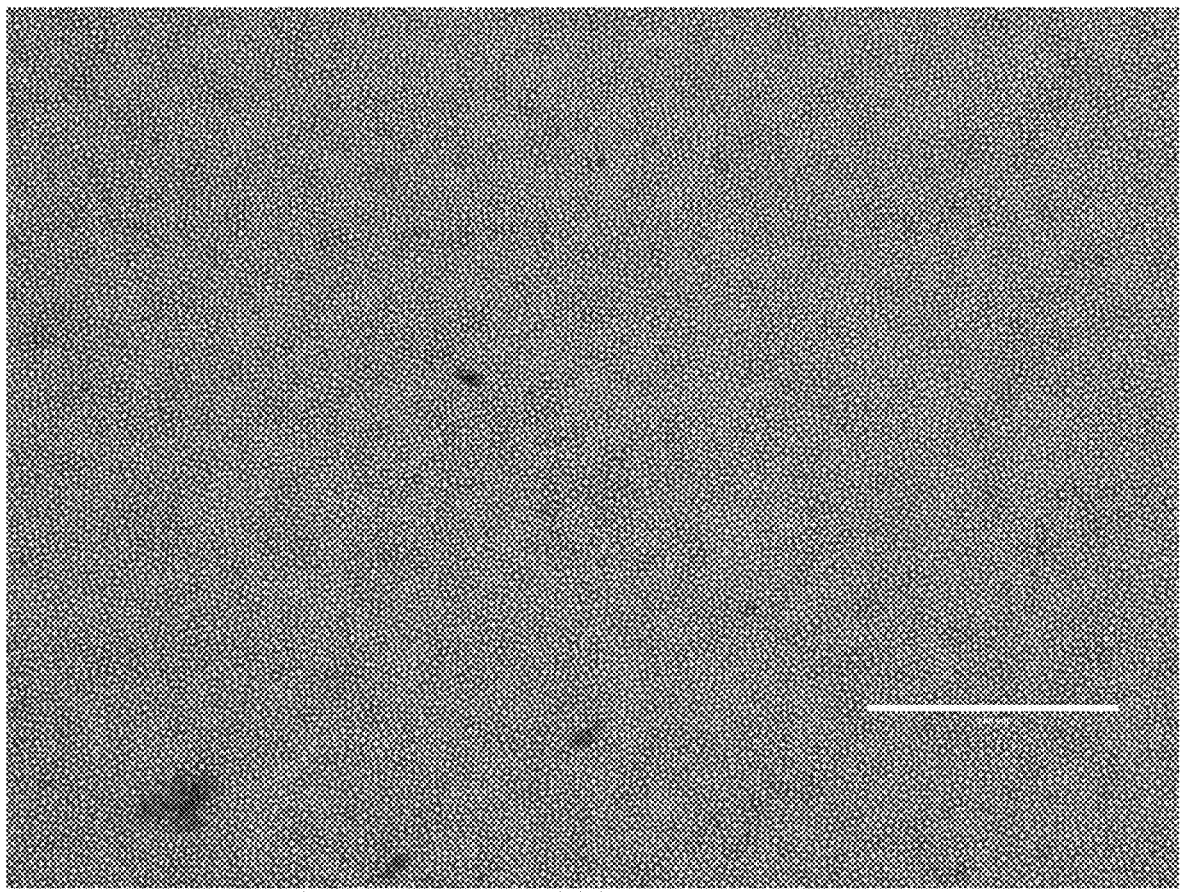
FIG. 19 shows microscopy image of what was growing on the TSA plate of non-treated biomass on day 0.

Results and Discussions:

Images of TSA plates of heat treated and non-heat treated biomass on the first day of microbial analysis study is shown in FIG. 18. As seen, there was no microbial growth in heat treated biomass but there was evidence of Fungal growth in non-heated biomass. The growth found in non-heated biomass was observed under microscope and it was found that the growing microbe was yeast (see FIG. 19)

Figure 20:
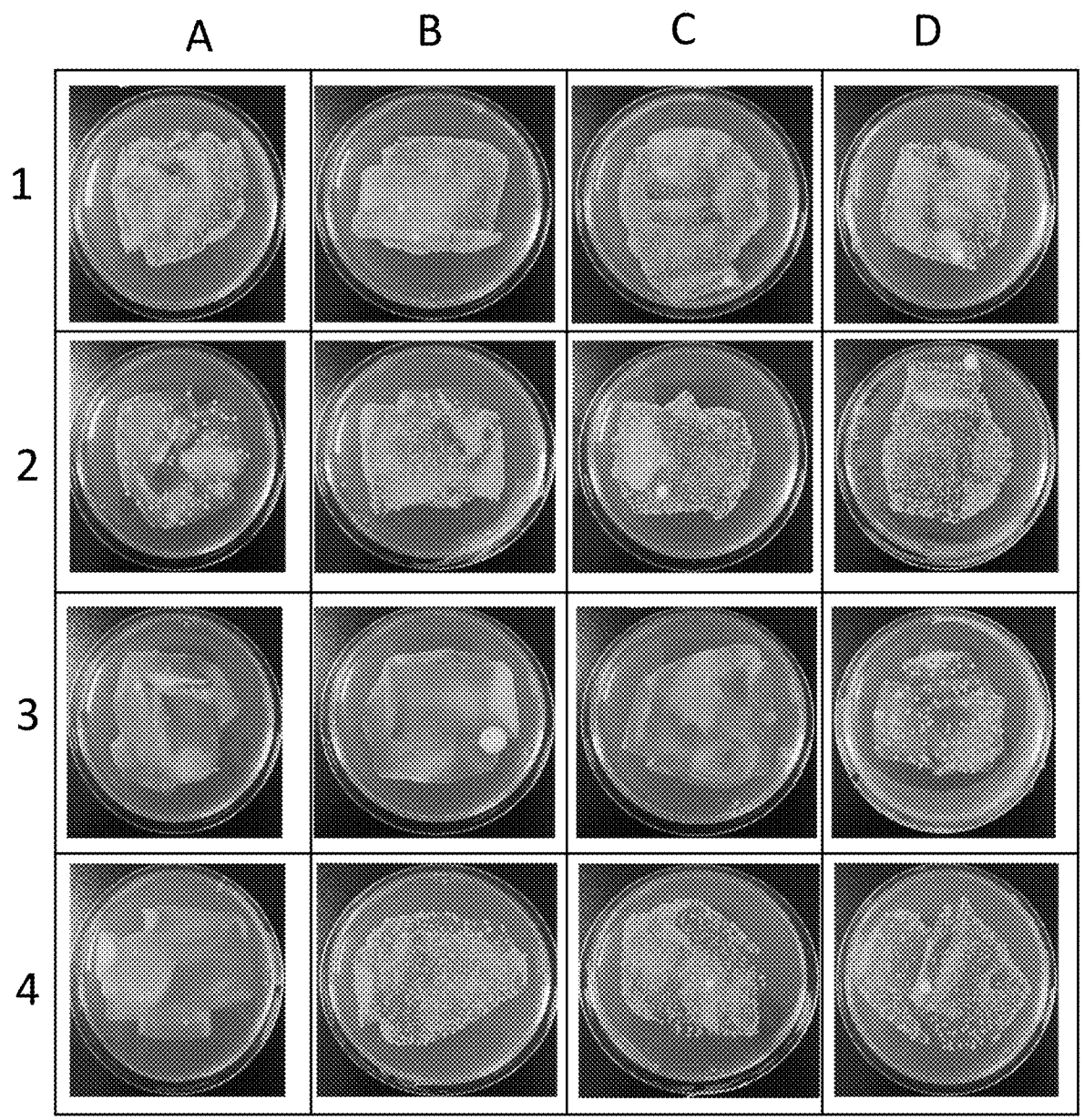
FIG. 20 shows images of TSA plates of non-heat treated biomass stored at 4° C., for 5 days at different pH with and without antimicrobial agents. Column A) represents pH 3, Column B) represents pH 4.5, Column C) represents pH 5, and Column D represents 7. Row 1 represents the control, non-treated biomass at the different pH conditions. Row 2 represents Calcium propionate (CP, 1000 ppm) treated biomass at the different pH conditions. Row 3 represents Sodium benzoate and potassium sorbate (SB+PS, 1000 ppm each) treated biomass at the different pH conditions. Row 4 represents Cultured dextrose (BV, 0.25 w/w %) treated biomass at the different pH conditions.

The images of plates of non-heat treated biomass control and with antimicrobial agents is seen in FIG. 20. Images of plates from heat treated (75° C. for 30 minutes) with and without antimicrobial agents is seen in FIG. 21.

Figure 21:
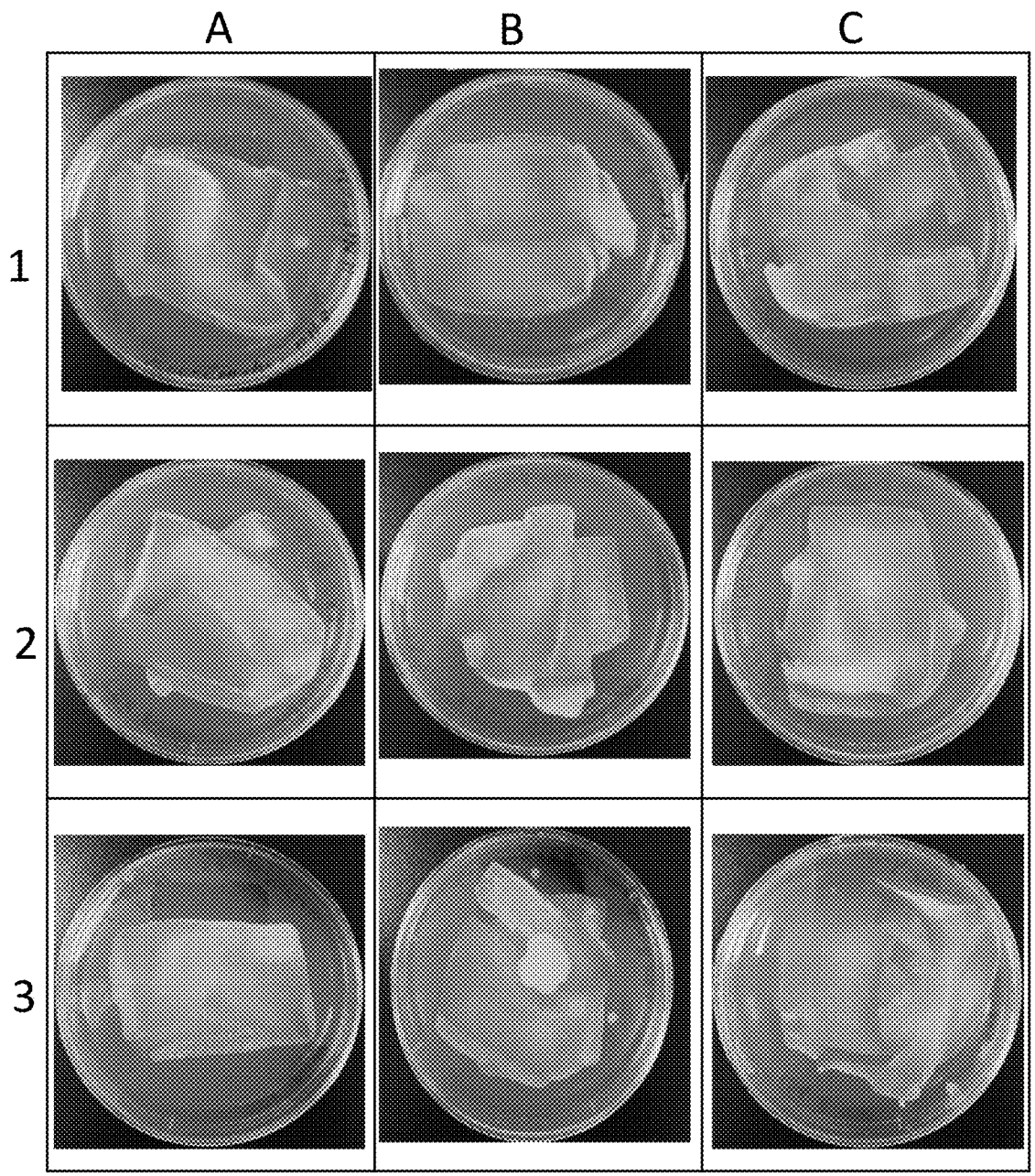
FIG. 21 shows images of TSA plates of heat treated biomass stored at 4° C., for 5 days at different pH with and without antimicrobial agents. Column A) represents pH 3, Column B) represents pH 4.5, and Column C) represents pH 5. Row 1 represents the control, non-treated biomass at the different pH conditions. Row 2 represents Sodium benzoate and potassium sorbate (SB+PS, 1000 ppm each) treated biomass at the different pH conditions. Row 3 represents Cultured dextrose (BV, 0.25 w/w %) treated biomass at the different pH conditions.

As can be seen from FIG. 20 and FIG. 21, the microbial growth in the biomass was determined by the pH of the biomass, presence of antimicrobial agents and heat treatment. When the biomass was not heat treated, even with antimicrobial agents, microbes were present at pH 7. The microscopic analysis showed that the microbes present at pH 7 were yeast and mold. However at all the other pH, addition of the combination of SB+PS helped to prevent any microbial growth. In fact, these antimicrobial agents killed all the microbes present in the biomass and none of the other antimicrobial agents tested were as effective. In the case of the heat treated biomass, no microbial growth was observed in any pH even without any antimicrobials, except, there was microbial growth at pH 4.5 when Bio Vontage was present. A summary of the type of microorganisms presented in non-heat treated and heat treated biomass at different pH is shown in Table 20 and 21, respectively.

TABLE 20

Microbial growth observed in non-heat treated biomass with antimicrobials at different pH after storage in the refrigerator for 5 days. Control has no antimicrobial agents.

| pH | Control | CP | SB + PS | BV |
|---|---|---|---|---|
| 3 | yeast | yeast | no microbes | yeast (very low in number) |
| 4.5 | yeast and mold | yeast | no microbes | yeast |
| 5 | yeast and mold | yeast and mold | no microbes | yeast and mold |
| 7 | yeast and mold | yeast and mold | yeast and mold | yeast and mold |

TABLE 21

Microbial growth observed in heat treated biomass with antimicrobials at different pH after storage in the refrigerator for 5 days. Control has no antimicrobial agents

| pH | Control | SB + PS | BV |
|---|---|---|---|
| 3 | no microbes | no microbes | no microbes |
| 4.5 | no microbes | no microbes | Fungus |
| 5 | no microbes | no microbes | no microbes |

Figure 22:
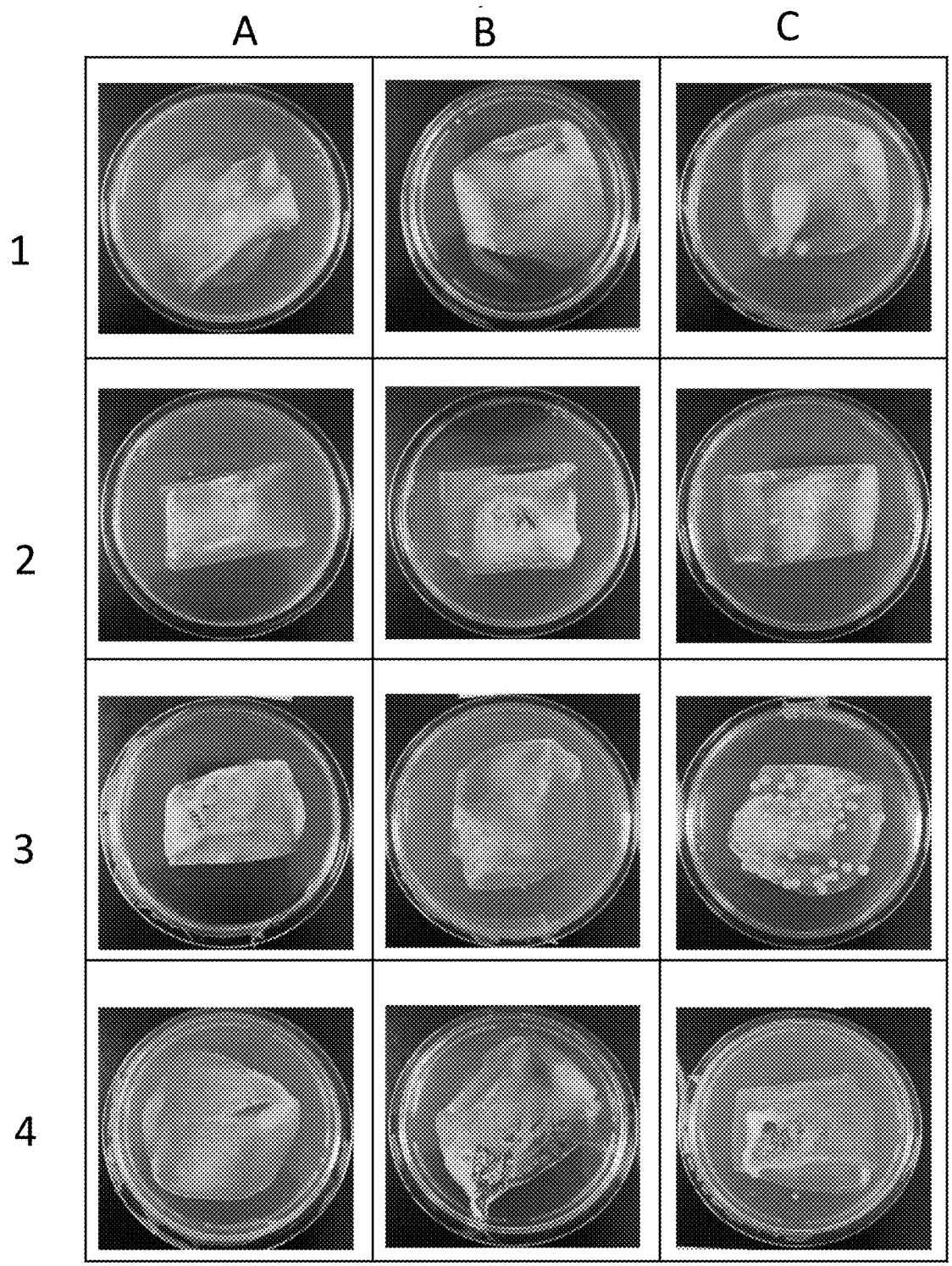
FIG. 22 shows images of TSA plates of various treated biomass stored at 4° C., for 16 days at different pH with and without antimicrobial agents. Column A) represents pH 3, Column B) represents pH 4.5, and Column C) represents pH 5. Row 1 represents non heat treated biomass with Sodium benzoate and potassium sorbate (SB+PS, 1000 ppm each) at the different pH conditions. Row 2 represents the heat treated biomass control, at the different pH conditions. Row 3 represents heat treated biomass with Cultured dextrose (BV, 0.25 w/w %) at the different pH conditions. Row 4 represents the heat treated biomass with Sodium benzoate and potassium sorbate (SB+PS, 1000 ppm each) at the different pH conditions.

Samples without any microbial growth were considered for further storage study. After 16 days of storage, a TSA plating was done on all the heat treated biomass and non-heated biomass with SB+PS at pH 3, 4.5 and 5. The results are shown in FIG. 22 and Table 22.

TABLE 22

Types of microbes found in different biomass after 16 days of storage in the refrigerator at different pH

| Sample | pH 3 | pH 4.5 | pH 5 |
|---|---|---|---|
| non-heat treated biomass with SB + PS | Bacteria | none | none |
| Heated biomass-control | none | none | none |
| Heated biomass with BV | none | none | Fungus (yeast) |
| Heated biomass with SB + PS | bacteria | none | none |

Conclusions:

When there is only Fungi present in the biomass, they can be removed by heat treating the biomass to at least at 70° C. for 30 minutes. Addition of a mixture of 1000 ppm each potassium sorbate and sodium benzoate could also help prevent the microbial growth even if not heat treated and the pH of biomass is above pH 3.

Microbial Analysis of Liquid Egg Formulated Using Spray Dried *Euglena* Protein Concentrate Powder Objective:

There were microbes such as bacteria, and fungi were present in wet biomass and wet protein concentrate. Therefore, the shelf life of liquid egg produced using this wet protein concentrate is short due to microbial spoilage. It is expected that the microbes are killed during the spray drying process and it will be safe to use spray dried protein concentrate for the liquid egg production. The objective of the current study was to see if there is any microbial growth in the liquid egg prepared using spray dried protein concentrate powder and its shelf life.

Procedure:

The liquid egg was prepared using protein concentrate powder using the formula shown in Table 23. The egg was prepared in a sterilized container using sterilized equipment. The egg was then poured into sterilized 50 ml centrifuge tubes and stored in the refrigerator. A mixture of Cultured Dextrose Bio Vontage 2662 (BV, 0.25 w/w %) and 500 ppm of Nisin was added to the egg and also stored at the same condition. The antimicrobials were mixed with egg for 30 minutes, and the pH of the egg before and after addition of the antimicrobial mixture was taken. A TSA plate assay was done on the same day right after the egg was prepared and another plate after 3 days of storage. TSA plates were incubated at 30° C. for 3 days before analysis.

TABLE 23

Formulas used for egg formulation using dried protein concentrate powder

| Ingredient | Amount(g) | Amount (%) |
|---|---|---|
| Protein concentrate (powder) | 9 | 7.69 |
| Sunflower oil | 5 | 4.27 |
| Water | 100 | 85.47 |
| Gellan gum | 0.5 | 0.43 |
| Methyl Cellulose | 0.9 | 0.77 |
| Black salt | 0.3 | 0.26 |
| Yeast extract | 0.3 | 0.26 |
| onion powder | 0.2 | 0.17 |
| Baking powder | 0.5 | 0.43 |
| Sunflower lecithin | 0.3 | 0.26 |
| Total | 117 | 100 |

Results and Discussions:

The pH of the liquid egg prepared using protein concentrate powder was 6.75, pH of the egg did not change much with the addition of antimicrobial agents although it was expected to have a shift of pH to lower pH side due to the addition of BV (cultured dextrose).

Figure 23:
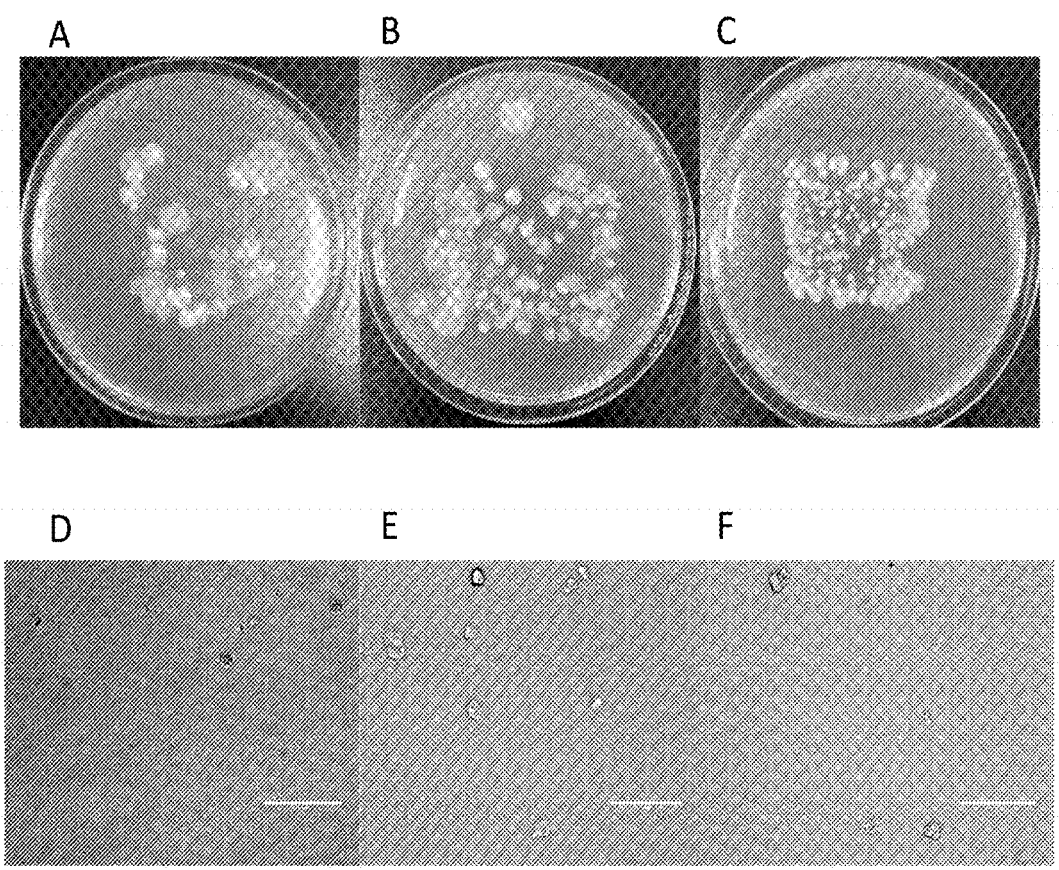
FIG. 23 shows images of the TSA plates (A-C) and microscopy images (D-F) of liquid egg prepared using protein concentrate powder. A) TSA plate on day 0 no antimicrobials, B) TSA plate on day 3 with no antimicrobials and C) TSA plate on day 3 with 0.35 w/w % Cultured dextrose and 500 ppm of Nisin added to the liquid egg preparation. D) Microscopy image on day 0 with no antimicrobials, E) Microscopy image on day 3 with no antimicrobials and F) Microscopy image on day 3 with 0.35 w/w % Cultured dextrose and 500 ppm of Nisin added to the liquid egg preparation.

The images of TSA plates of liquid egg done on the day of preparation and after 3 days of storage are shown in FIG. 23(A-C) as well as microscopic images (D-F). The microbial growth was observed in all the plates. The microscopic analysis showed there were both circular and rod-like bacteria present in the egg, and within three days the egg's smell changed negatively. However, with Nisin and BV treatment, the number of rod shaped bacteria did decrease compared to the control. It was also noticed that the viscosity of the egg increased almost to not flowing easily out of the tube with the changes to the recipe. Further optimization is needed in order to improve viscosity if this treatment is to be used.

Conclusions:

Conclusions: Since the pH of the egg formulation was close to pH 7, it was not possible to prevent any microbial growth even if we use spray dried protein concentrate powder for egg formulation. Therefore, it is important to try formulate the egg at a lower pH, for example 4.5, for future formulations.

Summary of Microbial Analysis of Biomass and Liquid Egg Formulated Using Protein Concentrate Powder While there was the presence of both bacteria and Fungi found in fresh biomass, it is likely that the microbial growth in biomass was determined by the pH of the biomass. pH 7 was found to be favourable for both bacteria and fungi while lower pH without heat treatment was still favourable for fungi (yeast). It was found that heat treatment of the biomass at 75° C. for 30 minutes can kill the fungi. After heat treatment, the biomass is fungal growth free for 16 days if refrigerated at a pH≤5. The activity of antimicrobial agents was affected by the pH, for example all of the tested antimicrobials were only functional if the pH of the biomass was pH≤5. A combination of potassium sorbate and sodium benzoate (1000 ppm each) could kill microbes and keep it out of any microbial growth if the pH of the biomass is below pH 5 and above pH 3. Since the pH of protein concentrate is at pH 7, the microbial growth cannot be prevented without further measures to changing its pH. If the pH of the liquid egg is pH 4.5, it should be able to prevent any microbial growth.

Example 16: Storage Stability and Pourability of Liquid Egg

It is essential to understand the changes occurring in liquid egg formulation during storage to see if there is any breakdown of components which affects the quality and safety of the product. Moreover, changes in viscosity of the liquid egg during storage also needs to be considered as it might affect the pourability and cooking quality of the liquid egg once it reaches the customer.

To understand the storage stability, the pourability, viscosity, consistency of the liquid egg formulation will be checked at different times during storage at the refrigerator. Also cooking will be done different days during storage to see how it performs.

The disclosures of each and every patent, patent application, publication, and accession number cited herein are hereby incorporated herein by reference in their entirety.

Preferences and options for a given aspect, feature, embodiment, or parameter of the invention should, unless the context indicates otherwise, be regarded as having been disclosed in combination with any and all preferences and options for all other aspects, features, embodiments, and parameters of the invention.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

What is claimed is:

1. A dry egg replacement composition comprising about 1% to about 100% *Euglena*-derived material, about 0.05% to about 70% additional protein source, and one or more additional ingredients, wherein the dry egg replacement composition comprises one or more functional property of a natural egg.

2. The dry egg replacement composition of claim 1, wherein the *Euglena*-derived material is selected from the group consisting of a *Euglena* biomass, *Euglena*-derived protein, a protein-rich flour derived from *Euglena*, a protein concentrate derived from *Euglena*, a protein isolate derived from *Euglena*, *Euglena*-derived beta-glucan isolate, *Euglena*-derived oils, and combinations thereof.

3. The dry egg replacement composition of claim 1, wherein the additional protein source is selected from the group consisting of pea protein, soy protein, corn protein, wheat protein, rice protein, beans protein, seed protein, nut protein, almond protein, peanut protein, seitan protein, lentil protein, chickpea protein, flaxseed protein, wild rice protein, quorn protein, chia seed protein, *quinoa* protein, oat protein, fava bean protein, buckwheat protein, bulgar protein, millet protein, microalgae protein, yellow pea protein, mung bean protein, hemp protein, sunflower protein, canola protein, lupin protein, legumes protein, potato protein, and combinations thereof.

4. The dry egg replacement composition of claim 3, wherein the ratio of *Euglena*-derived material to pea protein is about 20:80 to about 50:50.

5. The dry egg replacement composition of claim 3, wherein the ratio of *Euglena*-derived material to pea protein is about 40:60.

6. The dry egg replacement composition of claim 1, wherein the one or more additional ingredients are selected from the group consisting of gellan gum, methylcellulose, yeast extract, flavoring, antioxidant blend, maskers, leavening agents, baking powder, baking soda, enzymes, transglutaminase, emulsifiers, lecithin, mono- and diglycerides, binders, carrot fiber, defatted linseed flour, and combinations thereof.

7. The dry egg replacement composition of claim 6, wherein the flavoring is selected from the group consisting of black salt, black pepper, Himalayan sea salt, salt, onion powder, minced onion, roasted garlic, mushroom powder, yeast extract, and a combination thereof.

8. The dry egg replacement composition of claim 6, wherein the flavoring is in an amount of about 0.05% to about 0.5%.

9. The dry egg replacement composition of claim 1, further comprising one or more hydrocolloids.

10. The dry egg replacement composition of claim 9, wherein the one or more hydrocolloids is in an amount of about 0.05% to about 8%.

11. The dry egg replacement composition of claim 9, wherein the one or more hydrocolloids is selected from the group consisting of locust bean gum, a guar gum, a konjac gum, a gellan gum, a high methoxy pectin, a low methoxy pectin, an Agar, a kappa carrageenan, an iota carrageenan, a lambda carrageenan, an alginate, a curdlan, a methyl cellulose, a carboxymethyl cellulose (CMC), a xanthan gum, a gum Arabic, a *Euglena* derived beta-glucan, and combinations thereof.

12. The dry egg replacement composition of claim 1, wherein the dry egg replacement composition contains at least 6 g of protein.

13. The dry egg replacement composition of claim 1, wherein the *Euglena*-derived material is in an amount of about 40% to about 90% in the dry egg replacement composition.

14. The dry egg replacement composition of claim 1, wherein the additional protein source is in an amount of about 20% to about 60%.

15. The dry egg replacement composition of claim 1, wherein the one or more additional ingredients are in an amount of about 0.05% to about 5%.

16. The dry egg replacement composition of claim 1, wherein the dry egg replacement has at least 2 functional properties of a natural egg.

17. The dry egg replacement composition of claim 1, wherein the one or more functional properties is selected from the group consisting of complete nutrition, protein digestibility-corrected amino acid score (PDCAAS), gelation, foaming, viscosity, emulsification, water binding capacity, texture, elasticity, springiness, solubility, flavor, coagulation, aeration, creaminess, film forming property, sheen addition, shine addition, freeze stability, thaw stability, color, and combinations thereof.

18. A food product comprising the dry egg replacement composition of claim 1.

19. The food product of claim 18, wherein the dry egg replacement composition has provided one or more functional properties to the food product it has been incorporated into.

20. The food product of claim 19, wherein the functional properties are selected from the group consisting of crumb density, structure/texture, elasticity, springiness, coagulation, binding, moisturizing, mouthfeel, leavening, aeration/foaming, creaminess, and emulsification.

* * * * *